United States Patent
Knowlton

(10) Patent No.: US 10,321,948 B2
(45) Date of Patent: *Jun. 18, 2019

(54) PIXEL ARRAY MEDICAL DEVICES AND METHODS

(71) Applicant: SRGI HOLDINGS, LLC, Henderson, NV (US)

(72) Inventor: Edward Knowlton, Henderson, NV (US)

(73) Assignee: SRGI Holdings, LLC, Henderson, NV (US)

( * ) Notice: Subject to any disclaimer, the term of this patent is extended or adjusted under 35 U.S.C. 154(b) by 810 days.

This patent is subject to a terminal disclaimer.

(21) Appl. No.: 14/840,290

(22) Filed: Aug. 31, 2015

(65) Prior Publication Data

US 2016/0213419 A1    Jul. 28, 2016

Related U.S. Application Data

(63) Continuation-in-part of application No. 14/099,380, filed on Dec. 6, 2013, now Pat. No. 10,219,827,
(Continued)

(51) Int. Cl.
  *A61B 18/14*    (2006.01)
  *A61B 17/3211*  (2006.01)
  (Continued)

(52) U.S. Cl.
  CPC ........ *A61B 18/1402* (2013.01); *A61B 17/322* (2013.01); *A61B 17/3211* (2013.01);
  (Continued)

(58) Field of Classification Search
  CPC ............ A61B 17/32053; A61B 17/322; A61B 2017/3225; A61B 2017/320064;
  (Continued)

(56) References Cited

U.S. PATENT DOCUMENTS 1,610,089 A    12/1926  Heitler
3,867,942 A *   2/1975  Bellantoni ....... A61B 17/32053
                                                173/50
(Continued)

FOREIGN PATENT DOCUMENTS

CN    101530636 B    2/2012
KR    20080100795    6/2008
(Continued)

OTHER PUBLICATIONS

Branski, Ludwik K., et al.; "A Porcine Model of Full-Thickness Burn, Excision, and Skin Autographing"; Science Direct, www.sciencedirect.com, 2008 Elsevier Ltd and ISBI, Mar. 2008, 9 pages.
(Continued)

*Primary Examiner* — Anh T Dang
(74) *Attorney, Agent, or Firm* — IPR Law Group PC

(57) ABSTRACT

Systems, instruments, and methods are described in which an apparatus comprises a housing including a scalpet device. The scalpet device includes a scalpet array that includes scalpets arranged in a pattern. The scalpets are deployable from the housing to generate incised skin pixels at a target site. The housing is positioned and the scalpet array is deployed into tissue at the target site. Incised skin pixels are generated when the target site is a donor site, and skin defects are generated when the target site is a recipient site. The incised skin pixels are harvested.

94 Claims, 41 Drawing Sheets

Related U.S. Application Data which is a continuation-in-part of application No. 12/972,013, filed on Dec. 17, 2010, now Pat. No. 8,900,181, application No. 14/840,290, which is a continuation-in-part of application No. 14/505,090, filed on Oct. 2, 2014, now Pat. No. 10,076,354.

(60) Provisional application No. 62/044,060, filed on Aug. 29, 2014, provisional application No. 62/044,078, filed on Aug. 29, 2014, provisional application No. 62/044,089, filed on Aug. 29, 2014, provisional application No. 62/044,102, filed on Aug. 29, 2014.

(51) Int. Cl.
| | |
|---|---|
| *A61B 17/3205* | (2006.01) |
| *A61B 17/322* | (2006.01) |
| *A61M 5/46* | (2006.01) |
| *A61M 35/00* | (2006.01) |
| *A61B 17/00* | (2006.01) |
| *A61B 17/32* | (2006.01) |
| *A61B 17/30* | (2006.01) |

(52) U.S. Cl.
CPC ......... *A61B 17/32053* (2013.01); *A61M 5/46* (2013.01); *A61B 17/320068* (2013.01); *A61B 2017/00752* (2013.01); *A61B 2017/00761* (2013.01); *A61B 2017/00792* (2013.01); *A61B 2017/00884* (2013.01); *A61B 2017/00951* (2013.01); *A61B 2017/00969* (2013.01); *A61B 2017/306* (2013.01); *A61B 2017/3225* (2013.01); *A61B 2017/320052* (2013.01); *A61B 2017/320064* (2013.01); *A61M 35/003* (2013.01)

(58) Field of Classification Search
CPC ...... A61B 2017/00792; A61M 35/003; A61M 2037/0023
See application file for complete search history.

(56) References Cited

U.S. PATENT DOCUMENTS

| | | | |
|---|---|---|---|
| 4,018,228 A | 4/1977 | Goosen | |
| 4,098,278 A | 7/1978 | Schwartz | |
| 4,476,864 A | 10/1984 | Tezel | |
| 4,542,742 A | 9/1985 | Winkelman et al. | |
| 4,803,075 A | 2/1989 | Wallace et al. | |
| 5,123,907 A | 6/1992 | Romaine | |
| 5,141,513 A | 8/1992 | Fortune et al. | |
| 5,209,755 A | 5/1993 | Abrahan et al. | |
| 5,415,182 A | 5/1995 | Chin et al. | |
| 5,417,683 A | 5/1995 | Shiao | |
| 5,570,700 A | 11/1996 | Vogeler | |
| 5,643,308 A | 7/1997 | Markman | |
| 5,693,064 A | 12/1997 | Arnold | |
| 5,827,297 A | 10/1998 | Boudjema | |
| 5,858,019 A | 1/1999 | Ashraf | |
| 5,879,326 A | 3/1999 | Godshall et al. | |
| 5,922,000 A | 7/1999 | Chodorow | |
| 5,964,729 A | 10/1999 | Choi et al. | |
| 6,126,615 A | 10/2000 | Allen et al. | |
| 6,471,712 B2 | 10/2002 | Burres | |
| 6,497,875 B1 | 12/2002 | Sorrell et al. | |
| 6,572,625 B1 | 6/2003 | Rassman | |
| 6,585,746 B2 | 7/2003 | Gildenberg | |
| 6,589,202 B1 | 7/2003 | Powell | |
| 6,626,865 B1* | 9/2003 | Prisell | A61B 17/32053 604/116 |
| 6,669,685 B1 | 12/2003 | Rizoiu et al. | |
| 6,997,923 B2 | 2/2006 | Anderson et al. | |
| 7,204,828 B2 | 4/2007 | Rosiello | |
| 7,331,953 B2 | 2/2008 | Manstein et al. | |
| 7,354,423 B2 | 4/2008 | Zelickson et al. | |
| 7,621,933 B2 | 11/2009 | Bodduluri et al. | |
| 7,625,384 B2 | 12/2009 | Eriksson et al. | |
| 7,708,746 B2 | 5/2010 | Eriksson et al. | |
| 7,942,153 B2 | 5/2011 | Manstein et al. | |
| 7,962,192 B2 | 6/2011 | Bodduluri et al. | |
| 7,993,310 B2 | 8/2011 | Rosiello | |
| 8,535,299 B2 | 9/2013 | Giovannoli | |
| 8,540,731 B2 | 9/2013 | Kay et al. | |
| 8,545,489 B2 | 10/2013 | Giovannoli | |
| 8,690,863 B2 | 4/2014 | Chan et al. | |
| 8,900,181 B2 | 12/2014 | Knowlton | |
| 9,060,803 B2 | 6/2015 | Anderson et al. | |
| 9,351,792 B2 | 5/2016 | Manstein et al. | |
| 9,439,673 B2 | 9/2016 | Austen | |
| 9,468,459 B2 | 10/2016 | Hall et al. | |
| 2001/0053888 A1 | 12/2001 | Atahanasiou et al. | |
| 2002/0052619 A1 | 5/2002 | Transue | |
| 2002/0088779 A1 | 7/2002 | Neev et al. | |
| 2002/0183688 A1 | 12/2002 | Lastovich et al. | |
| 2003/0036770 A1 | 2/2003 | Markman | |
| 2003/0069548 A1 | 4/2003 | Connelly et al. | |
| 2003/0216719 A1 | 11/2003 | Debenedictis et al. | |
| 2004/0082940 A1 | 4/2004 | Black et al. | |
| 2004/0087893 A1 | 5/2004 | Kwon | |
| 2004/0087992 A1 | 5/2004 | Gartstein et al. | |
| 2004/0175690 A1 | 9/2004 | Mishra et al. | |
| 2005/0049582 A1 | 3/2005 | DeBenedictis et al. | |
| 2005/0283141 A1 | 12/2005 | Giovannoli | |
| 2006/0051404 A1 | 3/2006 | Yehoshua et al. | |
| 2006/0155266 A1 | 7/2006 | Manstein et al. | |
| 2007/0073217 A1 | 3/2007 | James | |
| 2007/0073327 A1 | 3/2007 | Giovannoli | |
| 2007/0179481 A1 | 8/2007 | Frangineas et al. | |
| 2007/0179516 A1 | 8/2007 | Mishra et al. | |
| 2007/0207131 A1 | 9/2007 | Boss et al. | |
| 2007/0224173 A1 | 9/2007 | Koullick et al. | |
| 2008/0172047 A1 | 7/2008 | Altshuler et al. | |
| 2010/0121307 A1 | 5/2010 | Lockard | |
| 2011/0009860 A1 | 1/2011 | Chornenky et al. | |
| 2011/0077664 A1* | 3/2011 | Schulz | A61B 17/322 606/132 |
| 2011/0208089 A1 | 8/2011 | Sundheimer et al. | |
| 2011/0251602 A1 | 10/2011 | Anderson et al. | |
| 2011/0257588 A1* | 10/2011 | Knowlton | A61B 17/322 604/22 |
| 2011/0264115 A1 | 10/2011 | Asrani et al. | |
| 2011/0282239 A1* | 11/2011 | Conlon | A61B 10/0275 600/566 |
| 2011/0313429 A1 | 12/2011 | Anderson et al. | |
| 2012/0035599 A1 | 2/2012 | Sabir et al. | |
| 2012/0041430 A1 | 2/2012 | Anderson et al. | |
| 2012/0226214 A1 | 9/2012 | Gurtner et al. | |
| 2012/0271320 A1 | 10/2012 | Hall et al. | |
| 2012/0323139 A1 | 12/2012 | Richardson | |
| 2012/0323325 A1 | 12/2012 | Fulton | |
| 2013/0090669 A1 | 4/2013 | Bellomo | |
| 2013/0204273 A1 | 8/2013 | Sabir et al. | |
| 2013/0304090 A1 | 11/2013 | Oostman et al. | |
| 2014/0031801 A1 | 1/2014 | Giovannoli | |
| 2014/0303648 A1 | 10/2014 | Knowlton | |
| 2015/0216545 A1 | 8/2015 | Anderson et al. | |
| 2015/0238214 A1 | 8/2015 | Anderson et al. | |
| 2015/0366719 A1 | 12/2015 | Levinson et al. | |
| 2016/0095592 A1 | 4/2016 | Levinson et al. | |
| 2016/0192961 A1 | 7/2016 | Ginggen | |
| 2016/0310157 A1 | 10/2016 | Guiles et al. | |
| 2016/0310158 A1 | 10/2016 | Guiles et al. | |
| 2016/0310159 A1 | 10/2016 | Guiles et al. | |
| 2016/0317721 A1 | 11/2016 | Ginggen et al. | |
| 2016/0367280 A1 | 12/2016 | Austen | |
| 2017/0042561 A1 | 2/2017 | Hall et al. | |

FOREIGN PATENT DOCUMENTS

| | | |
|---|---|---|
| KR | 200303833 Y1 | 8/2013 |
| WO | 0145566 A1 | 6/2001 |
| WO | 2005072181 A2 | 8/2005 |
| WO | 2008002064 A1 | 1/2008 |

(56) References Cited

FOREIGN PATENT DOCUMENTS

| WO | 2009146068 A1 | 12/2009 |
| WO | 2012103483 A2 | 8/2012 |
| WO | 2013013196 A1 | 1/2013 |
| WO | 2013013199 A2 | 1/2013 |
| WO | 2014028626 A1 | 2/2014 |
| WO | 2014089488 A2 | 6/2014 |

OTHER PUBLICATIONS

Akan, Mithat M.D., et al.; "An Alternative Method to Minimize Pain in the Split-Thickness Skin Graft Donor Site"; From the Department of Plastic and Reconstructive Surgery, Dr. Lütfi Kirdar Kartal Education and Research Hospital, Istanbul; and the Department of Plastic and Reconstructive Surgery, Ankara Education and Research Hospital. Received for publication Dec. 20, 2000; revised Aug. 20, 2002.

Ablaza, Valerie J. M.D., et al.; "An Alternative Treatment for the Split Skin-Graft Donor Site"; Aesthetic Plastic Surgery, 21:207-209, Springer-Verlag New York, Inc. 1997, 3 pages.

Jones, Larry M. M.D.; "The Biobrane Stent"; From the Mercy Hospital of Pittsburgh, Journal of Burn Care and Rehabilitation, vol. 19, No. 4, 1998, 2 pages.

Andreassi, Andrea M.D., et al.; "Classification and Pathophysiology of Skin Grafts"; Clinics in Dermatology, vol. 23 pp. 332-337, 2005 Elsevier Inc.

Hallock, Geoffrey G. M.D.; "The Cosmetic Split-Thickness Skin Graft"; From the Division of Plastic Surgery, Lehigh Valley Hospital, vol. 104, No. 7, Feb. 1999, 3 pages.

Williamson, J. S. M.D., et al.; "Cultured Epithelial Autograft: Five Years of Clinical Experience with Twenty-Eight Patients"; The Journal of Trauma: Injury, Infection, and Critical Care, Issue: vol. 39(2), Aug. 1995, pp. 309-319.

Cirodde, Audrey, et al.; "Cultured Epithelial Autografts in Massive Burns: A Single-Center Retrospective Study with 63 Patients"; Science Direct, www.sciencedirect.com, 2011 Elsevier Ltd and ISBI, Mar. 2011, 9 pages.

Clugston, Patricia A. M.D., et al.; "Cultured Epithelial Autografts: Three Years of Clinical Experience with Eighteen Patients"; Journal of Burn Care and Rehabilitation, vol. 12, No. 6 Nov./Dec. 1991, 7 pages.

Thourani, Vinod H. M.D., et al.; "Factors Affecting Success of Split-Thickness Skin Grafts in the Modern Burn Unit"; The Journal of Trauma, Injury, Infection, and Critical Care; vol. 54 pp. 562-568, Dec. 2002.

Sheridan, Robert L., et al.; "Initial Experience with a Composite Autologous Skin Substitute"; Shriners Burn Hospital Boston MA, USA, Burns vol. 27 pp. 421-424, Nov. 2000.

Elliot, Michael and Vandervord, John; "Initial Experience with Cultured Epithelial Autografts in Massively Burnt Patients"; Department of Plastic Surgery, Royal North Shore Hospital, Sydney, Australia, ANZ J. Surg. vol. 72 pp. 893-895, Aug. 2002.

Hansbrough, Wendy BS, RN, et al. "Management of Skin-Grafted Burn Wounds with Xeroform* and Layers of Dry Coarse-Mesh Gauze Dressing Results in Excellent Graft Take and Minimal Nursing Time"; From the University of California, San Diego, Regional Burn Center and Medical Center; Jul. 1994, Copyright 1995 by Burn Science Publishers, Inc. 4 pages.

Wells, Mark D. M.D., Kim, David S. M.D.; "A New Method of Skin-Graft Stabilization: The Reston Technique"; From the Division of Plastic Surgery, Department of Surgery, University of Kentucky Chandler Medical Center, Lexington KY, Dec. 1994, 3 pages, Copyright by Little, Brown and Company 1995.

Hazani, Ron M.D. et al., "Optimizing Aesthetic Results in Skin Grafting"; From the Department of Surgery, Division of Plastic Surgery, University of Louisville, Louisville, Kentucky, The American Surgeon, vol. 78, Feb. 2012, 4 pages.

Lee, Haguen; "Outcomes of Sprayed Cultured Epithelial Autografts for Full-Thickness Wounds"; A Single-Centre Experience, Science Direct, www.sciencedirect.com, 2012 Elsevier Ltd and ISBI, Jan. 2012, 6 pages.

Greenwood, John M.D., et ; "Real-Time Demonstration of Split Skin Graft Inosculation and Integra Dermal Matrix Neovascularization Using Confocal Laser Scanning Microscopy"; Burns Unit, Royal Adelaide Hospital, North Terrace Adelaide, SA 5000, Australia, published Aug. 2009, Journal of Plastic Surgery, vol. 9.

Lindenblatt, Nicole, M.D., et al.; "A New Model for Studying the Revascularization of Skin Grafts In Vivo: The Role of Angiogenesis"; From the Division of Plastic and Reconstructive Surgery, University Hospital Zurich; the Institute for Clinical andExperimental Surgery, University of Saarland; and the Institute for Experimental Surgery, University of Rostock. Received for publication Dec. 15, 2007; accepted May 28, 2008. www.PRSJournal.com, 12 pages.

Dornseifer, Ulf M.D., et al.; "The Ideal Split-Thickness Skin Graft Donor Site Dressing"; From the Department of Plastic, Reconstructive, Hand, and Burn Surgery, Clinic Bogenhausen, Technical University, Munich, Germany, Annals of Plastic Surgery, vol. 63, No. 2 Aug. 2009, 3 pages.

Dornseifer, Ulf M.D., et al.; "The Ideal Split-Thickness Skin Graft Donor-Site Dressing: A Clinical Comparative Trial of a Modified Polyurethane Dressing and Aquacel"; Burn Surgery, Academic Hospital Munich Bogenhausen, Technical University Munich, and the Institute of Medical Statistics and Epidemiology, Technical University Munich. Received for publication Jun. 2010; accepted Mar. 2011. Copyright © 2011 by the American Society of Plastic Surgeons. WWW. PRSJournal.com, 7 pages.

Penington, Anthony, Morrison, Wayne A.; "Skin Graft Failure Is Predicted by Waist-Hip Ratio: a Marker for Metabolic Syndrome"; Department of Surgery, St. Vincent's Hospital, University of Melbourne, Melbourne, Victoria, Australia; Jun. 2006, copyright 2007 Royal Australasian College of Surgeons, 3 pages.

Wendt, James Robert M.D., et al.; "Long-Term Survival of Human Skin Allografts in Patients with Immunosuppression"; From the Department of Plastic Surgery, Hoag Memorial Hospital Presbyterian; Amgen; and Department of Pathology and Laboratory Medicine, UCLA Clinical Cytogenetics Laboratory. Received for publication Apr. 1, 2001; 8 pages.

Mimoun, Maurice M.D. et al.; "The Scalp Is an Advantageous Donor Site for Thin-Skin Grafts: A Report on 945 Harvested Samples"; From the Plastic, Aesthetic, Reconstructive and Burn Surgery Unit, Rothschild Hospital, and the Burn Unit, Saint-Antoine Hospital. Received for publication Nov. 2004; accepted Apr. 2005. Copyright © 2006 by the American Society of Plastic Surgeons, 5 pages.

Wood, F.M., et al.; "The Use of Cultured Epithelial Autograft in the Treatment of Major Burn Injuries: A Critical Review of the Literature"; Burn Service WA, Royal Perth Hospital, Princess Margaret Hospital for Children,University of Western Australia, GPO Box X2213, Perth Western Australia 6847, Australia Clinical Cell Culture, Australia, accepted Jan. 2006, copyright 2006 Elsevier Ltd and ISBI, 7 pages.

Bello, Ysabel M., et al.; "Tissue-Engineered Skin, Current Status in Wound Healing"; American Journal Clinical Dermatology, vol. 2 (5), 2001, pp. 305-313, Miami FL USA.

Kogan, Leonid, M.D.,PhD, Govrin-Yehudain, Jacky, M.D.; "Vertical (Two-Layer) Skin Grafting: New Reserves for Autologic Skin"; From Plastic Surgery Unit, Western Galilee Hospital, Nahariya, Israel. Received Dec. 2001 Accepted Oct. 2002, 3 pages.

Fischer, John P. M.D., et al. "Complications in Body Contouring Procedures: An Analysis of 1797 Patients from the 2005 to 2010 American College of Surgeons National Surgical Quality Improvement Program Databases"; From the Division of Plastic Surgery, Hospital of the University of Pennsylvania. Received for publication Apr. 2013; accepted Jul. 2013, WWW.PRSJournal.com, 10 pages.

Motttura, A. Aldo, M.D.; "Open Frontal Lift: A Conservative Approach"; Aesthetic Plastic Surgery, vol. 30 pp. 381-389, copyright 2006 Springer Science Business Media, Inc.

(56) References Cited

OTHER PUBLICATIONS

Polder, Kristel D. M.D., Bruce, Suzanne, M.D.; "Radiofrequency: Thermage"; Facial Plastic Surgery Clinics, Apr. 2011, pp. 347-359, copyright 2011 Elsevier Inc. All rights reserved.
Pallua, N., Wolter, ; "The Lipo-Facelift: Merging the Face-Lift and Liposculpture: Eight Years Experience and a Preliminary Observational Study"; Received: Feb. 2013 / Accepted: Apr. 30, 2013 / Published online: Oct. 2013 Springer Science+Business Media New York and International Society of Aesthetic Plastic Surgery 2013, 7 pages.
Burns, Jay A.; "Thermage: Monopolar Radiofrequency"; Aesthetic Surgery Journal, Nov./Dec. 2005, vol. 25, No. 6, 5 pages.
Sukal, Sean A. M.D., Geronemus, Roy G. M.D.; "Thermage: The Nonablative Radiofrequency for Rejuvenation"; Laser and Skin Surgery Center of New York, New York, NY, USA, Clinics in Dermatology vol. 26, pp. 602-607, 2008, copyright 2008 Elsevier Inc., 6 pages.
Sklar, Lindsay, et al.; "Use of Transcutaneous Ultrasound for Lipolysis and Skin Tightening: A Review"; Received: Jul. 2013 / Accepted: Jan. 2014, copyright Springer Science+Business Media New York and International Society of Aesthetic Plastic Surgery 2014, 13 pages.
Ito, Keita, Perren, Stephan M.; "Biology of Fracture Healing"; AO Principles of Fracture Management, AO Foundation Publishing, Jan. 2013, 5 pages.
Ford, Charles N., Bless, Diane M; "Clinical Experience with Injectable Collagen for Vocal Fold Augmentation"; Larynscope 96(8), Aug. 1986, pp. 863-869.
Kaplan, Ernest N., Falces, Edward, Tolleth, Hale; "Clinical Utilization of Injectable Collagen"; From the Department of Surgery Division of Plastic and Reconstructive Surgery, Stanford University School of Medicine, Annals of Plastic Surgery, vol. 10, No. 6, Jun. 1983, 15 pages, Palo Alto, CA.
O'Connor, K.W., Lehman, G.A.; "Endoscopic Placement of Collagen at the Lower Esophageal Sphincter to Inhibit Gastroesophageal Reflux: a Pilot Study of 10 Medically Intractable Patients"; Gastrointestinal Endoscopy, Received Mar. 1987, Accepted May 1987, 7 pages, Indianapolis, IN.
Ford, Charles N., Staskowski, Paul A., Bless, Diane M.; "Autologous Collagen Vocal Fold Injection: A Preliminary Clinical Study"; Presented at the Meeting of the Middle Section of the American Laryngological, Rhinological and Otological Society Inc., Laryngoscope 105, Sep. 1995, 5 pages, Omaha NE.
Giordano, Antonio, Galderisi, Umberto, Marino, Ignazio R.; "From the Laboratory Bench to the Patient's Bedside: An Update on Clinical Trials with Mesenchymal Stem Cells"; Department of Experimental Medicine of Biotechnology and Molecular Biology, Second University of Naples, Oct. 2006, 10 pages, Naples Italy.
Matton, G., Anseeuw, A., DE Keyser, F.; "The History of Injectable Biomaterials and the Biology of Collagen"; Aesthetic Plastic Surgery, vol. 9, Issue 2, Jun. 1985, 8 pages, Gent Belguim.
Klein, Arnold William; "Implantation Technics for Injectable Collagen"; Journal of the American Academy of Dermatology, vol. 9, Issue 2, Aug. 1983, pp. 224-228. Beverly Hills, CA.
Cooperman, Linda, S., MacKinnon, Victoria, Bechler, Gail, Pharriss, Bruce B.; "Injectable Collagen: A Six-Year Clinical Investigation"; Aesthetic Plastic Surgery, vol. 9, Issue 2, Jun. 1985, pp. 145-151.
Ford, Charles N., Bless, Diane M.; "A Preliminary Study of Injectable Collagen in Human Vocal Fold Augmentation"; From the Division of Otolaryngology, Department of Surgery, University of Wisconsin and Middleton Veterans Administration Hospital and Department of Communicative Disorders, University of Wisconsin and Waisman Center on Mental Retardation and Human Development; Presented at the Annual Meeting of the American Academy of Otolaryngology—Head and Neck Surgery, Sep. 1985, 9 pages, Las Vega, NV.
Ford, Charles N., Bless, Diane M., Loftus, Jean M.; "Role of Injectable Collagen in the Treatment of Glottic Insufficiency: A Study of 119 Patients"; Annals of Otology, Rhinology and Laryngology, vol. 101, Issue 3, Mar. 1992, 11 pages, Madison WI.
Frey, P., Berger, D., Jenny, P., Herzog, B.; "Subureteral Collagen Injection for the Endoscopic Treatment of Vesicoureteral Reflux in Children. Followup Study of 97 Treated Ureters and Histological Analysis of Collagen Implants"; Department of Pediatric Surgery, CHUV, Lausanne and University Children's Hospital; The Journal of Urology, vol. 148 pp. 718-723, Aug. 1992, Basel Switzerland.
Shortliffe, Linda M. Dairiki, Freiha, Fuad S., Kessler, Robert, Stamely,Thomas A., Constantinou, Christos E.: "Treatment of Urinary Incontinence by the Periurethral Implantation of Glutaraldehyde Cross-Linked Collagen"; The Journal of Urology, vol. 141, Mar. 1989, 3 pages, Palo Alto, CA.
International Search Report and Written Opinion for International PCT Application No. PCT/US2013/073678 dated May 27, 2014, 18 pages.
International Search Report and Written Opinion for International PCT Application No. PCT/US2014/058886 dated Mar. 3, 2015, 22 pages.
International Search Report and Written Opinion for International PCT Application No. PCT/US2015/047695 dated Jan. 28, 2016, 40 pages.
International Search Report and Written Opinion for International PCT Application No. PCT/US2015/047721 dated Feb. 3, 2016, 20 pages.
International Search Report and Written Opinion for International PCT Application No. PCT/US2016/016834 dated May 17, 2016, 11 pages.
Supplementary European Search Report for EP Application No. EP13859972 dated Jun. 10, 2016, 6 pages.
Alguire, Patrick; Mathes, Barbara M.; "Skin Biopsy Techniques for the Internist"; received from the Division of Internal Medicine (PCA) and the Division of Dermatology (BMM), University of Florida, Gainesville, vol. 13, Jan. 1998, 9 pages.
Zuber, Thomas J.; "Fusiform Exision"; American Family Physician, vol. 67, No. 7, Apr. 2003, 6 pages.
Russe, Elisabeth, et al. "Micro-Fractional, Direction Skin Tightening: A Porcine Model"; Lasers in Surgery and Medicine 48:264-269, Accepted Nov. 4, 2015, Published online Dec. 2, 2015 in Wiley Online Library (wileyonlinelibrary.com), 6 pages.

* cited by examiner

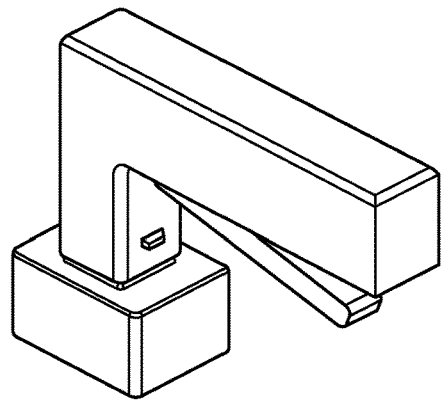
*FIG. 18*
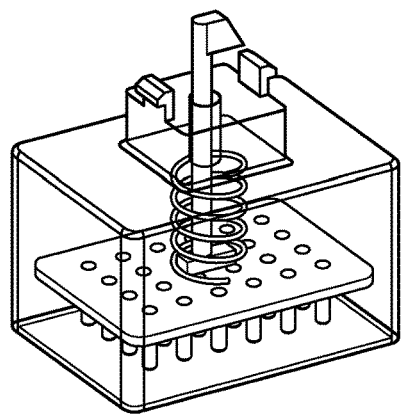 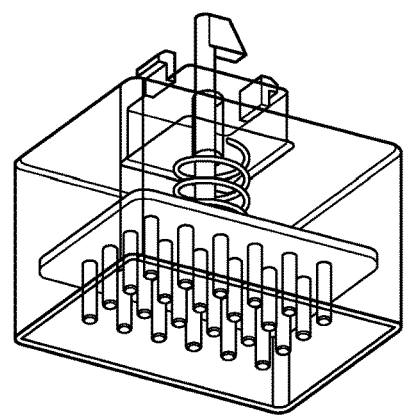
*FIG. 19A*  *FIG. 19B*
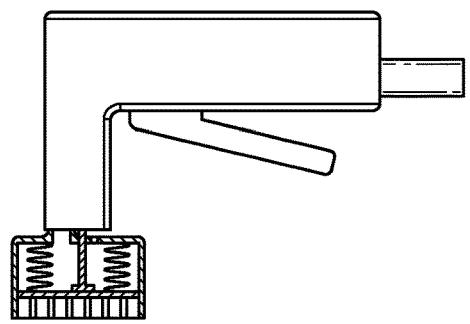
*FIG. 20*

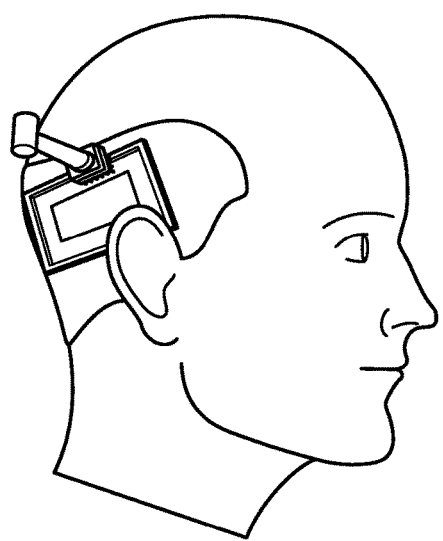 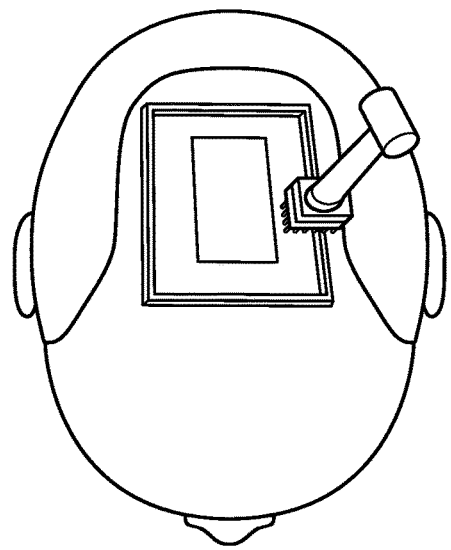
Donor Hair Transplant Site
FIG. 27
Recipient Hair Transplant Site
FIG. 28

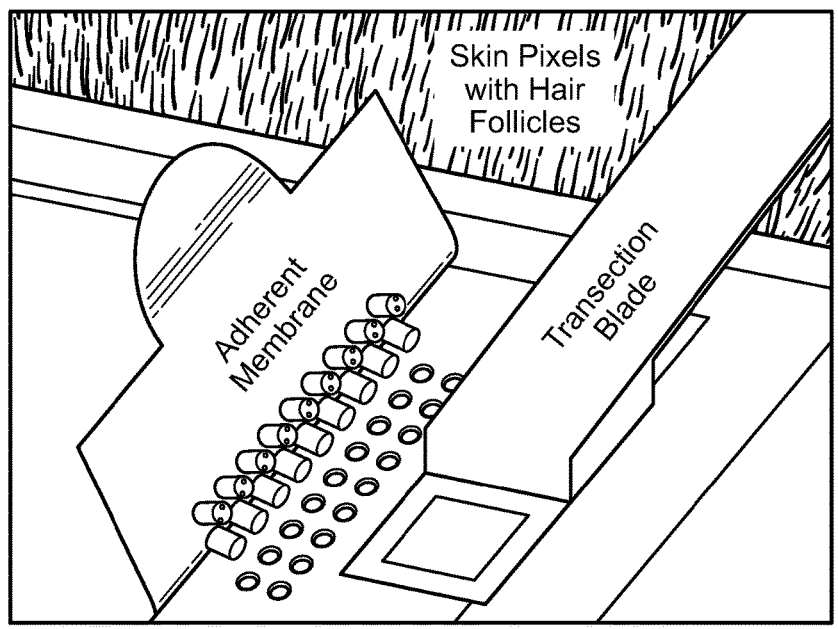
FIG. 32
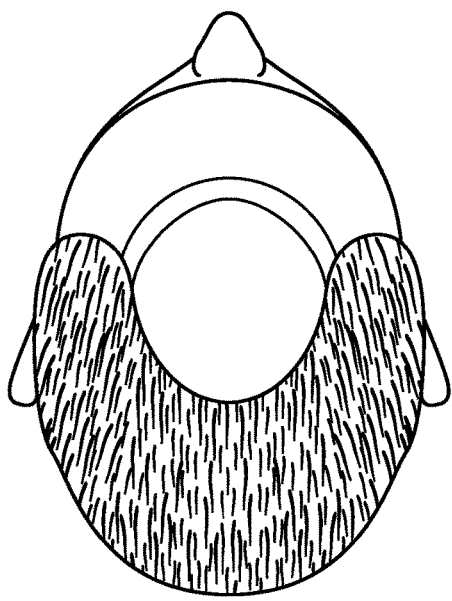 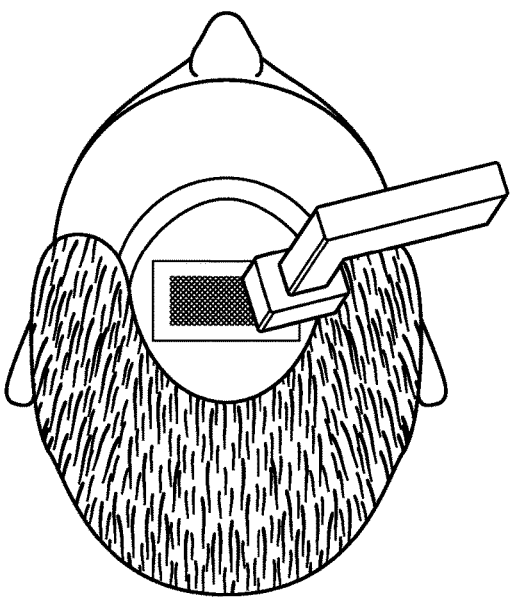
FIG. 33  FIG. 34

PIXEL ARRAY MEDICAL DEVICES AND METHODS

RELATED APPLICATIONS

This application claims the benefit of United States (US) Patent Application No. 62/044,060, filed Aug. 29, 2014.

This application claims the benefit of U.S. Patent Application No. 62/044,078, filed Aug. 29, 2014.

This application claims the benefit of U.S. Patent Application No. 62/044,089, filed Aug. 29, 2014.

This application claims the benefit of U.S. Patent Application No. 62/044,102, filed Aug. 29, 2014.

This application is a continuation in part of U.S. patent application Ser. No. 14/099,380, filed Dec. 6, 2013, which claims the benefit of U.S. Patent Application No. 61/734,313, filed Dec. 6, 2012.

This application is a continuation in part of U.S. patent application Ser. No. 12/972,013, filed Dec. 17, 2010, which claims the benefit of U.S. Patent Application No. 61/288,141, filed Dec. 18, 2009.

This application is a continuation in part of United States (US) patent application Ser. No. 14/505,090, filed Oct. 2, 2014.

TECHNICAL FIELD

The embodiments herein relate to medical systems, instruments or devices, and methods and, more particularly, to medical instrumentation and methods applied to the surgical management of burns, skin defects, and hair transplantation.

BACKGROUND

The aging process is most visibly depicted by the development of dependent skin laxity. This life long process may become evident as early as the third decade of life and will progressively worsen over subsequent decades. Histological research has shown that dependant stretching or age related laxity of the skin is due in part to progressive dermal atrophy associated with a reduction of skin tensile strength. When combined with the downward force of gravity, age related dermal atrophy will result in the two dimensional expansion of the skin envelope. The clinical manifestation of this physical-histological process is redundant skin laxity. The most affected areas are the head and neck, upper arms, thighs, breasts, lower abdomen and knee regions. The most visible of all areas are the head and neck. In this region, prominent "turkey gobbler" laxity of neck and "jowls" of the lower face are due to an unaesthetic dependency of skin in these areas.

Plastic surgery procedures have been developed to resect the redundant lax skin. These procedures must employ long incisions that are typically hidden around anatomical boundaries such as the ear and scalp for a facelift and the inframammary fold for a breast uplift (mastopexy). However, some areas of skin laxity resection are a poor tradeoff between the aesthetic enhancement of tighter skin and the visibility of the surgical incision. For this reason, skin redundancies of the upper arm, suprapatellar knees, thighs and buttocks are not routinely resected due to the visibility of the surgical scar. The frequency and negative societal impact of this aesthetic deformity has prompted the development of the "Face Lift" surgical procedure. Other related plastic surgical procedures in different regions are the Abdominoplasty (Abdomen), the Mastopexy (Breasts), and the Brachioplasty (Upper Arms). Inherent adverse features of these surgical procedures are post-operative pain, scarring and the risk of surgical complications. Even though the aesthetic enhancement of these procedures is an acceptable tradeoff to the significant surgical incisions required, extensive permanent scarring is always an incumbent part of these procedures. For this reason, plastic surgeons design these procedures to hide the extensive scarring around anatomical borders such as the hairline (Facelift), the inframmary fold (Mastopexy), and the inguinal crease (Abdominoplasty). However, many of these incisions are hidden distant to the region of skin laxity, thereby limiting their effectiveness. Other skin laxity regions such as the Suprapatellar (upper-front) knee are not amendable to plastic surgical resections due to the poor tradeoff with a more visible surgical scar.

More recently, electromagnetic medical devices that create a reverse thermal gradient (i.e., Thermage) have attempted with variable success to tighten skin without surgery. At this time, these electromagnetic devices are best deployed in patients with a moderate amount of skin laxity. Because of the limitations of electromagnetic devices and potential side effects of surgery, a minimally invasive technology is needed to circumvent surgically related scarring and the clinical variability of electromagnetic heating of the skin. For many patients who have age related skin laxity (neck and face, arms, axillas, thighs, knees, buttocks, abdomen, bra line, ptosis of the breast), fractional resection of excess skin could augment a significant segment of traditional plastic surgery.

Even more significant than aesthetic modification of the skin envelope is the surgical management of burns and other trauma related skin defects. Significant burns are classified by the total body surface burned and by the depth of thermal destruction. First-degree and second-degree burns are generally managed in a non-surgical fashion with the application of topical creams and burn dressings. Deeper third-degree burns involve the full thickness thermal destruction of the skin. The surgical management of these serious injuries involves the debridement of the burn eschar and the application of split thickness grafts.

Any full thickness skin defect, most frequently created from burning, trauma, or the resection of a skin malignancy, can be closed with either skin flap transfers or skin grafts using current commercial instrumentation. Both surgical approaches require harvesting from a donor site. The use of a skin flap is further limited by the need of to include a pedicle blood supply and in most cases by the need to directly close the donor site.

The split thickness skin graft procedure, due to immunological constraints, requires the harvesting of autologous skin grafts, that is, from the same patient. Typically, the donor site on the burn patient is chosen in a non-burned area and a partial thickness sheet of skin is harvested from that area. Incumbent upon this procedure is the creation of a partial thickness skin defect at the donor site. This donor site defect is itself similar to a deep second-degree burn. Healing by re-epithelialization of this site is often painful and may be prolonged for several days. In addition, a visible donor site deformity is created that is permanently thinner and more de-pigmented than the surrounding skin. For patients who have burns over a significant surface area, the extensive harvesting of skin grafts may also be limited by the availability of non-burned areas.

For these reasons, there is a need in the rapidly expanding aesthetic market for instrumentation and procedures for aesthetic surgical skin tightening. There is also a need for systems, instruments or devices, and procedures that enable the repeated harvesting of skin grafts from the same donor site while eliminating donor site deformity.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 18 shows a side perspective view of the PAD assembly, under an embodiment.

FIG. 19A shows a top perspective view of the scalpet device for use with the PAD assembly, under an embodiment.

FIG. 19B shows a bottom perspective view of the scalpet device for use with the PAD assembly, under an embodiment.

FIG. 20 shows a side view of the punch impact device including a vacuum component, under an embodiment.

FIG. 27 shows harvesting of donor follicles, under an embodiment.

FIG. 28 shows preparation of the recipient site, under an embodiment.

FIG. 32 shows hair plug harvesting using the perforated plate at the occipital donor site, under an embodiment.

FIG. 33 shows creation of the visible hairline, under an embodiment.

FIG. 34 shows preparation of the donor site using the patterned perforated plate and spring-loaded pixilation device to create identical skin defects at the recipient site, under an embodiment.

DETAILED DESCRIPTION

Figure 1:
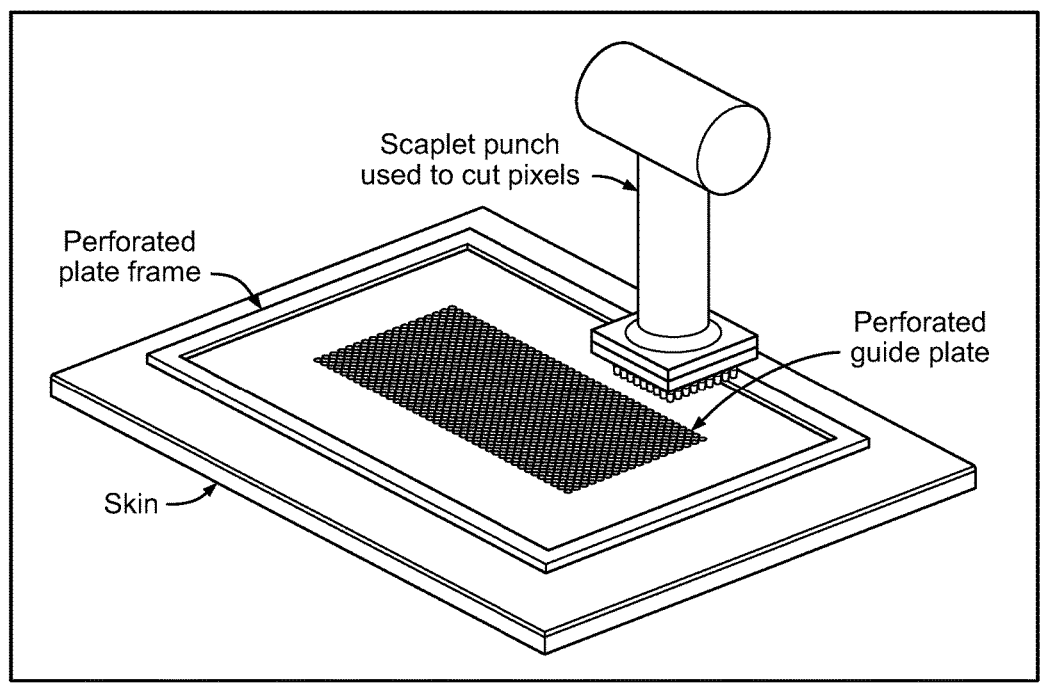
FIG. 1 shows the PAD Kit placed at a target site, under an embodiment.

Embodiments described herein satisfy the expanding aesthetic market for instrumentation and procedures for aesthetic surgical skin tightening. Additionally, the embodiment enable the repeated harvesting of skin grafts from the same donor site while eliminating donor site deformity. The embodiments described herein are configured to resect redundant lax skin without visible scarring so that all areas of redundant skin laxity can be resected by the pixel array dermatome and procedures may be performed in areas that were previously off limits due to the visibility of the surgical incision. The technical effects realized through the embodiments described herein include smooth, tightened skin without visible scarring or long scars along anatomical borders.

Embodiments described in detail herein, which include pixel skin grafting instrumentation and methods, are configured to provide the capability to repeatedly harvest split thickness skin grafts without visible scarring of the donor site. During the procedure, a Pixel Array Dermatome (PAD) is used to harvest the skin graft from the chosen donor site. During the harvesting procedure, a pixilated skin graft is deposited onto a flexible, semi-porous, adherent membrane. The harvested skin graft/membrane composite is then applied directly to the recipient skin defect site. The fractionally resected donor site is closed with the application of an adherent sheeting or bandage (e.g., Flexzan® sheeting, etc.) that functions for a period of time (e.g., one week, etc.) as a large butterfly bandage. The intradermal skin defects generated by the PAD are closed to promote a primary healing process in which the normal epidermal-dermal architecture is realigned in an anatomical fashion to minimize scarring. Also occurring postoperatively, the adherent membrane is desquamated (shed) with the stratum corneum of the graft; the membrane can then be removed without disruption of the graft from the recipient bed.

Numerous effects realized by the pixel skin grafting procedure deserve explanation. Because the skin graft is pixelated it provides interstices for drainage between skin plug components, which enhances the percentage of "takes," compared to sheet skin grafts. During the first post-operative week, the skin graft "takes" at the recipient site by a process of neovascularization in which new vessels from the recipient bed of the skin defect grow into the new skin graft. The semiporous membrane conducts the exudate into the dressing.

The flexible membrane is configured with an elastic recoil property that promotes apposition of component skin plugs within the graft/membrane composite; promoting primary adjacent healing of the skin graft plugs and converting the pixilated appearance of the skin graft into a more uniform sheet morphology. Furthermore, the membrane aligns the micro-architectural components skin plugs, so epidermis aligns with epidermis and dermis aligns with dermis, promoting a primary healing process that reduces scarring.

There are numerous major clinical applications for the dermatomes described in detail herein, including fractional skin resection for skin tightening, fractional hair grafting for alopecia, and fractional skin harvesting for skin grafting. Fractional skin resection of an embodiment comprises harvesting skin plugs using an adherent membrane, however the fractionally incised skin plugs can be evacuated without harvesting. The paradigm of incising, evacuating and closing is most descriptive of the clinical application of skin tightening. The embodiments described herein are configured to facilitate incising and evacuating and, in order to provide for a larger scalpet array with a greater number of scalpets, the embodiments include a novel means of incising the skin surface.

Pixel array medical systems, instruments or devices, and methods are described for skin grafting and skin resection procedures, and hair transplantation procedures. In the following description, numerous specific details are introduced to provide a thorough understanding of, and enabling description for, embodiments herein. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

The following terms are intended to have the following general meaning as they may be used herein. The terms are not however limited to the meanings stated herein as the meanings of any term can include other meanings as understood or applied by one skilled in the art.

"First degree burn" as used herein includes a superficial thermal injury in which there is no disruption of the epidermis from the dermis. A first-degree burn is visualized as erythema (redness) of the skin.

"Second degree burn" as used herein includes a relatively deeper burn in which there is disruption of the epidermis from the dermis and where a variable thickness of the dermis is also denatured. Most second-degree burns are associated with blister formation. Deep second-degree burns may convert to full thickness third degree burns, usually by oxidation or infection.

"Third degree burn" as used herein includes a burn associated with the full thickness thermal destruction of the skin including the epidermis and the dermis. A third degree burn may also be associated with thermal destruction of deeper, underlying tissues (subcutaneous and muscle layers).

"Ablation" as used herein includes the removal of tissue by destruction of the tissue e.g., thermal ablation of a skin lesion by a laser.

"Autograft" as used herein includes a graft taken from the same patient.

"Backed Adherent Membrane" as used herein includes the elastic adherent membrane that captures the transected skin plugs. The Backed Adherent Membrane of an embodiment is backed on the outer surface to retain alignment of the skin plugs during harvest. After harvesting of the skin plugs, the backing is removed from the adherent membrane with harvested skin plugs. The membrane of an embodiment is porous to allow for drainage when placed at the recipient site. The membrane of an embodiment also possesses an elastic recoil property, so that when the backing is removed, it brings the sides of the skin plugs closer to each other to promote healing at the recipient site as a sheet graft.

"Burn Scar Contraction" as used herein includes the tightening of scar tissue that occurs during the wound healing process. This process is more likely to occur with an untreated third degree burn.

"Burn Scar Contracture" as used herein includes a band of scar tissue that either limits the range of motion of a joint or band of scar tissue that distorts the appearance of the patient i.e., a burn scar contracture of the face.

"Dermatome" as used herein includes an instrument that "cuts skin" or harvests a sheet split thickness skin graft. Examples of drum dermatomes include the Padgett and Reese dermatomes. Electrically powered dermatomes are the Zimmer dermatome and one electric version of the Padgett dermatome.

"Dermis" as used herein includes the deep layer of skin that is the main structural support and primarily comprises non-cellular collagen fibers. Fibroblasts are cells in the dermis that produce the collagen protein fibers.

"Donor Site" as used herein includes the anatomical site from which a skin graft is harvested.

"Epidermis" as used herein includes the outer layer of skin comprising viable epidermal cells and nonviable stratum corneum that acts as a biological barrier.

"Excise" as used herein includes the surgical removal of tissue.

"Excisional Skin Defect" as used herein includes a partial thickness or, more typically, a full thickness defect that results from the surgical removal (excision/resection) of skin (lesion).

"FTSG" as used herein includes a Full Thickness Skin Graft in which the entire thickness of the skin is harvested. With the exception of an instrument as described herein, the donor site is closed as a surgical incision. For this reason, FTSG is limited in the surface area that can be harvested.

"Granulation Tissue" as used herein includes highly vascularized tissue that grows in response to the absence of skin in a full-thickness skin defect. Granulation Tissue is the ideal base for a skin graft recipient site.

"Healing by primary intention" as used herein includes the wound healing process in which normal anatomical structures are realigned with a minimum of scar tissue formation. Morphologically the scar is less likely to be visible.

"Healing by secondary intention" as used herein includes a less organized wound healing process wherein healing occurs with less alignment of normal anatomical structures and with an increased deposition of scar collagen. Morphologically, the scar is more likely to be visible.

"Homograft" as used herein includes a graft taken from a different human and applied as a temporary biological dressing to a recipient site on a patient. Most homografts are harvested as cadaver skin. A temporary "take" of a homograft can be partially achieved with immunosuppression but homografts are eventually replaced by autografts if the patient survives.

"Incise" as used herein includes the making of a surgical incision without removal of tissue.

"Mesh Split Thickness Skin Graft" as used herein includes a split thickness skin graft that is expanded in its surface area by repetitiously incising the harvested skin graft with an instrument called a "mesher". A meshed split thickness skin graft has a higher percentage of "take" than a sheet graft because it allows drainage through the graft and conforms better to the contour irregularities of the recipient site. However, it does result in an unsightly reticulated appearance of the graft at the recipient site.

"PAD" as used herein includes a Pixel Array Dermatome, the class of instruments for fractional skin resection.

"PAD Kit" as used herein includes the disposable single use procedure kit comprising the perforated guide plate, scalpet stamper, the guide plate frame, the backed adherent membrane and the transection blade.

"Perforated Guide Plate" as used herein includes a perforated plate comprising the entire graft harvest area in which the holes of the guide plate are aligned with the scalpets of the handled stamper or the Slip-on PAD. The plate will also function as a guard to prevent inadvertent laceration of the adjacent skin. The perforations of the Guide Plate can be different geometries such as, but not limited to, round, oval, square, rectangular, and/or triangular.

"Pixelated Full Thickness Skin Graft" as used herein includes a Full Thickness Skin Graft that has been harvested with an instrument as described herein without reduced visibly apparent scarring at the donor site. The graft will also possess an enhanced appearance at the recipient site similar to a sheet FTSG but will conform better to recipient site and will have a higher percentage of 'take' due to drainage interstices between skin plugs. Another significant advantage of the pixelated FTSG in comparison to a sheet FTSG is the ability to graft larger surface areas that would otherwise require a STSG. This advantage is due to the capability to harvest from multiple donor sites with reduced visible scarring.

"Pixelated Graft Harvest" as used herein includes the skin graft harvesting from a donor site by an instrument as described in detail herein.

"Pixelated Spilt Thickness Skin Graft" as used herein includes a partial thickness skin graft that has been harvested with an SRG instrument. The skin graft shares the advantages of a meshed skin graft without unsightly donor and recipient sites.

"Recipient Site" as used herein includes the skin defect site where a skin graft is applied.

"Resect" as used herein includes excising.

"Scalpel" as used herein includes the single-edged knife that incises skin and soft tissue.

"Scalpet" as used herein includes the term that describes the small geometrically-shaped (e.g., circle, ellipse, rectangle, square, etc.) scalpel that incises a plug of skin.

"Scalpet Array" as used herein includes the arrangement or array of multiple scalpets secured to a substrate (e.g., a base plate, stamper, handled stamper, tip, disposable tip, etc.).

"Scalpet Stamper" as used herein includes a handled scalpet array instrument component of the PAD Kit that incises skin plugs through the perforated guide plate.

"Scar" as used herein includes the histological deposition of disorganized collagen following wounding, or the morphological deformity that is visually apparent from the histological deposition of disorganized collagen following wounding.

"Sheet Full Thickness Skin Graft" as used herein includes reference to application of the FTSG at the recipient site as continuous sheet. The appearance of an FTSG is superior to the appearance of a STSG and for this reason it is primarily used for skin grafting in visually apparent areas such as the face.

"Sheet Split Thickness Skin Graft" as used herein includes a partial thickness skin graft that is a continuous sheet and is associated with the typical donor site deformity.

"Skin Defect" as used herein includes the absence of the full thickness of skin that may also include the subcutaneous fat layer and deeper structures such as muscle. Skin defects can occur from a variety of causes i.e., burns, trauma, surgical excision of malignancies and the correction of congenital deformities.

"Skin Pixel" as used herein includes a piece of skin comprising epidermis and a partial or full thickness of the dermis that is cut by the scalpet; the skin pixel may include skin adnexa such as a hair follicle with or without a cuff of subcutaneous fat; also includes Skin Plug.

"Skin Plug" as used herein includes a circular (or other geometric shaped) piece of skin comprising epidermis and a partial or full thickness of the dermis that is incised by the scalpet, transected by the transection blade and captured by the adherent-backed membrane.

"STSG" as used herein includes the Partial Thickness Skin Graft in which the epidermis and a portion of the dermis is harvested with the graft.

"Subcutaneous Fat Layer" as used herein includes the layer that is immediately below the skin and is principally comprised of fat cells referred to as lipocytes. This layer functions as principle insulation layer from the environment.

"Transection Blade" as used herein includes a horizontally-aligned single edged blade that can be either slotted to the frame of the perforated plate or attached to the outrigger arm of the drum dermatome as described in detail herein. The transection blade transects the base of the incised skin plugs.

"Wound Healing" as used herein includes the obligate biological process that occurs from any type of wounding whether it be one or more of thermal, kinetic and surgical.

"Xenograft" as used herein includes a graft taken from a different species and applied as a temporary biological dressing to a recipient site on a patient.

Multiple embodiments of pixel array medical systems, instruments or devices, and methods for use are described in detail herein. The systems, instruments or devices, and methods described herein comprise minimally invasive surgical approaches for skin grafting and for skin resection that tightens lax skin without visible scarring via a device used in various surgical procedures such as plastic surgery procedures, and additionally for hair transplantation. In some embodiments, the device is a single use disposable instrument. The embodiments herein circumvent surgically related scarring and the clinical variability of electromagnetic heating of the skin and perform small multiple pixilated resections of skin as a minimally invasive alternative to large plastic surgical resections of skin. The embodiments herein can also be employed in hair transplantation, and in areas of the body that may be off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

For many patients who have age related skin laxity (for non-limiting examples, neck and face, arms, axillas, thighs, knees, buttocks, abdomen, bra line, ptosis of the breast, etc.), the minimally invasive pixel array medical devices and methods herein perform pixilated transection/resection of excess skin, replacing plastic surgery with its incumbent scarring. Generally, the procedures described herein are performed in an office setting under a local anesthetic with minimal perioperative discomfort, but are not so limited. In comparison to a prolonged healing phase from plastic surgery, only a short recovery period is required, preferably applying a dressing and a support garment worn over the treatment area for a pre-specified period of time (e.g., 5 days, 7 days, etc.). There will be minimal or no pain associated with the procedure.

The relatively small (e.g., in a range of approximately 0.5 mm to 4.0 mm) skin defects generated by the instrumentation described herein are closed with the application of an adherent Flexan® sheet. Functioning as a large butterfly bandage, the Flexan® sheet can be pulled in a direction ("vector") that maximizes the aesthetic contouring of the treatment area. A compressive elastic garment is applied over the dressing to further assist aesthetic contouring. After completion of the initial healing phase, the multiplicity of small linear scars within the treatment area will have reduced visibility in comparison to larger plastic surgical incisions on the same area. Additional skin tightening is likely to occur over several months due to the delayed wound healing response. Other potential applications of the embodiments described herein include hair transplantation as well as the treatment of Alopecia, Snoring/Sleep apnea, Orthopedics/Physiatry, Vaginal Tightening, Female Urinary incontinence, and tightening of gastrointestinal sphincters.

Significant burns are classified by the total body surface burned and by the depth of thermal destruction, and the methods used to manage these burns depend largely on the classification. First-degree and second-degree burns are usually managed in a non-surgical fashion with the application of topical creams and burn dressings. Deeper third-degree burns involve the full thickness thermal destruction of the skin, creating a full thickness skin defect. The surgical management of this serious injury usually involves the debridement of the burn eschar and the application of split thickness grafts.

A full thickness skin defect, most frequently created from burning, trauma, or the resection of a skin malignancy, can be closed with either skin flap transfers or skin grafts using conventional commercial instrumentation. Both surgical approaches require harvesting from a donor site. The use of a skin flap is further limited by the need of to include a pedicle blood supply and in most cases by the need to directly close the donor site.

The split thickness skin graft procedure, due to immunological constraints, requires the harvesting of autologous skin grafts from the same patient. Typically, the donor site on the burn patient is chosen in a non-burned area and a partial thickness sheet of skin is harvested from that area. Incumbent upon this procedure is the creation of a partial thickness skin defect at the donor site. This donor site defect itself is similar to a deep second-degree burn. Healing by re-epithelialization of this site is often painful and may be prolonged for several days. In addition, a visible donor site deformity is typically created that is permanently thinner and more de-pigmented than the surrounding skin. For patients who have burns over a significant surface area, the extensive harvesting of skin grafts may also be limited by the availability of non-burned areas.

Both conventional surgical approaches to close skin defects (flap transfer and skin grafting) are not only associated with significant scarring of the skin defect recipient site but also with the donor site from which the graft is harvested. In contrast to the conventional procedures, embodiments described herein comprise Pixel Skin Grafting Procedures, also referred to as a pixel array procedures, that eliminate this donor site deformity and provide a method to re-harvest skin grafts from any pre-existing donor site including either sheet or pixelated donor sites. This ability to re-harvest skin grafts from pre-existing donor sites will reduce the surface area requirement for donor site skin and provide additional skin grafting capability in severely burned patients who have limited surface area of unburned donor skin.

The Pixel Skin Grafting Procedure of an embodiment is used as a full thickness skin graft. Many clinical applications such as facial skin grafting, hand surgery, and the repair of congenital deformities are best performed with full thickness skin grafts. The texture, pigmentation and overall morphology of a full thickness skin graft more closely resembles the skin adjacent to a defect than a split thickness skin graft. For this reason, full thickness skin grafting in visibly apparent areas is superior in appearance than split thickness skin grafts. The main drawback to full thickness skin grafts under conventional procedures is the extensive linear scarring created from the surgical closure of the full thickness donor site defect; this scarring limits the size and utility of full thickness skin grafting.

In comparison, the full thickness skin grafting of the Pixel Skin Grafting Procedure described herein is less limited by size and utility as the linear donor site scar is eliminated. Thus, many skin defects routinely covered with split thickness skin grafts will instead be treated using pixelated full thickness skin grafts.

The Pixel Skin Grafting Procedure provides the capability to harvest split thickness and full thickness skin grafts with minimal visible scarring of the donor site. During the procedure, a Pixel Array Dermatome (PAD) device is used to harvest the skin graft from a chosen donor site. During the harvesting procedure, the pixilated skin graft is deposited onto an adherent membrane. The adherent membrane of an embodiment includes a flexible, semi-porous, adherent membrane, but the embodiment is not so limited. The harvested skin graft/membrane composite is then applied directly to the recipient skin defect site. The fractionally resected donor site is closed with the application of an adherent Flexan® sheeting that functions for one week as a large butterfly bandage. The relatively small (e.g., 1.5 mm) intradermal circular skin defects are closed to promote a primary healing process in which the normal epidermal-dermal architecture is realigned in an anatomical fashion to minimize scarring. Also occurring approximately one week postoperatively, the adherent membrane is desquamated (shed) with the stratum corneum of the graft; the membrane can then be removed without disruption of the graft from the recipient bed. Thus, healing of the donor site occurs rapidly with minimal discomfort and scarring.

Because the skin graft at the recipient defect site using the Pixel Skin Grafting Procedure is pixelated it provides interstices for drainage between skin pixel components, which enhances the percentage of "takes," compared to sheet skin grafts. During the first post-operative week (approximate), the skin graft will "take" at the recipient site by a process of neovascularization in which new vessels from the recipient bed of the skin defect grow into the new skin graft. The semi-porous membrane will conduct the transudate (fluid) into the dressing. Furthermore, the flexible membrane is designed with an elastic recoil property that promotes apposition of component skin pixels within the graft/membrane composite and promotes primary adjacent healing of the skin graft pixels, converting the pixilated appearance of the skin graft to a uniform sheet morphology. Additionally, the membrane aligns the micro-architectural component skin pixels, so epidermis aligns with epidermis and dermis aligns with dermis, promoting a primary healing process that reduces scarring. Moreover, pixelated skin grafts more easily conform to an irregular recipient site.

Embodiments described herein also include a Pixel Skin Resection Procedure, also referred to herein as the Pixel Procedure. For many patients who have age related skin laxity (neck and face, arms, axillas, thighs, knees, buttocks, abdomen, bra line, ptosis of the breast, etc.), fractional resection of excess skin could replace a significant segment of plastic surgery with its incumbent scarring. Generally, the Pixel Procedure will be performed in an office setting under a local anesthetic. The post procedure recovery period includes wearing of a support garment over the treatment area for a pre-specified number (e.g., five, seven, etc.) of days (e.g., five days, seven days, etc.). Relatively little or no pain is anticipated to be associated with the procedure. The small (e.g., 1.5 mm) circular skin defects will be closed with the application of an adherent Flexan® sheet. Functioning as a large butterfly bandage, the Flexan® sheet is pulled in a direction ("vector") that maximizes the aesthetic contouring of the treatment area. A compressive elastic garment is then applied over the dressing to further assist aesthetic contouring. After completion of the initial healing phase, the multiplicity of small linear scars within the treatment area will not be visibly apparent. Furthermore, additional skin tightening will subsequently occur over several months due to the delayed wound healing response. Consequently, the Pixel Procedure is a minimally invasive alternative to the extensive scarring of Plastic Surgery.

The pixel array medical devices of an embodiment include a PAD Kit. FIG. 1 shows the PAD Kit placed at a target site, under an embodiment. The PAD Kit comprises a flat perforated guide plate (guide plate), a scalpet punch or device that includes a scalpet array (FIGS. 1-3), a backed adhesive membrane or adherent substrate (FIG. 4), and a skin pixel transection blade (FIG. 5), but is not so limited. The scalpet punch of an embodiment is a handheld device but is not so limited. The guide plate is optional in an alternative embodiment, as described in detail herein.

Figure 2:
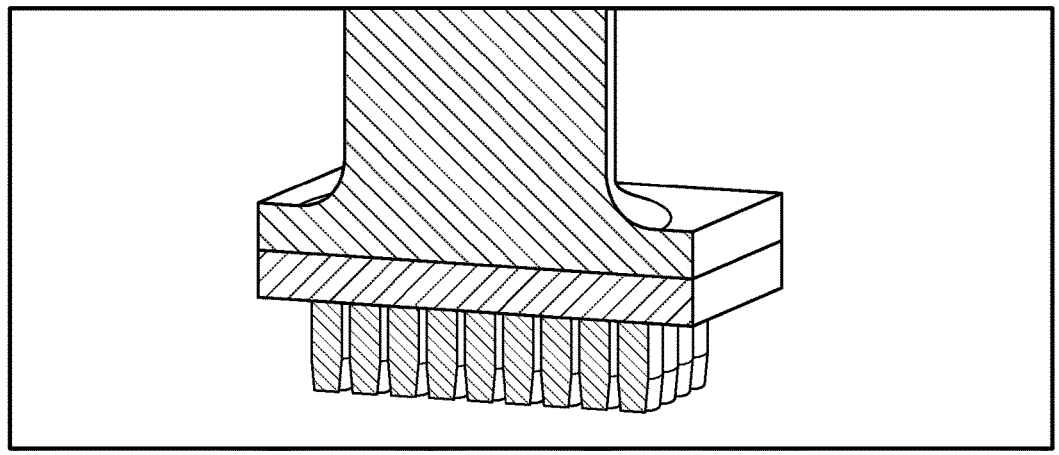
FIG. 2 is a cross-section of a scalpet punch or device including a scalpet array, under an embodiment.
Figure 3:
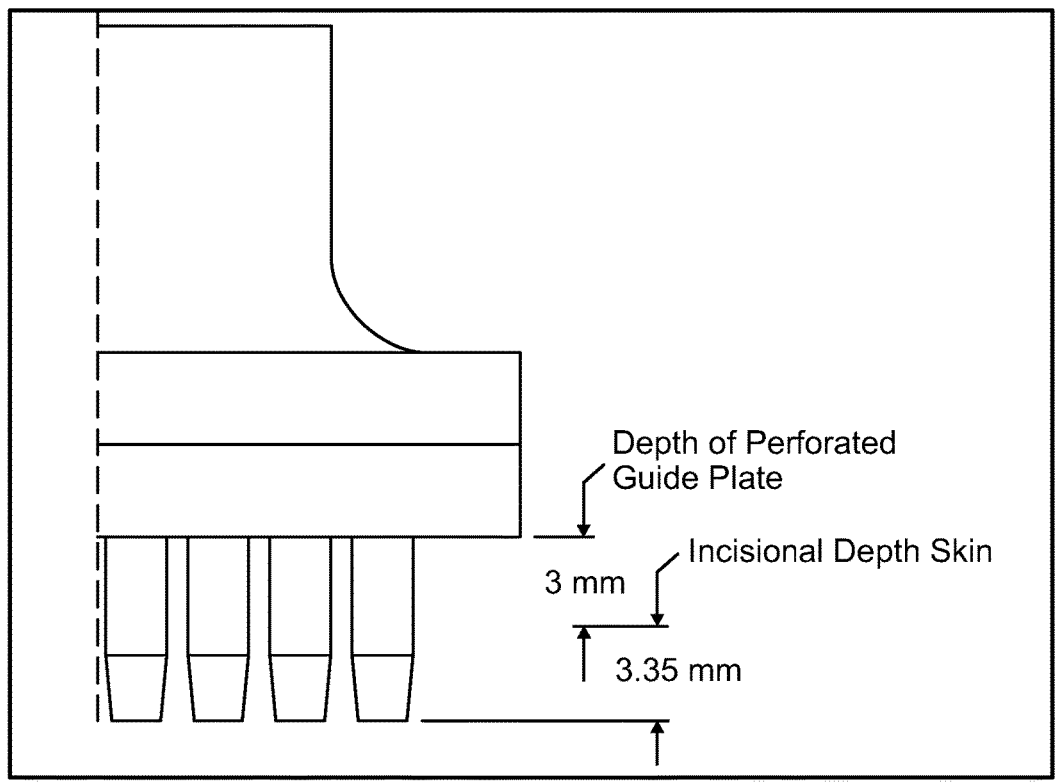
FIG. 3 is a partial cross-section of a scalpet punch or device including a scalpet array, under an embodiment.

FIG. 2 is a cross-section of a PAD Kit scalpet punch including a scalpet array, under an embodiment. The scalpet array includes one or more scalpets. FIG. 3 is a partial cross-section of a PAD Kit scalpet punch including a scalpet array, under an embodiment. The partial cross-section shows the total length of the scalpets of the scalpet array is determined by the thickness of the perforated guide plate and the incisional depth into the skin, but the embodiment is not so limited.

Figure 4:
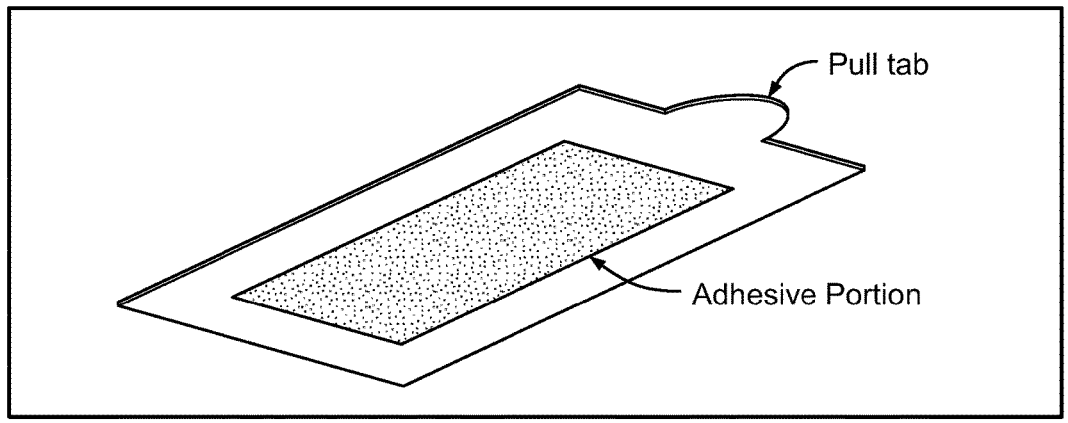
FIG. 4 shows the adhesive membrane with backing (adherent substrate) included in a PAD Kit, under an embodiment.

FIG. 4 shows the adhesive membrane with backing (adherent substrate) included in a PAD Kit, under an embodiment. The undersurface of the adhesive membrane is applied to the incised skin at the target site.

Figure 5:
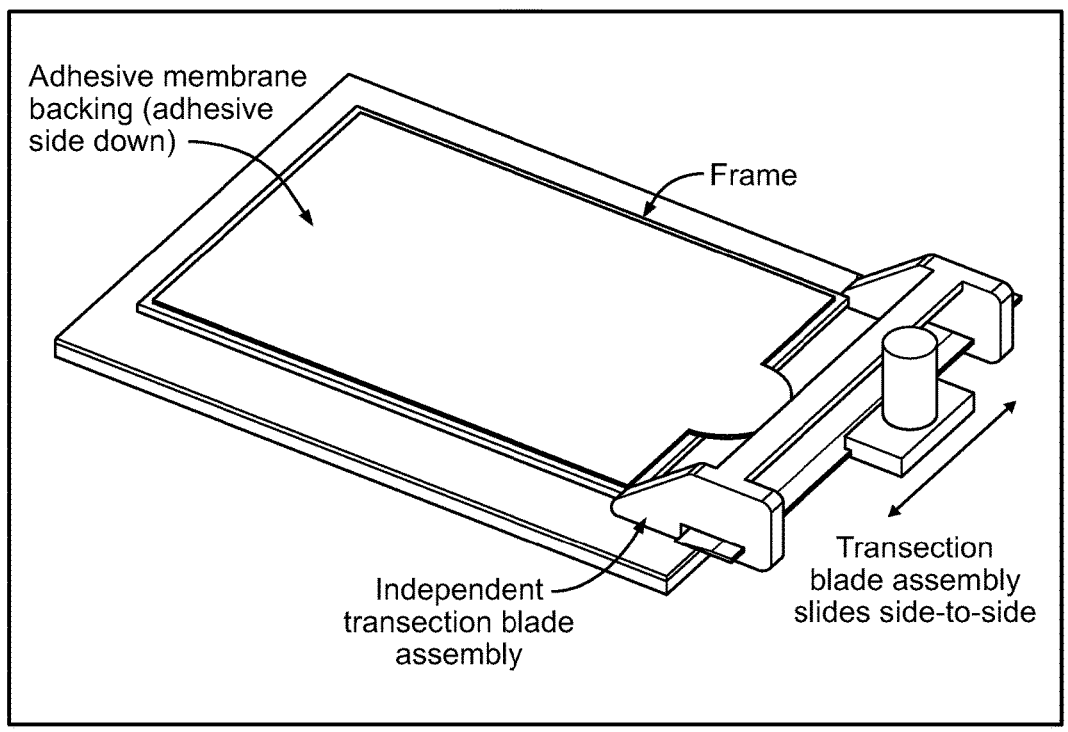
FIG. 5 shows the adhesive membrane (adherent substrate) when used with the PAD Kit frame and blade assembly, under an embodiment.

FIG. 5 shows the adhesive membrane (adherent substrate) when used with the PAD Kit frame and blade assembly, under an embodiment. The top surface of the adhesive membrane is oriented with the adhesive side down inside the frame and then pressed over the perforated plate to capture the extruded skin pixels, also referred to herein as plugs or skin pixels.

With reference to FIG. 1, the perforated guide plate is applied to the skin resection/donor site during a procedure using the PAD Kit. The scalpet punch is applied through at least a set of perforations of the perforated guide plate to incise the skin pixels. The scalpet punch is applied numerous times to a number of sets of perforations when the scalpet array of the punch includes fewer scalpets then the total number of perforations of the guide plate. Following one or more serial applications with the scalpet punch, the incised skin pixels or plugs are captured onto the adherent substrate. The adherent substrate is then applied in a manner so the adhesive captures the extruded skin pixels or plugs. As an example, the top surface of the adherent substrate of an embodiment is oriented with the adhesive side down inside the frame (when the frame is used) and then pressed over the perforated plate to capture the extruded skin pixels or plugs. As the membrane is pulled up, the captured skin pixels are transected at their base by the transection blade.

Figure 6:
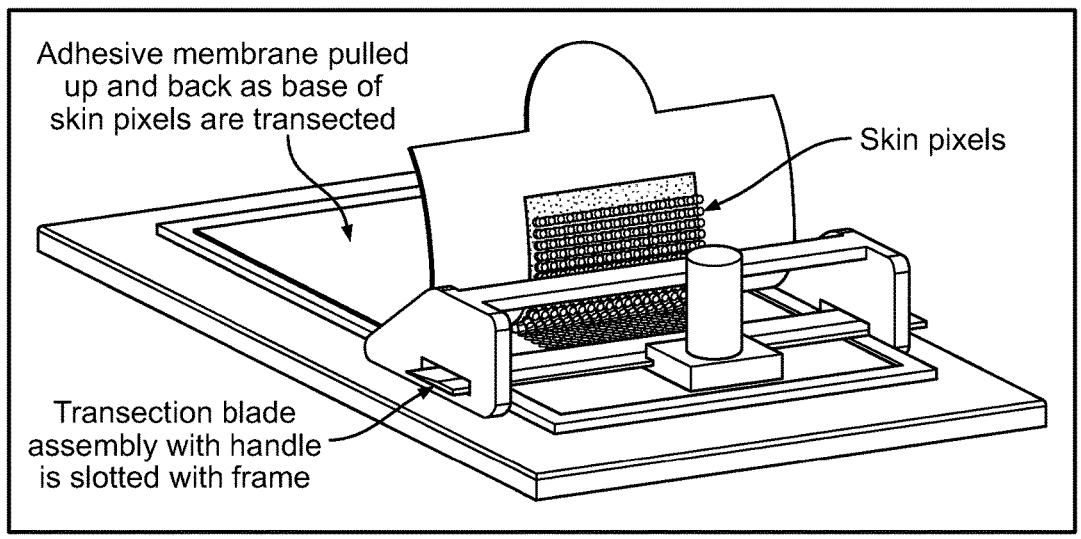
FIG. 6 shows the removal of skin pixels, under an embodiment.
Figure 7:
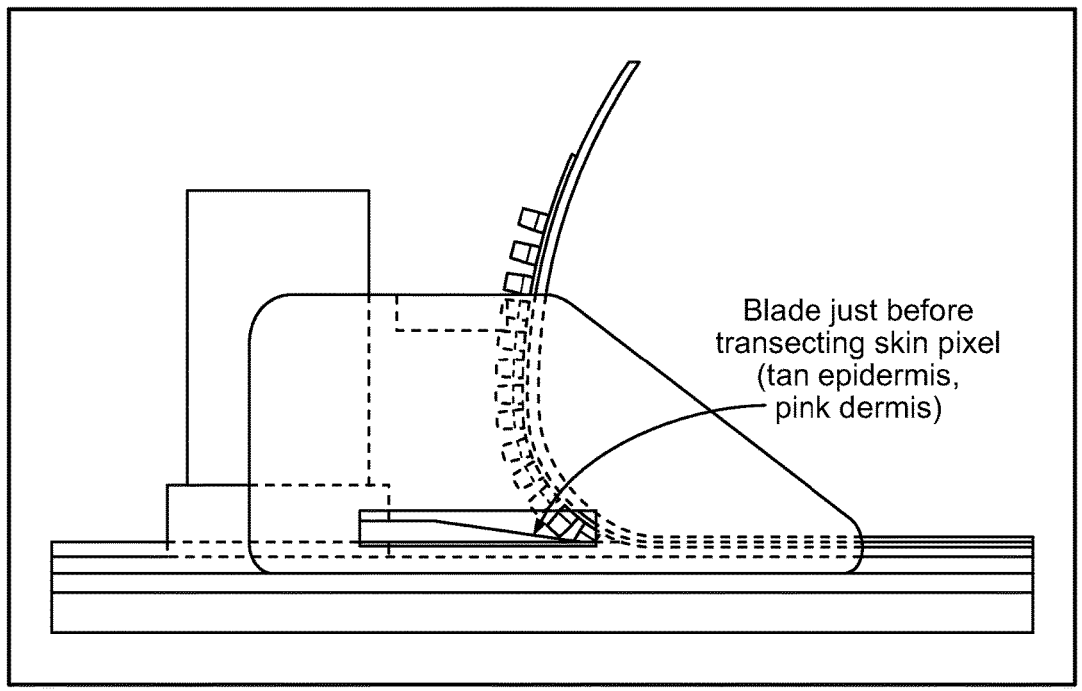
FIG. 7 is a side view of blade transection and removal of incised skin pixels with the PAD Kit, under an embodiment.
Figure 8:
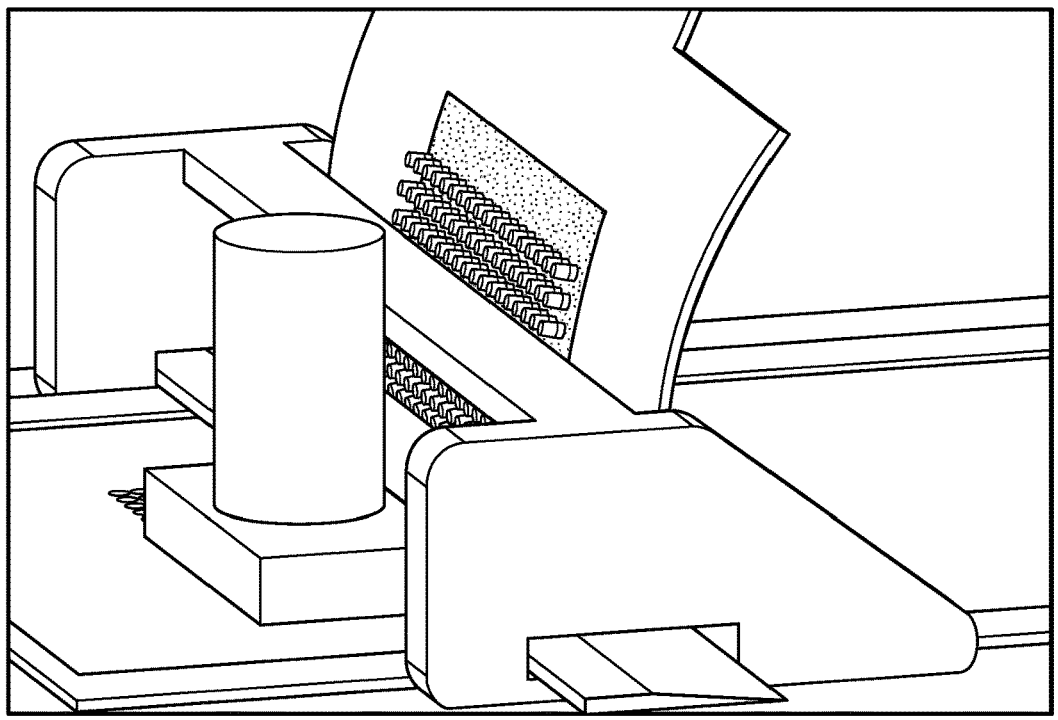
FIG. 8 is an isometric view of blade/pixel interaction during a procedure using the PAD Kit, under an embodiment.
Figure 9:
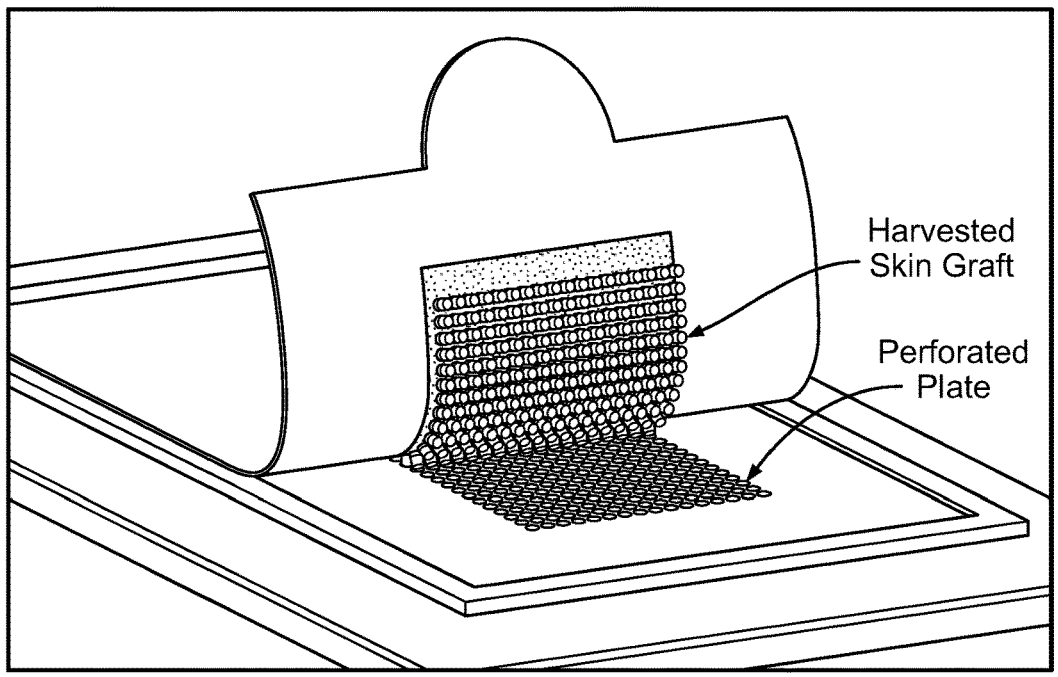
FIG. 9 is another view during a procedure using the PAD Kit (blade removed for clarity) showing both harvested skin pixels or plugs transected and captured and non-transected skin pixels or plugs prior to transection, under an embodiment.

FIG. 6 shows the removal of skin pixels, under an embodiment. The adherent substrate is pulled up and back (away) from the target site, and this act lifts or pulls the incised skin pixels or plugs. As the adherent substrate is being pulled up, the transection blade is used to transect the bases of the incised skin pixels. FIG. 7 is a side view of blade transection and removal of incised skin pixels with the PAD Kit, under an embodiment. Pixel harvesting is completed with the transection of the base of the skin pixels or plugs. FIG. 8 is an isometric view of blade/pixel interaction during a procedure using the PAD Kit, under an embodiment. FIG. 9 is another view during a procedure using the PAD Kit (blade removed for clarity) showing both harvested skin pixels or plugs transected and captured and non-transected skin pixels or plugs prior to transection, under an embodiment. At the donor site, the pixelated skin resection sites are closed with the application of Flexan® sheeting.

The guide plate and scalpet device are also used to generate skin defects at the recipient site. The skin defects are configured to receive the skin pixels harvested or captured at the donor site. The guide plate used at the recipient site can be the same guide plate used at the donor site, or can be different with a different pattern or configuration of perforations.

The skin pixels or plugs deposited onto the adherent substrate during the transection can next be transferred to the skin defect site (recipient site) where they are applied as a pixelated skin graft at a recipient skin defect site. The adherent substrate has an elastic recoil property that enables closer alignment of the skin pixels or plugs within the skin graft. The incised skin pixels can be applied from the adherent substrate directly to the skin defects at the recipient site. Application of the incised skin pixels at the recipient site includes aligning the incised skin pixels with the skin defects, and inserting the incised skin pixels into corresponding skin defects at the recipient site.

Figure 10A:
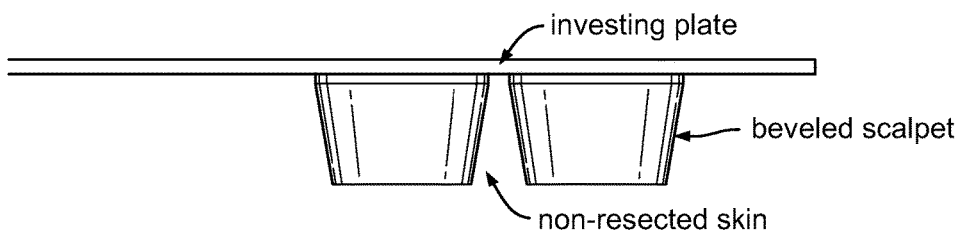
FIG. 10A is a side view of a portion of the pixel array showing scalpets secured onto an investing plate, under an embodiment.
Figure 10B:
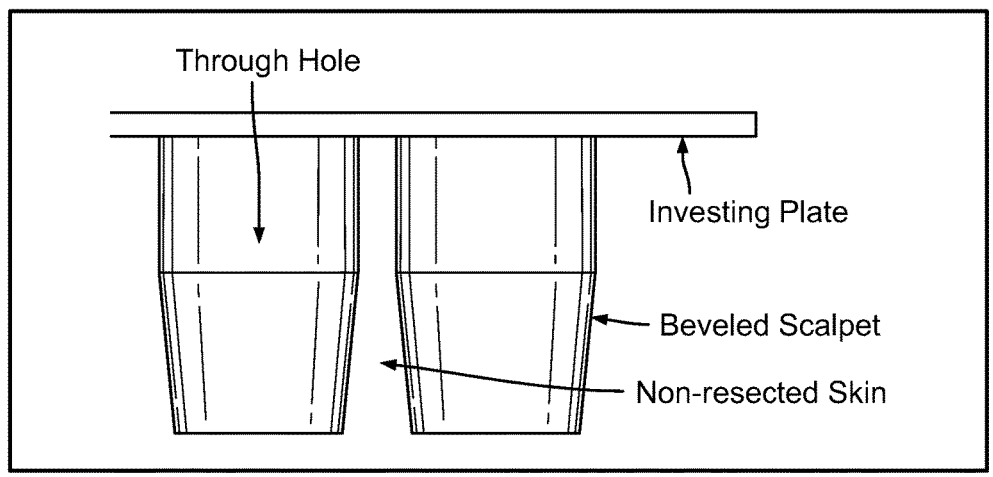
FIG. 10B is a side view of a portion of the pixel array showing scalpets secured onto an investing plate, under an alternative embodiment.
Figure 10C:
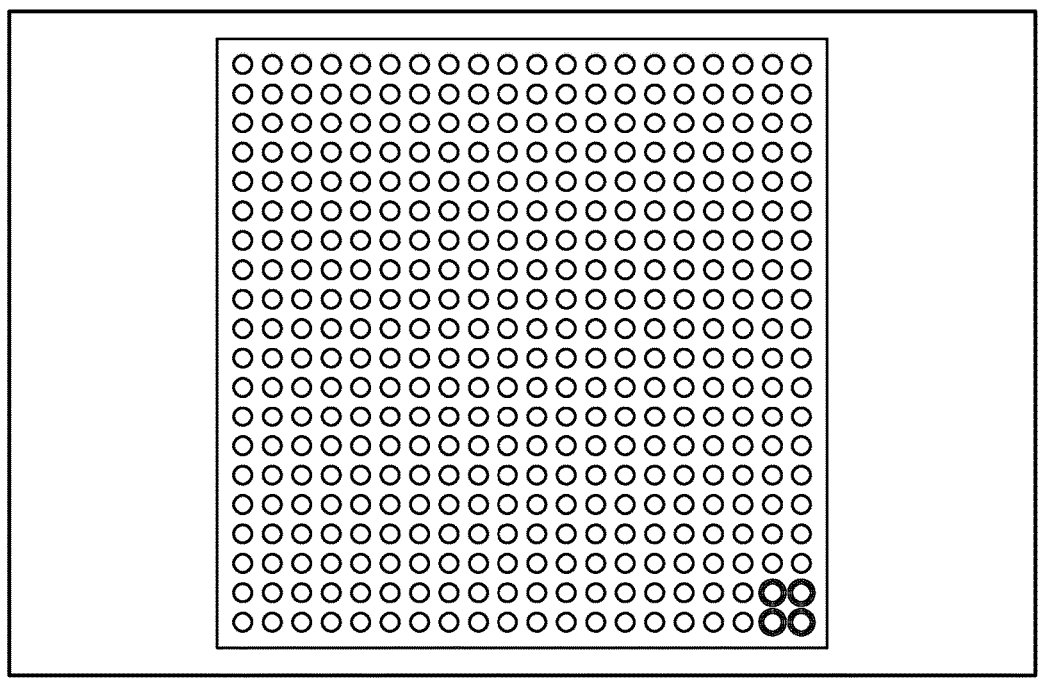
FIG. 10C is a top view of the scalpet plate, under an embodiment.
Figure 10D:
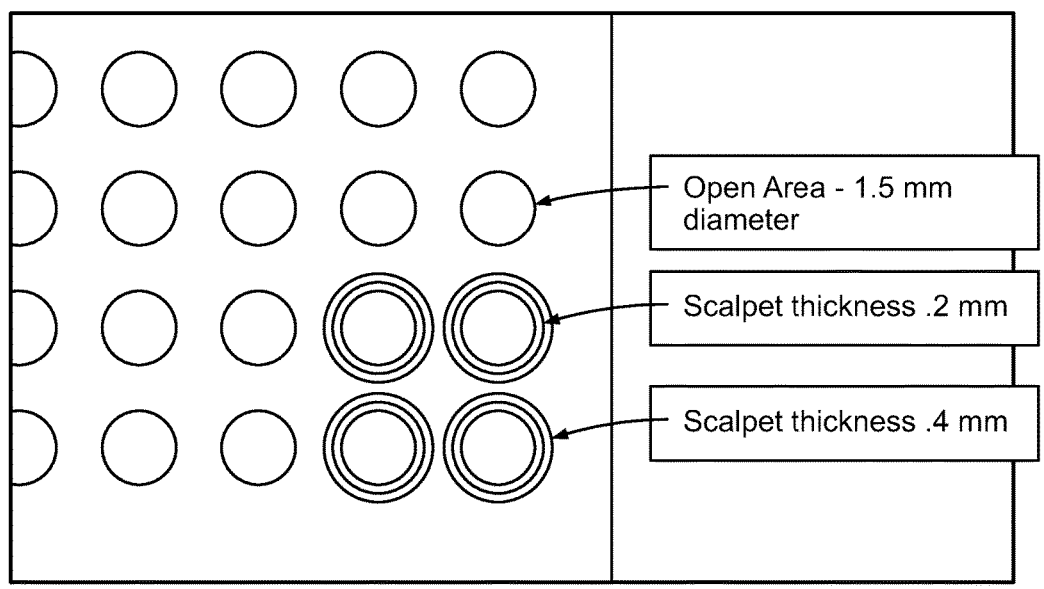
FIG. 10D is a close view of a portion of the scalpet plate, under an embodiment.

The pixel array medical devices of an embodiment include a Pixel Array Dermatome (PAD). The PAD comprises a flat array of relatively small circular scalpets that are secured onto a substrate (e.g., investing plate), and the scalpets in combination with the substrate are referred to herein as a scalpet array, pixel array, or scalpet plate. FIG. 10A is a side view of a portion of the pixel array showing scalpets secured onto an investing plate, under an embodiment. FIG. 10B is a side view of a portion of the pixel array showing scalpets secured onto an investing plate, under an alternative embodiment. FIG. 10C is a top view of the scalpet plate, under an embodiment. FIG. 10D is a close view of a portion of the scalpet plate, under an embodiment. The scalpet plate is applied directly to the skin surface. One or more scalpets of the scalpet array include one or more of a pointed surface, a needle, and a needle including multiple points.

Embodiments of the pixel array medical devices and methods include use of a harvest pattern instead of the guide plate. The harvest pattern comprises indicators or markers on a skin surface on at least one of the donor site and the recipient site, but is not so limited. The markers include any compound that may be applied directly to the skin to mark an area of the skin. The harvest pattern is positioned at a donor site, and the scalpet array of the device is aligned with or according to the harvest pattern at the donor site. The skin pixels are incised at the donor site with the scalpet array as described herein. The recipient site is prepared by positioning the harvest pattern at the recipient site. The harvest pattern used at the recipient site can be the same harvest pattern used at the donor site, or can be different with a different pattern or configuration of markers. The skin defects are generated, and the incised skin pixels are applied at the recipient site as described herein. Alternatively, the guide plate of an embodiment is used in applying the harvest pattern, but the embodiment is not so limited.

To leverage established surgical instrumentation, the array of an embodiment is used in conjunction with or as a modification to a drum dermatome, for example a Padget dermatome or a Reese dermatome, but is not so limited. The Padget drum dermatome referenced herein was originally developed by Dr. Earl Padget in the 1930s, and continues to be widely utilized for skin grafting by plastic surgeons throughout the world. The Reese modification of the Padget dermatome was subsequently developed to better calibrate the thickness of the harvested skin graft. The drum dermatome of an embodiment is a single use (per procedure) disposable, but is not so limited.

Figure 11A:
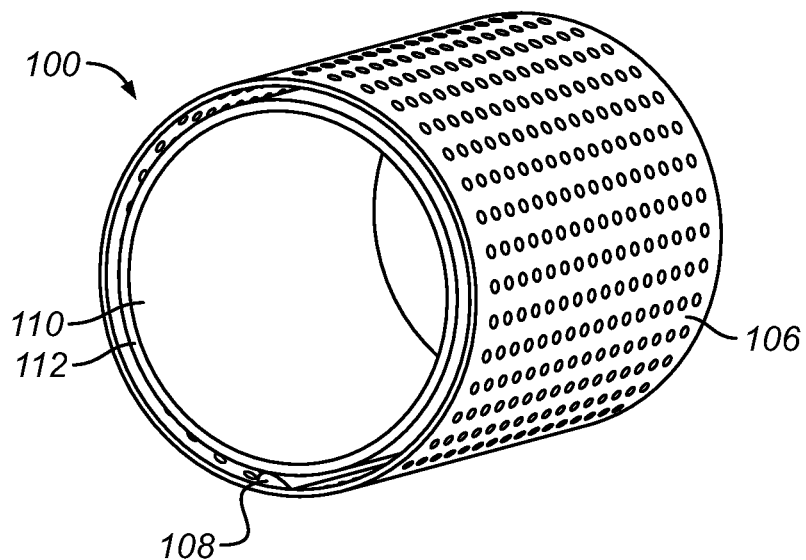
FIG. 11A shows an example of rolling pixel drum, under an embodiment.
Figure 11B:
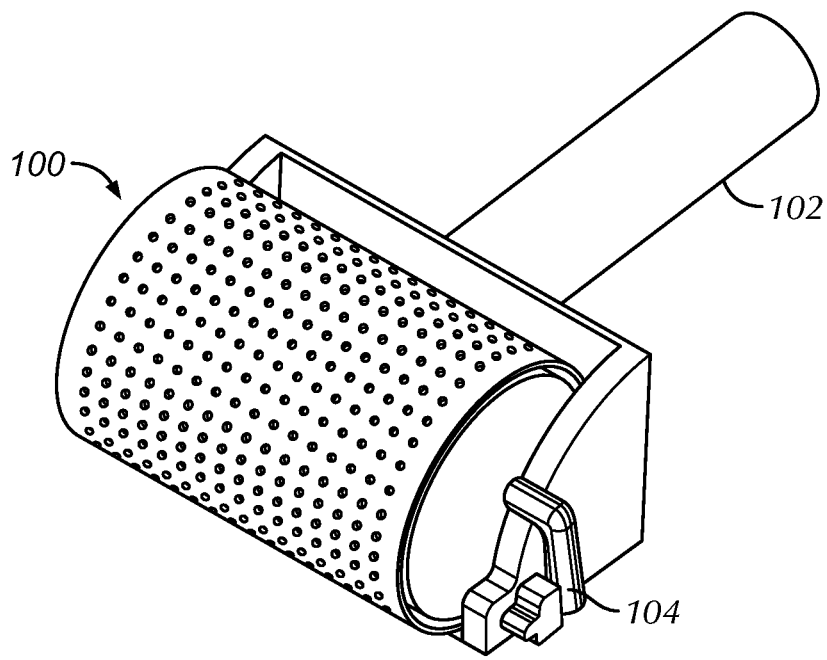
FIG. 11B shows an example of a rolling pixel drum assembled on a handle, under an embodiment.
Figure 11C:
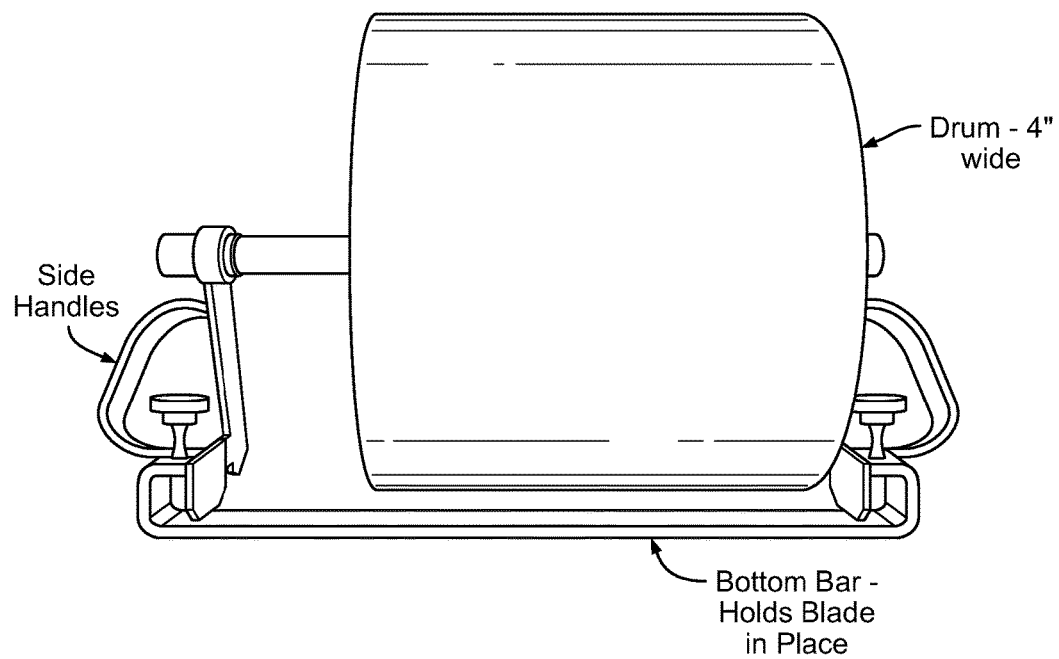
FIG. 11C depicts a drum dermatome for use with the scalpet plate, under an embodiment.

Generally, FIG. 11A shows an example of a rolling pixel drum 100, under an embodiment. FIG. 11B shows an example of a rolling pixel drum 100 assembled on a handle, under an embodiment. More specifically, FIG. 11C depicts a drum dermatome for use with the scalpet plate, under an embodiment.

Generally, as with all pixel devices described herein, the geometry of the pixel drum 100 can be a variety of shapes without limitation e.g., circular, semicircular, elliptical, square, flat, or rectangular. In some embodiments, the pixel drum 100 is supported by an axel/handle assembly 102 and rotated around a drum rotational component 104 powered by, e.g., an electric motor. In some embodiments, the pixel drum 100 can be placed on stand (not shown) when not in use, wherein the stand can also function as a battery recharger for the powered rotational component of the drum or the powered component of the syringe plunger. In some embodiments, a vacuum (not shown) can be applied to the skin surface of the pixel drum 100 and outriggers (not shown) can be deployed for tracking and stability of the pixel drum 100.

In some embodiments, the pixel drum 100 incorporates an array of scalpets 106 on the surface of the drum 100 to create small multiple (e.g., 0.5-1.5 mm) circular incisions referred to herein as skin plugs. In some embodiments, the border geometry of the scalpets can be designed to reduce pin cushioning ("trap door") while creating the skin plugs. The perimeter of each skin plug can also be lengthened by the scalpets to, for a non-limiting example, a, semicircular, elliptical, or square-shaped skin plug instead of a circular-shaped skin plug. In some embodiments, the length of the scalpets 106 may vary depending upon the thickness of the skin area selected by the surgeon for skin grafting purposes, i.e., partial thickness or full thickness.

When the drum 100 is applied to a skin surface, a blade 108 placed internal of the drum 100 transects the base of each skin plug created by the array of scalpets, wherein the internal blade 108 is connected to the central drum axel/handle assembly 102 and/or connected to outriggers attached to the central axel assembly 102. In some alternative embodiments, the internal blade 108 is not connected to the drum axel assembly 102 where the base of the incisions of skin is transected. In some embodiments, the internal blade 108 of the pixel drum 100 may oscillate either manually or be powered by an electric motor. Depending upon the density of the circular scalpets on the drum, a variable percentage of skin (e.g., 20%, 30%, 40%, etc.) can be transected within an area of excessive skin laxity.

In some embodiments, an added pixel drum harvester 112 is placed inside the drum 100 to perform a skin grafting operation by harvesting and aligning the transected/pixilated skin incisions/plugs (pixel graft) from tissue of a pixel donor onto an adherent membrane 110 lined in the interior of the pixel drum 100. A narrow space is created between the array of scalpets 106 and the adherent membrane 110 for the internal blade 108.

In an embodiment, the blade 108 is placed external to the drum 100 and the scalpet array 106 where the base of the incised circular skin plugs is transected. In another embodiment, the external blade 108 is connected to the drum axel assembly 102 when the base of the incisions of skin is transected. In an alternative embodiment, the external blade 108 is not connected to the drum axel assembly 102 when the base of the incisions of skin is transected. The adherent membrane 110 that extracts and aligns the transected skin segments is subsequently placed over a skin defect site of a patient. The blade 108 (either internal or external) can be a fenestrated layer of blade aligned to the scalpet array 106, but is not so limited.

The conformable adherent membrane 110 of an embodiment can be semi-porous to allow for drainage at a recipient skin defect when the membrane with the aligned transected skin segments is extracted from the drum and applied as a skin graft. The adherent semi-porous drum membrane 110 can also have an elastic recoil property to bring the transected/pixilated skin plugs together for grafting onto the skin defect site of the recipient, i.e., the margins of each skin plug can be brought closer together as a more uniform sheet after the adherent membrane with pixilated grafts extracted from the drum 100. Alternatively, the adherent semi-porous drum membrane 110 can be expandable to cover a large surface area of the skin defect site of the recipient. In some embodiments, a sheet of adhesive backer 111 can be applied between the adherent membrane 110 and the drum harvester 112. The drum array of scalpets 106, blade 108, and adherent membrane 110 can be assembled together as a sleeve onto a preexisting drum 100, as described in detail herein.

The internal drum harvester 112 of the pixel drum 110 of an embodiment is disposable and replaceable. Limit and/or control the use of the disposable components can be accomplished by means that includes but is not limited to electronic, EPROM, mechanical, durability. The electronic and/or mechanical records and/or limits of number of drum rotations for the disposable drum as well as the time of use for the disposable drum can be recorded, controlled and/or limited either electronically or mechanically.

During the harvesting portion of the procedure with a drum dermatome, the PAD scalpet array is applied directly to the skin surface. To circumferentially incise the skin pixels, the drum dermatome is positioned over the scalpet array to apply a load onto the subjacent skin surface. With a continuing load, the incised skin pixels are extruded through the holes of the scalpet array and captured onto an adherent membrane on the drum dermatome. The cutting outrigger blade of the dermatome (positioned over the scalpet array) transects the base of extruded skin pixels. The membrane and the pixelated skin composite are then removed from the dermatome drum, to be directly applied to the recipient skin defect as a skin graft.

Figure 12A:
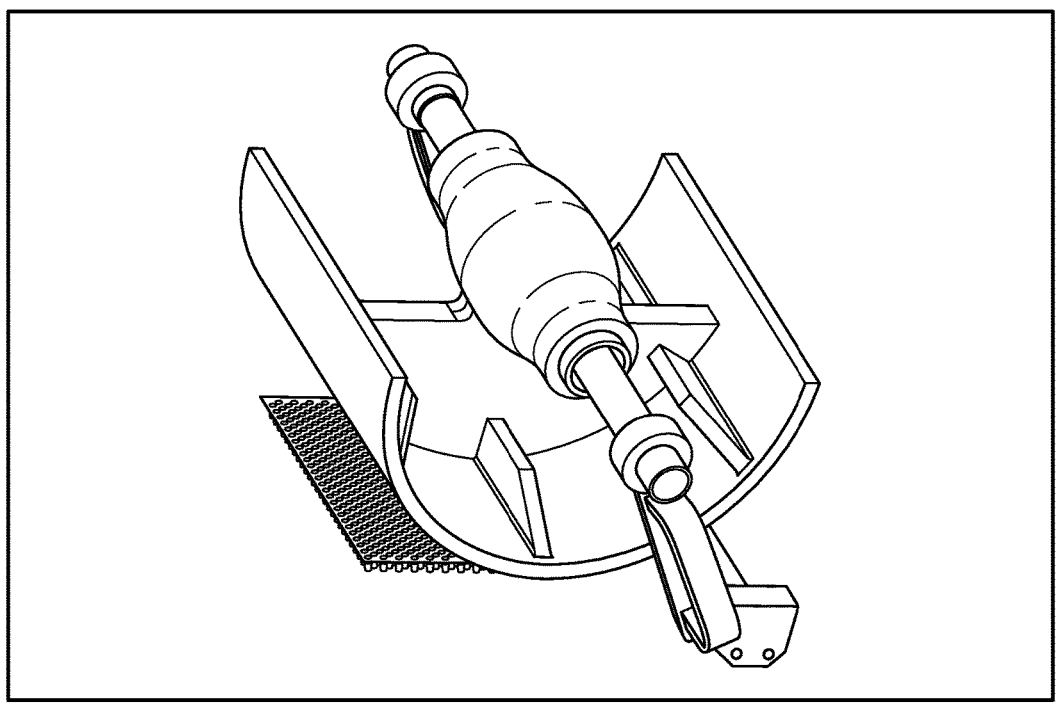
FIG. 12A shows the drum dermatome positioned over the scalpet plate, under an embodiment.
Figure 12B:
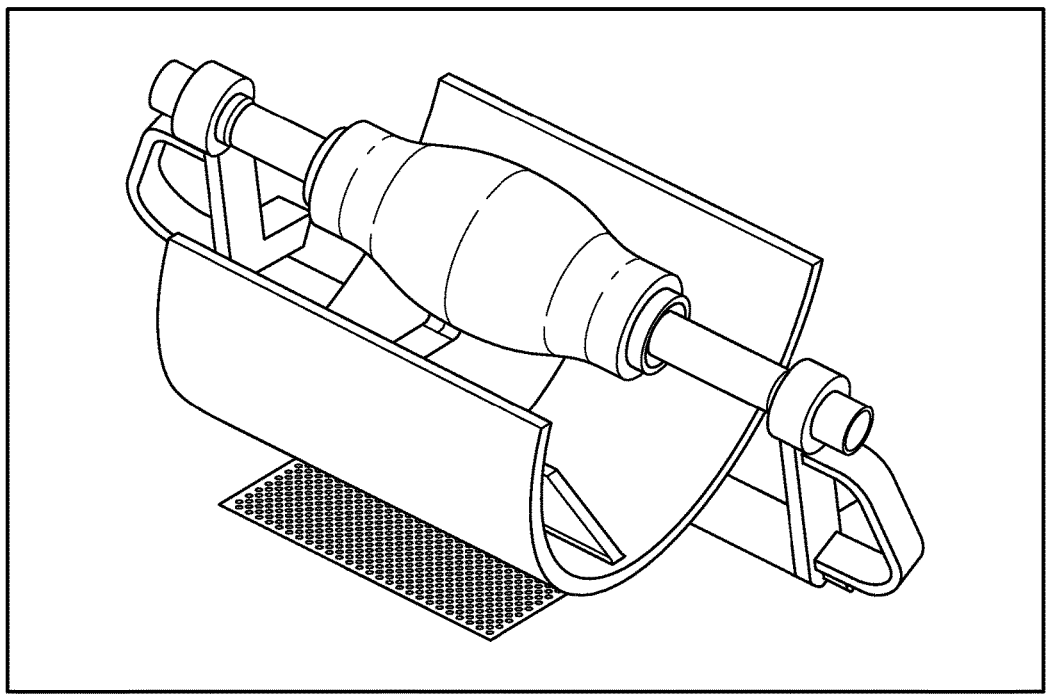
FIG. 12B is an alternative view of the drum dermatome positioned over the scalpet plate, under an embodiment.

With reference to FIG. 11C, an embodiment includes a drum dermatome for use with the scalpet plate, as described herein. More particularly, FIG. 12A shows the drum dermatome positioned over the scalpet plate, under an embodiment. FIG. 12B is an alternative view of the drum dermatome positioned over the scalpet plate, under an embodiment. The cutting outrigger blade of the drum dermatome is positioned on top of the scalpet array where the extruded skin plugs will be transected at their base.

Figure 13A:
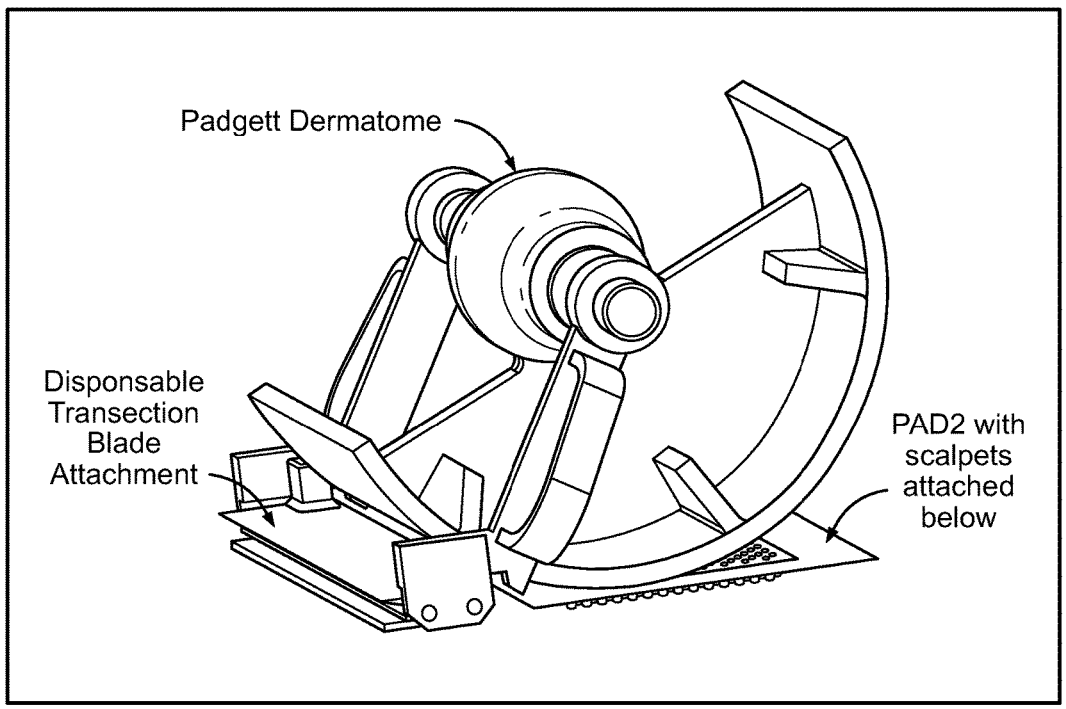
FIG. 13A is an isometric view of application of the drum dermatome (e.g., Padgett dermatome) over the scalpet plate, where the adhesive membrane is applied to the drum of the dermatome before rolling it over the investing plate, under an embodiment.
Figure 13B:
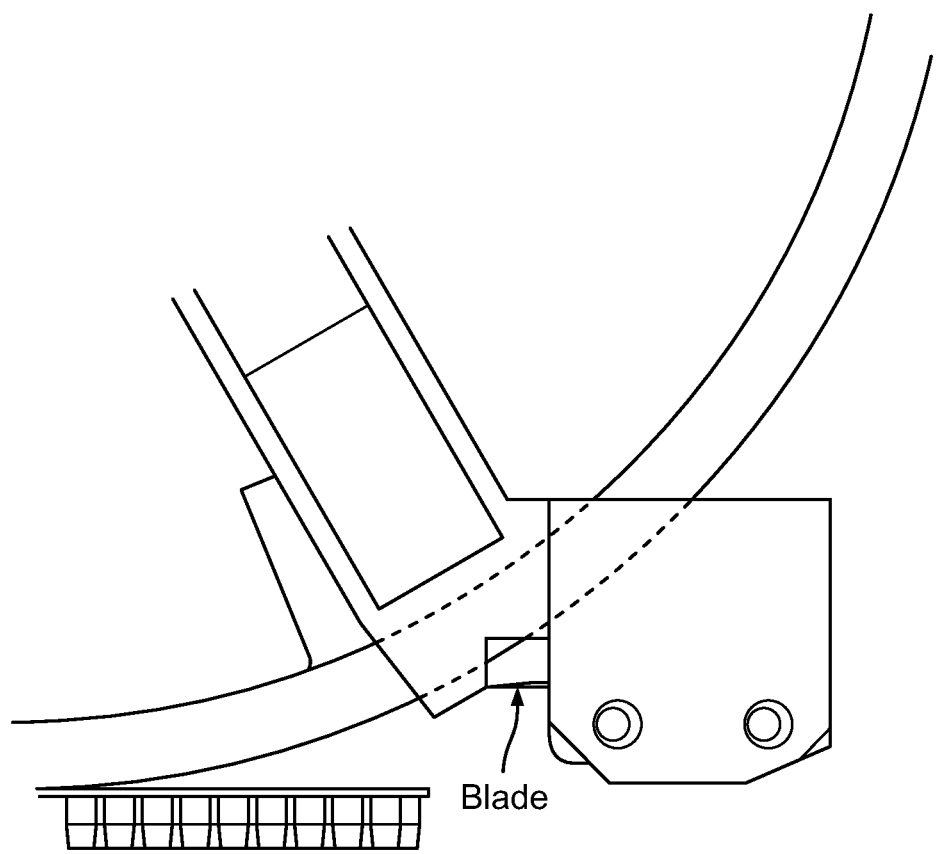
FIG. 13B is a side view of a portion of the drum dermatome showing a blade position relative to the scalpet plate, under an embodiment.
Figure 13C:
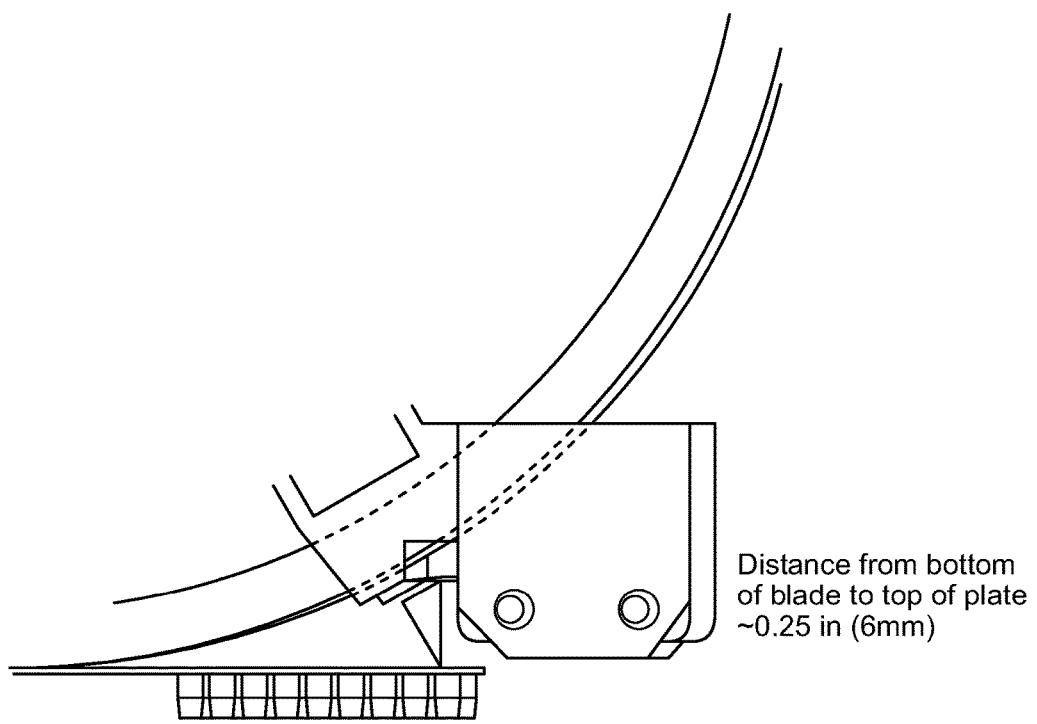
FIG. 13C is a side view of the portion of the drum dermatome showing a different blade position relative to the scalpet plate, under an embodiment.
Figure 13D:
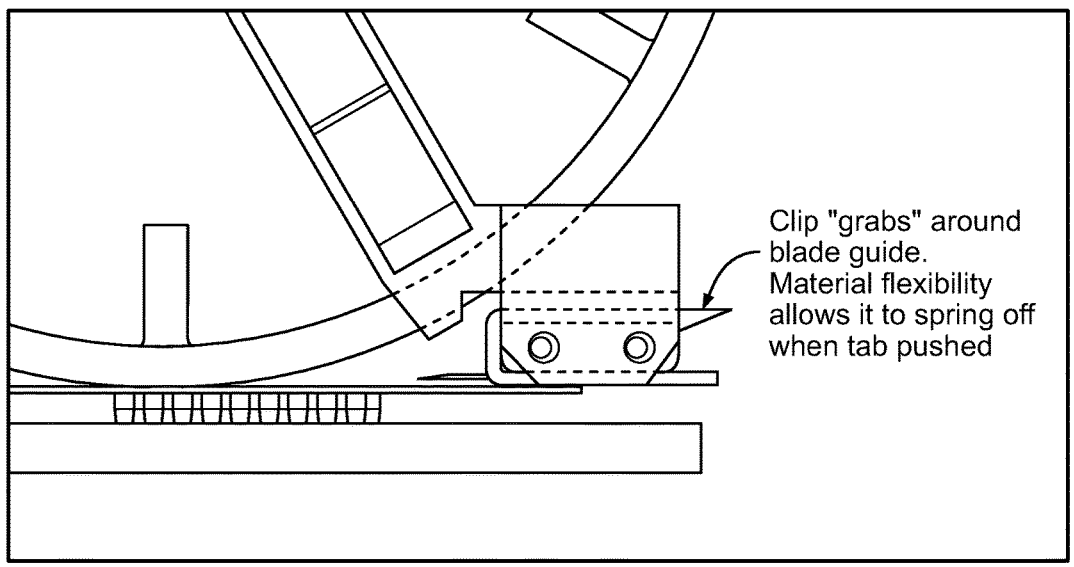
FIG. 13D is a side view of the drum dermatome with another blade position relative to the scalpet plate, under an embodiment.
Figure 13E:
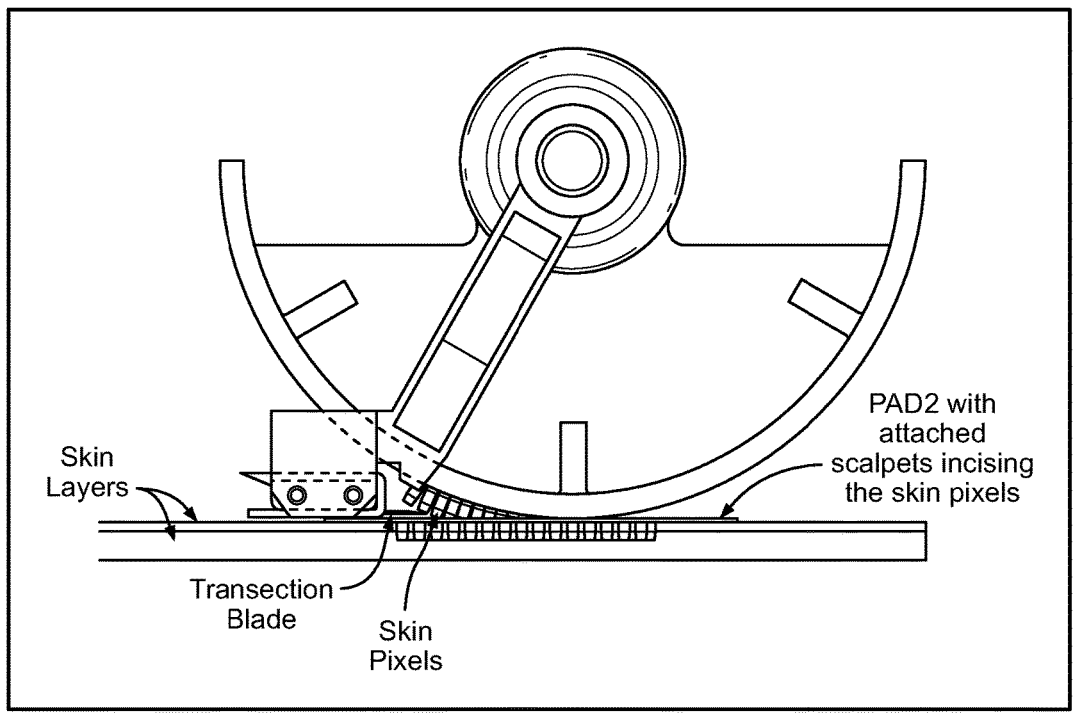
FIG. 13E is a side view of the drum dermatome with the transection blade clip showing transection of skin pixels by the blade clip, under an embodiment.
Figure 13F:
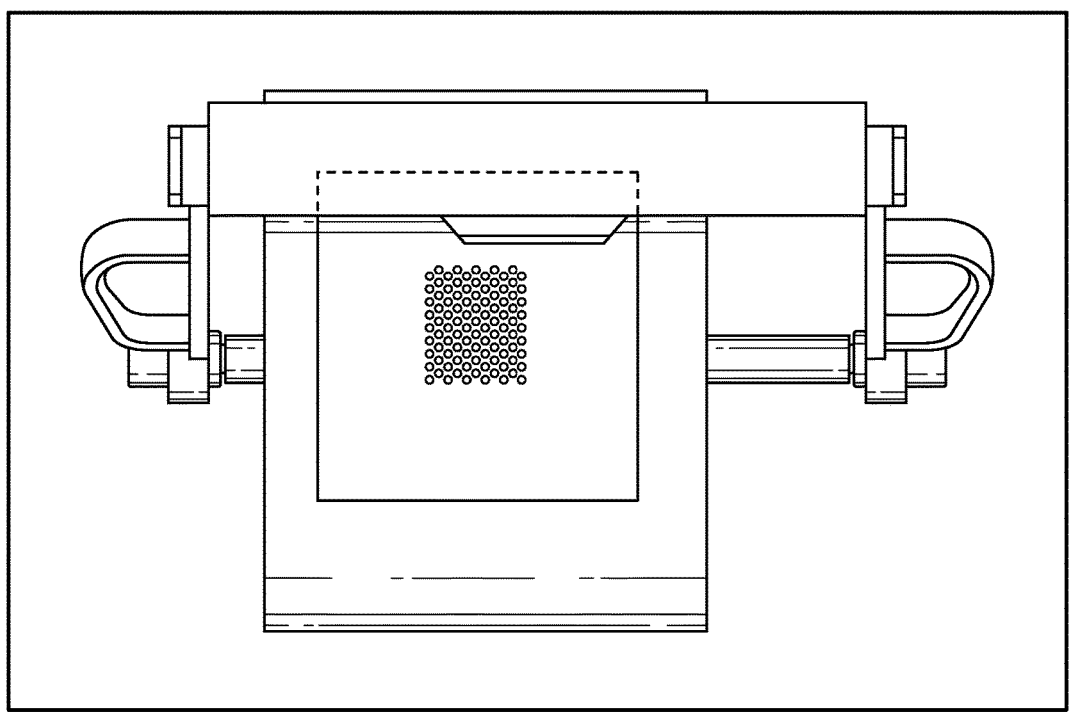
FIG. 13F is a bottom view of the drum dermatome along with the scalpet plate, under an embodiment.
Figure 13G:
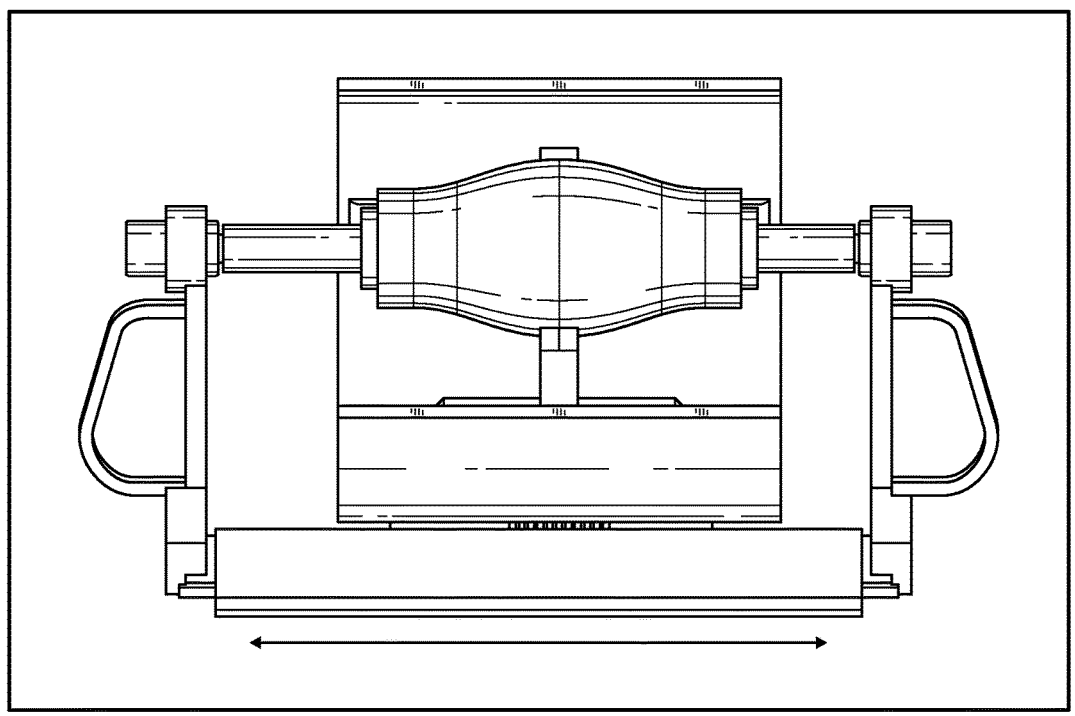
FIG. 13G is a front view of the drum dermatome along with the scalpet plate, under an embodiment.
Figure 13H:
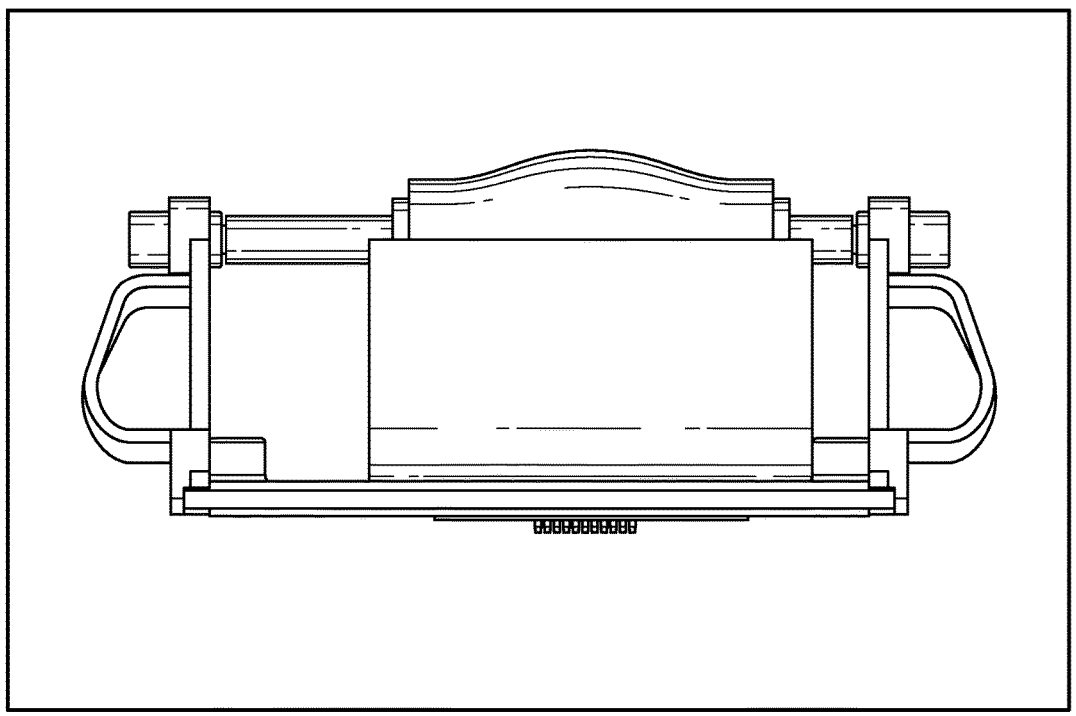
FIG. 13H is a back view of the drum dermatome along with the scalpet plate, under an embodiment.

FIG. 13A is an isometric view of application of the drum dermatome (e.g., Padgett dermatome) over the scalpet plate, where the adhesive membrane is applied to the drum of the dermatome before rolling it over the investing plate, under an embodiment. FIG. 13B is a side view of a portion of the drum dermatome showing a blade position relative to the scalpet plate, under an embodiment. FIG. 13C is a side view of the portion of the drum dermatome showing a different blade position relative to the scalpet plate, under an embodiment. FIG. 13D is a side view of the drum dermatome with another blade position relative to the scalpet plate, under an embodiment. FIG. 13E is a side view of the drum dermatome with the transection blade clip showing transection of skin pixels by the blade clip, under an embodiment. FIG. 13F is a bottom view of the drum dermatome along with the scalpet plate, under an embodiment. FIG. 13G is a front view of the drum dermatome along with the scalpet plate, under an embodiment. FIG. 13H is a back view of the drum dermatome along with the scalpet plate, under an embodiment.

Depending upon the clinical application, the disposable adherent membrane of the drum dermatome can be used to deposit/dispose of resected lax skin or harvest/align a pixilated skin graft.

Embodiments described herein also include a Pixel Onlay Sleeve (POS) for use with the dermatomes, for example the Padget dermatomes and Reese dermatomes.

Figure 14A:
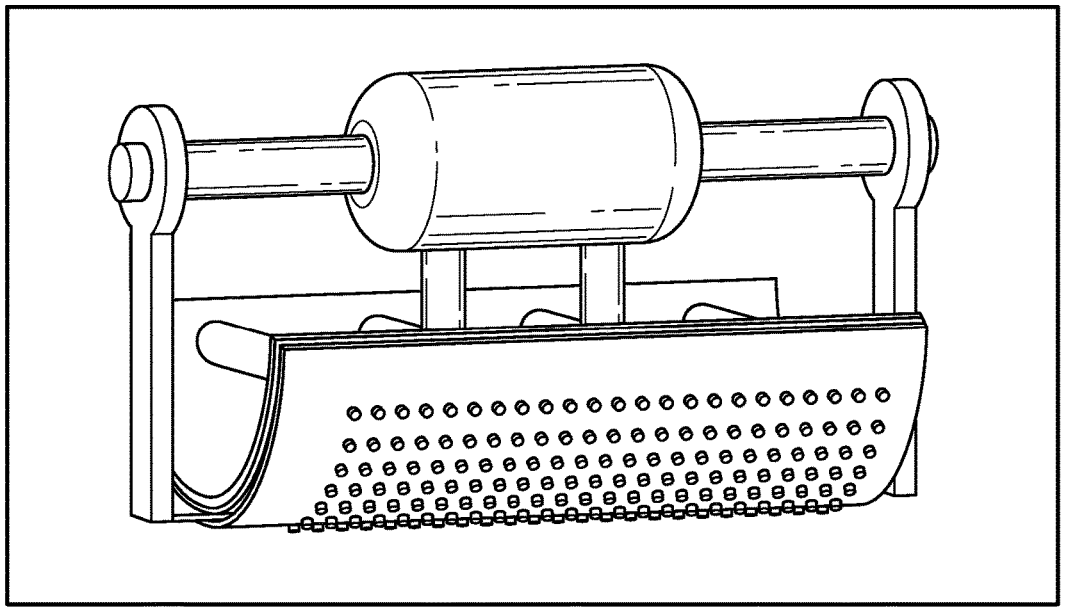
FIG. 14A shows an assembled view of the dermatome with the Pixel Onlay Sleeve (POS), under an embodiment.
Figure 14B:
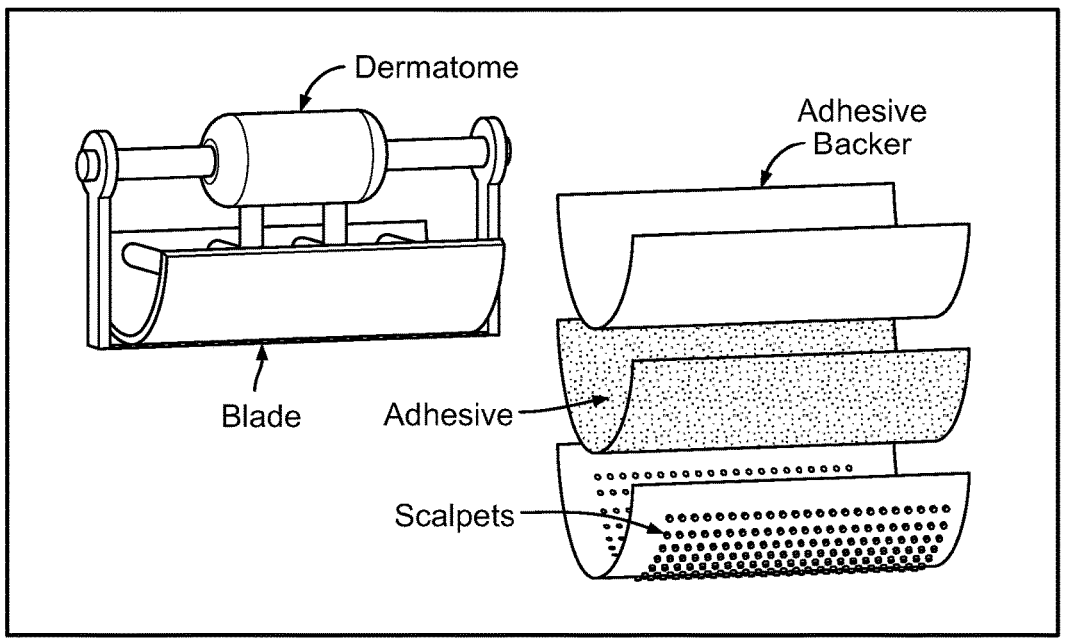
FIG. 14B is an exploded view of the dermatome with the Pixel Onlay Sleeve (POS), under an embodiment.
Figure 14C:
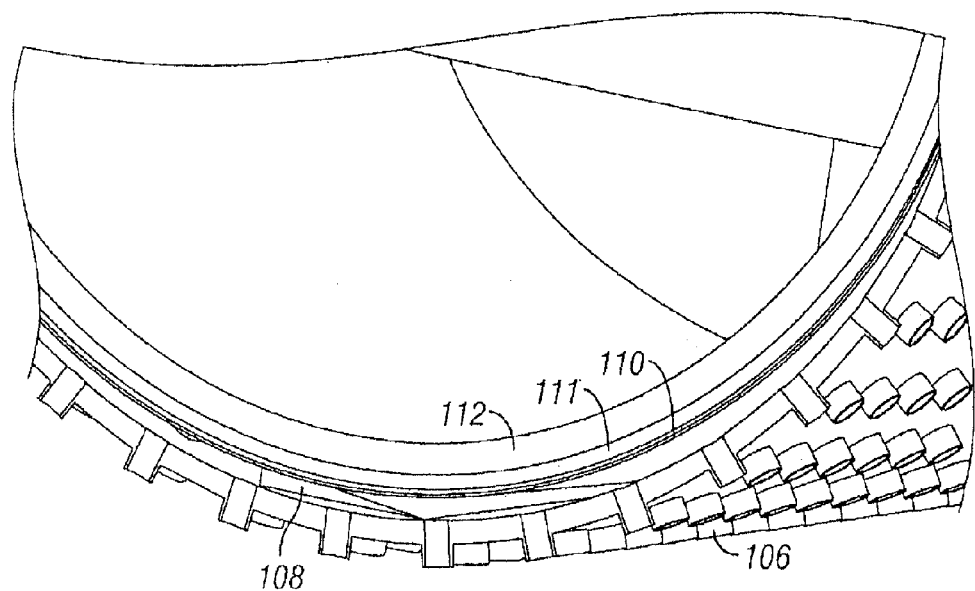
FIG. 14C shows a portion of the dermatome with the Pixel Onlay Sleeve (POS), under an embodiment.

FIG. 14A shows an assembled view of the dermatome with the Pixel Onlay Sleeve (POS), under an embodiment. The POS comprises the dermatome and blade incorporated with an adhesive backer, adhesive, and a scalpet array. The adhesive backer, adhesive, and scalpet array are integral to the device, but are not so limited. FIG. 14B is an exploded view of the dermatome with the Pixel Onlay Sleeve (POS), under an embodiment. FIG. 14C shows a portion of the dermatome with the Pixel Onlay Sleeve (POS), under an embodiment.

The POS, also referred to herein as the "sleeve," provides a disposable drum dermatome onlay for the fractional resection of redundant lax skin and the fractional skin grafting of skin defects. The onlay sleeve is used in conjunction with either the Padget and Reese dermatomes as a single use disposable component. The POS of an embodiment is a three-sided slip-on disposable sleeve that slips onto a drum dermatome. The device comprises an adherent membrane and a scalpet drum array with an internal transection blade. The transection blade of an embodiment includes a single-sided cutting surface that sweeps across the internal surface of the scalpet drum array.

In an alternative blade embodiment, a fenestrated cutting layer covers the internal surface of the scalpet array. Each fenestration with its cutting surface is aligned with each individual scalpet. Instead of sweeping motion to transect the base of the skin plugs, the fenestrated cutting layer oscillates over the scalpet drum array. A narrow space between the adherent membrane and the scalpet array is created for excursion of the blade. For multiple harvesting during a skin grafting procedure, an insertion slot for additional adherent membranes is provided. The protective layer over the adherent membrane is pealed away insitu with an elongated extraction tab that is pulled from an extraction slot on the opposite side of the sleeve assembly. As with other pixel device embodiments, the adherent membrane is semi-porous for drainage at the recipient skin defect site. To morph the pixilated skin graft into a more continuous sheet, the membrane may also have an elastic recoil property to provide closer alignment of the skin plugs within the skin graft.

Figure 15A:
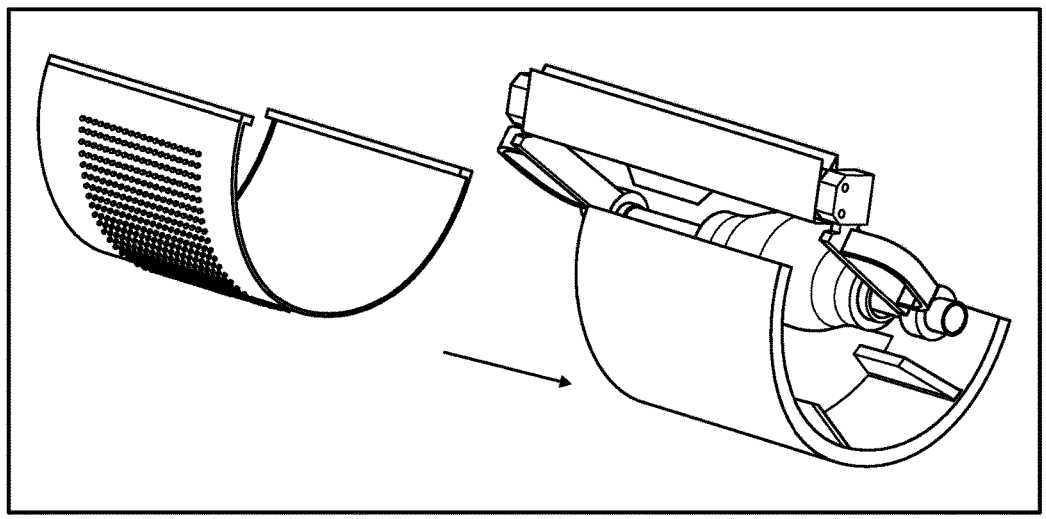
FIG. 15A shows the Slip-On PAD being slid onto a Padgett Drum Dermatome, under an embodiment.
Figure 15B:
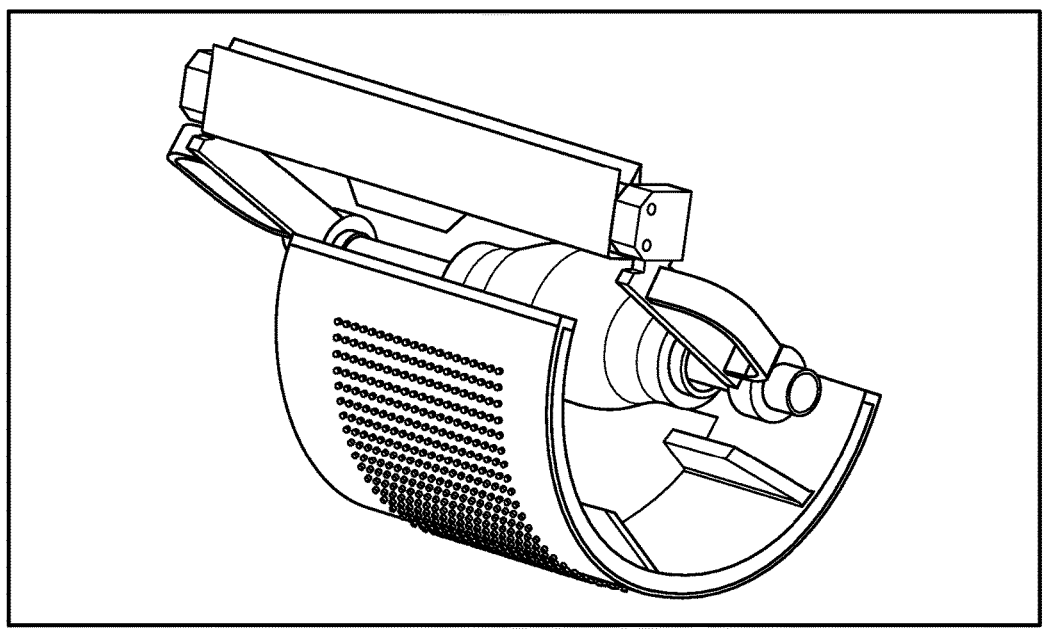
FIG. 15B shows an assembled view of the Slip-On PAD installed over the Padgett Drum Dermatome, under an embodiment.

Embodiments described herein include a Slip-On PAD that is configured as a single-use disposable device with either the Padgett or Reese dermatomes. FIG. 15A shows the Slip-On PAD being slid onto a Padgett Drum Dermatome, under an embodiment. FIG. 15B shows an assembled view of the Slip-On PAD installed over the Padgett Drum Dermatome, under an embodiment.

Figure 16A:
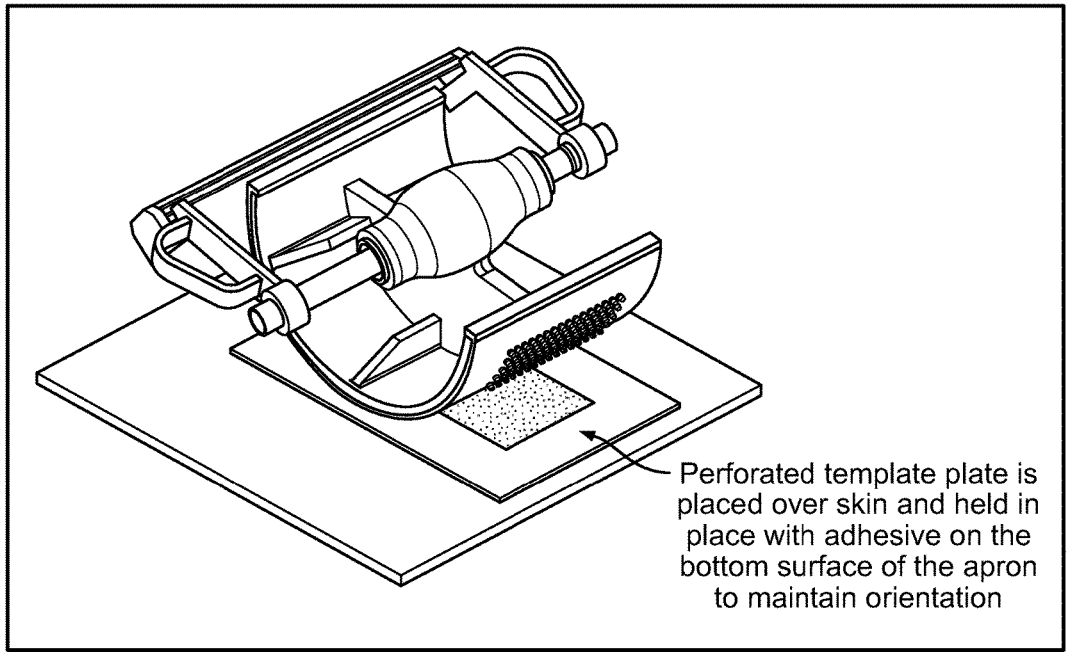
FIG. 16A shows the Slip-On PAD installed over a Padgett Drum Dermatome and used with a perforated template or guide plate, under an embodiment.

The Slip-on PAD of an embodiment is used (optionally) in combination with a perforated guide plate. FIG. 16A shows the Slip-On PAD installed over a Padgett Drum Dermatome and used with a perforated template or guide plate, under an embodiment. The perforated guide plate is placed over the target skin site and held in place with adhesive on the bottom surface of the apron to maintain orientation. The Padgett Dermatome with Slip-On PAD is rolled over the perforated guide plate on the skin.

Figure 16B:
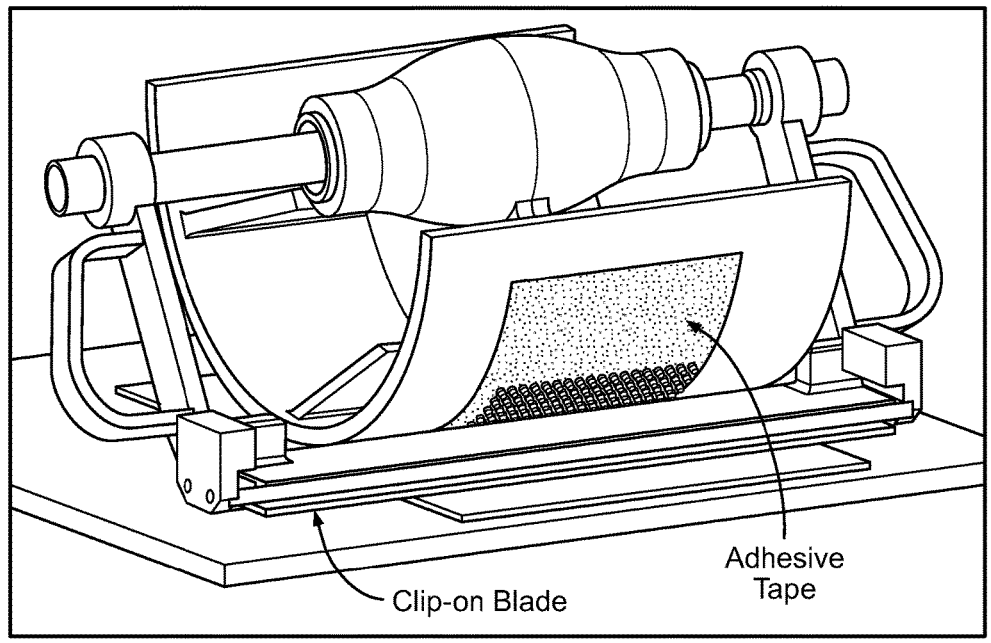
FIG. 16B shows skin pixel harvesting with a Padgett Drum Dermatome and installed Slip-On PAD, under an embodiment.

FIG. 16B shows skin pixel harvesting with a Padgett Drum Dermatome and installed Slip-On PAD, under an embodiment. For skin pixel harvesting, the Slip-On PAD is removed, adhesive tape is applied over the drum of the Padgett dermatome, and the clip-on blade is installed on the outrigger arm of the dermatome, which then is used to transect the base of the skin pixels. The Slip-on PAD of an embodiment is also used (optionally) with standard surgical instrumentation such as a ribbon retractor to protect the adjacent skin of the donor site.

Embodiments of the pixel instruments described herein include a Pixel Drum Dermatome (PD2) that is a single use disposable instrument or device. The PD2 comprises a cylinder or rolling/rotating drum coupled to a handle, and the cylinder includes a Scalpet Drum Array. An internal blade is interlocked to the drum axle/handle assembly and/or interlocked to outriggers attached to the central axle. As with the PAD and the POS described herein, small multiple pixilated resections of skin are performed directly in the region of skin laxity, thereby enhancing skin tightening with minimal visible scarring.

Figure 17A:
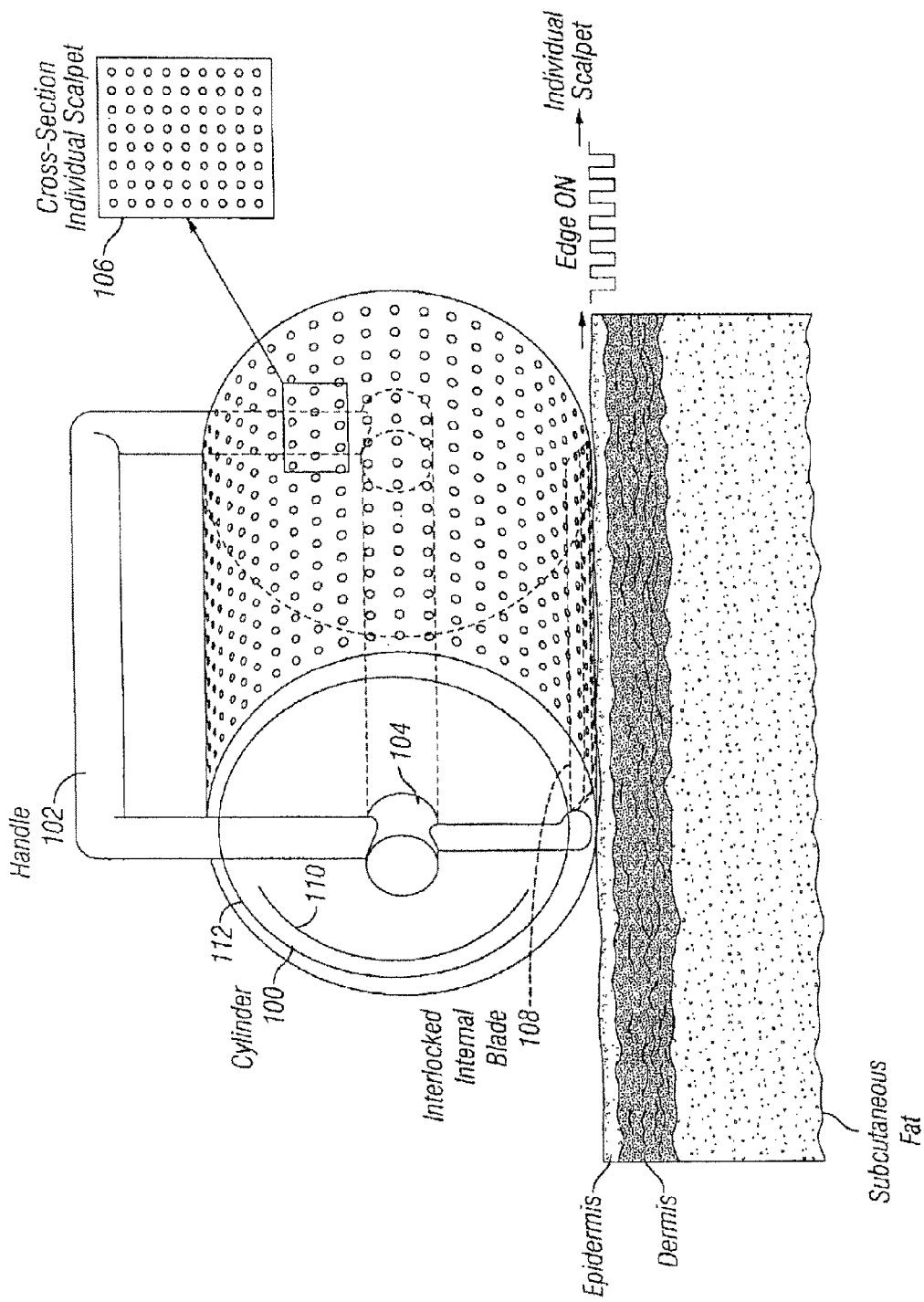
FIG. 17A shows an example of a Pixel Drum Dermatome being applied to a target site of the skin surface, under an embodiment.
Figure 17B:
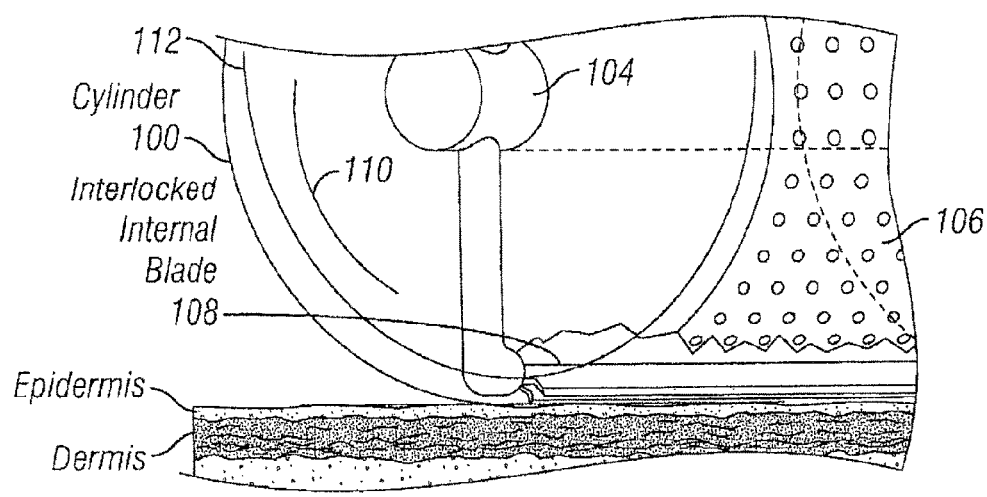
FIG. 17B shows an alternative view of a portion of the Pixel Drum Dermatome being applied to a target site of the skin surface, under an embodiment.

FIG. 17A shows an example of a Pixel Drum Dermatome being applied to a target site of the skin surface, under an embodiment. FIG. 17B shows an alternative view of a portion of the Pixel Drum Dermatome being applied to a target site of the skin surface, under an embodiment.

The PD2 device applies a full rolling/rotating drum to the skin surface where multiple small (e.g., 1.5 mm) circular incisions are created at the target site with a "Scalpet Drum Array". The base of each skin plug is then transected with an internal blade that is interlocked to the central drum axel/handle assembly and/or interlocked to outriggers attached to the central axel. Depending upon the density of the circular scalpets on the drum, a variable percentage of skin can be resected. The PD2 enables portions (e.g., 20%, 30%, 40%, etc.) of the skin's surface area to be resected without visible scarring in an area of excessive skin laxity, but the embodiment is not so limited.

Another alternative embodiment of the pixel instruments presented herein is the Pixel Drum Harvester (PDH). Similar to the Pixel Drum Dermatome, an added internal drum harvests and aligns the pixilated resections of skin onto an adherent membrane that is then placed over a recipient skin defect site of the patient. The conformable adherent membrane is semi-porous to allow for drainage at a recipient skin defect when the membrane with the aligned resected skin segments is extracted from the drum and applied as a skin graft. An elastic recoil property of the membrane allows closer approximation of the pixilated skin segments, partially converting the pixilated skin graft to a sheet graft at the recipient site.

The pixel array medical systems, instruments or devices, and methods described herein evoke or enable cellular and/or extracellular responses that are obligatory to the clinical outcomes achieved. For the pixel dermatomes, a physical reduction of the skin surface area occurs due to the pixilated resection of skin, i.e., creation of the skin plugs. In addition, a subsequent tightening of the skin results due to the delayed wound healing response. Each pixilated resection initiates an obligate wound healing sequence in multiple phases as described in detail herein.

The first phase of this sequence is the inflammatory phase in which degranulation of mast cells release histamine into the "wound". Histamine release may evoke dilatation of the capillary bed and increase vessel permeability into the extracellular space. This initial wound healing response occurs within the first day and will be evident as erythema on the skin's surface.

The second phase (of Fibroplasia) commences within three to four days of "wounding". During this phase, there is migration and mitotic multiplication of fibroblasts. Fibroplasia of the wound includes the deposition of neocollagen and the myofibroblastic contraction of the wound.

Histologically, the deposition of neocollagen can be identified microscopically as compaction and thickening of the dermis. Although this is a static process, the tensile strength of the wound significantly increases. The other feature of Fibroplasia is a dynamic physical process that results in a multi-dimensional contraction of the wound. This component feature of Fibroplasia is due to the active cellular contraction of myofibroblasts. Morphologically, myoblastic contraction of the wound will be visualized as a two dimensional tightening of the skin surface. Overall, the effect of Fibroplasia is dermal contraction along with the deposition of a static supporting scaffolding of neocollagen with a tightened framework. The clinical effect is seen as a delayed tightening of skin with smoothing of skin texture over several months. The clinical endpoint is generally a more youthful appearing skin envelope of the treatment area.

A third and final phase of the delayed wound healing response is maturation. During this phase there is a strengthening and remodeling of the treatment area due to an increased cross-linkage of the collagen fibril matrix (of the dermis). This final stage commences within six to twelve months after "wounding" and may extend for at least one to two years. Small pixilated resections of skin should preserve the normal dermal architecture during this delayed wound healing process without the creation of an evident scar that typically occurs with a larger surgical resection of skin. Lastly, there is a related stimulation and rejuvenation of the epidermis from the release of epidermal growth hormone. The delayed wound healing response can be evoked, with scar collagen deposition, within tissues (such as muscle or fat) with minimal pre-existing collagen matrix.

Other than tightening skin for aesthetic purposes, the pixel array medical systems, instruments or devices, and methods described herein may have additional medically related applications. In some embodiments, the pixel array devices can transect a variable portion of any soft tissue structure without resorting to a standard surgical resection. More specifically, the reduction of an actinic damaged area of skin via the pixel array devices should reduce the incidence of skin cancer. For the treatment of sleep apnea and snoring, a pixilated mucosal reduction (soft palate, base of the tongue and lateral pharyngeal walls) via the pixel array devices would reduce the significant morbidity associated with more standard surgical procedures. For birth injuries of the vaginal vault, pixilated skin and vaginal mucosal resection via the pixel array devices would reestablish normal pre-partum geometry and function without resorting to an A&P resection. Related female stress incontinence could also be corrected in a similar fashion.

The pixel array dermatome (PAD) of an embodiment, also referred to herein as a scalpet device assembly, includes a system or kit comprising a control device, also referred to as a punch impact hand-piece, and a scalpet device, also referred to as a tip device. The scalpet device, which is removeably coupled to the control device, includes an array of scalpets positioned within the scalpet device. The removeable scalpet device of an embodiment is disposable and consequently configured for use during a single procedure, but the embodiment is not so limited.

The PAD includes an apparatus comprising a housing configured to include a scalpet device. The scalpet device includes a substrate and a scalpet array, and the scalpet array includes a plurality of scalpets arranged in a configuration on the substrate. The substrate and the plurality of scalpets are configured to be deployed from the housing and retracted into the housing, and the plurality of scalpets is configured to generate a plurality of incised skin pixels at a target site when deployed. The proximal end of the control device is configured to be hand-held. The housing is configured to be removeably coupled to a receiver that is a component of a control device. The control device includes a proximal end that includes an actuator mechanism, and a distal end that includes the receiver. The control device is configured to be disposable, but alternatively the control device is configured to be at least one of cleaned, disinfected, and sterilized.

The scalpet array is configured to be deployed in response to activation of the actuator mechanism. The scalpet device of an embodiment is configured so the scalpet array is deployed from the scalpet device and retracted back into the scalpet device in response to activation of the actuator mechanism. The scalpet device of an alternative embodiment is configured so the scalpet array is deployed from the scalpet device in response to activation of the actuator mechanism, and retracted back into the scalpet device in response to release of the actuator mechanism.

FIG. 18 shows a side perspective view of the PAD assembly, under an embodiment. The PAD assembly of this embodiment includes a control device configured to be hand-held, with an actuator or trigger and the scalpet device comprising the scalpet array. The control device is reusable, but alternative embodiments include a disposable control device. The scalpet array of an embodiment is configured to create or generate an array of incisions (e.g., 1.5 mm, 2 mm, 3 mm, etc.) as described in detail herein. The scalpet device of an embodiment includes a spring-loaded array of scalpets configured to incise the skin as described in detail herein, but the embodiments are not so limited.

FIG. 19A shows a top perspective view of the scalpet device for use with the PAD assembly, under an embodiment. FIG. 19B shows a bottom perspective view of the scalpet device for use with the PAD assembly, under an embodiment. The scalpet device comprises a housing configured to house a substrate that is coupled to or includes a plunger. The housing is configured so that a proximal end of the plunger protrudes through a top surface of the housing. The housing is configured to be removeably coupled to the control device, and a length of the plunger is configured to protrude a distance through the top surface to contact the control device and actuator when the scalpet device is coupled to the control device.

The substrate of the scalpet device is configured to retain numerous scalpets that form the scalpet array. The scalpet array comprises a pre-specified number of scalpets as appropriate to the procedure in which the scalpet device assembly is used. The scalpet device includes at least one spring mechanism configured to provide a downward, or impact or punching, force in response to activation of the scalpet array device, and this force assists generation of incisions (pixelated skin resection sites) by the scalpet array. Alternatively, the spring mechanism can be configured to provide an upward, or retracting, force to assist in retraction of the scalpet array.

One or more of the scalpet device and the control device of an embodiment includes an encryption system (e.g., EPROM, etc.). The encryption system is configured to prevent illicit use and pirating of the scalpet devices and/or control devices, but is not so limited.

During a procedure, the scalpet device assembly is applied one time to a target area or, alternative, applied serially within a designated target treatment area of skin laxity. The pixelated skin resection sites within the treatment area are then closed with the application of Flexan sheeting, as described in detail herein, and directed closure of these pixelated resections is performed in a direction that provides the greatest aesthetic correction of the treatment site.

The PAD device of an alternative embodiment includes a vacuum component or system for removing incised skin pixels. FIG. 20 shows a side view of the punch impact device including a vacuum component, under an embodiment. The PAD of this example includes a vacuum system or component within the control device to suction evacuate the incised skin pixels, but is not so limited. The vacuum component is removeably coupled to the PAD device, and its use is optional. The vacuum component is coupled to and configured to generate a low-pressure zone within or adjacent to one or more of the housing, the scalpet device, the scalpet array, and the control device. The low-pressure zone is configured to evacuate the incised skin pixels.

The PAD device of another alternative embodiment includes a radio frequency (RF) component or system for generating skin pixels. The RF component is coupled to and configured to provide or couple energy within or adjacent to one or more of the housing, the scalpet device, the scalpet array, and the control device. The RF component is removeably coupled to the PAD device, and its use is optional. The energy provided by the RF component includes one or more of thermal energy, vibrational energy, rotational energy, and acoustic energy, to name a few.

The PAD device of yet another alternative embodiment includes a vacuum component or system and an RF component or system. The PAD of this embodiment includes a vacuum system or component within the handpiece to suction evacuate the incised skin pixels. The vacuum component is removeably coupled to the PAD device, and its use is optional. The vacuum component is coupled to and configured to generate a low-pressure zone within or adjacent to one or more of the housing, the scalpet device, the scalpet array, and the control device. The low-pressure zone is configured to evacuate the incised skin pixels. Additionally, the PAD device includes an RF component coupled to and configured to provide or couple energy within or adjacent to one or more of the housing, the scalpet device, the scalpet array, and the control device. The RF component is removeably coupled to the PAD device, and its use is optional. The energy provided by the RF component includes one or more of thermal energy, vibrational energy, rotational energy, and acoustic energy, to name a few.

As one particular example, the PAD of an embodiment includes an electrosurgical generator configured to more effectively incise donor skin or skin plugs with minimal thermo-conductive damage to the adjacent skin. For this reason, the RF generator operates using relatively high power levels with relatively short duty cycles, for example. The RF generator is configured to supply one or more of a powered impactor component configured to provide additional compressive force for cutting, cycling impactors, vibratory impactors, and an ultrasonic transducer.

The PAD with RF of this example also includes a vacuum component, as described herein. The vacuum component of this embodiment is configured to apply a vacuum that pulls the skin up towards the scalpets (e.g., into the lumen of the scalpets, etc.) to stabilize and promote the RF mediated incision of the skin within the fractional resection field, but is not so limited. One or more of the RF generator and the vacuum appliance is coupled to be under the control of a processor running a software application. Additionally, the PAD of this embodiment can be used with the guide plate as described in detail herein, but is not so limited.

In addition to fractional incision at a donor site, fractional skin grafting includes the harvesting and deposition of skin plugs (e.g., onto an adherent membrane, etc.) for transfer to a recipient site. As with fractional skin resection, the use of a duty-driven RF cutting edge on an array of scalpets facilitates incising donor skin plugs. The base of the incised scalpets is then transected and harvested as described in detail herein.

The timing of the vacuum assisted component is processor controlled to provide a prescribed sequence with the RF duty cycle. With software control, different variations are possible to provide the optimal sequence of combined RF cutting with vacuum assistance. Without limitation, these include an initial period of vacuum prior to the RF duty cycle. Subsequent to the RF duty cycle, a period during the sequence of an embodiment includes suction evacuation of the incised skin plugs.

Other potential control sequences of the PAD include without limitation simultaneous duty cycles of RF and vacuum assistance. Alternatively, a control sequence of an embodiment includes pulsing or cycling of the RF duty cycle within the sequence and/or with variations of RF power or the use of generators at different RF frequencies.

Another alternative control sequence includes a designated RF cycle occurring at the depth of the fractional incision. A lower power longer duration RF duty cycle with insulated shaft with an insulated shaft an active cutting tip could generate a thermal-conductive lesion in the deep dermal/subcutaneous tissue interface. The deep thermal lesion would evoke a delayed wound healing sequence that would secondarily tighten the skin without burning of the skin surface.

With software control, different variations are possible to provide the optimal sequence of combined RF cutting and powered mechanical cutting with vacuum assistance. Examples include but are not limited to combinations of powered mechanical cutting with vacuum assistance, RF cutting with powered mechanical cutting and vacuum assistance, RF cutting with vacuum assistance, and RF cutting with vacuum assistance. Examples of combined software controlled duty cycles include but are not limited to precutting vacuum skin stabilization period, RF cutting duty cycle with vacuum skin stabilization period, RF cutting duty cycle with vacuum skin stabilization and powered mechanical cutting period, powered mechanical cutting with vacuum skin stabilization period, post cutting RF duty cycle for thermal conductive heating of the deeper dermal and/or subdermal tissue layer to evoke a wound healing response for skin tightening, and a post cutting vacuum evacuation period for skin tightening.

Figure 21A:
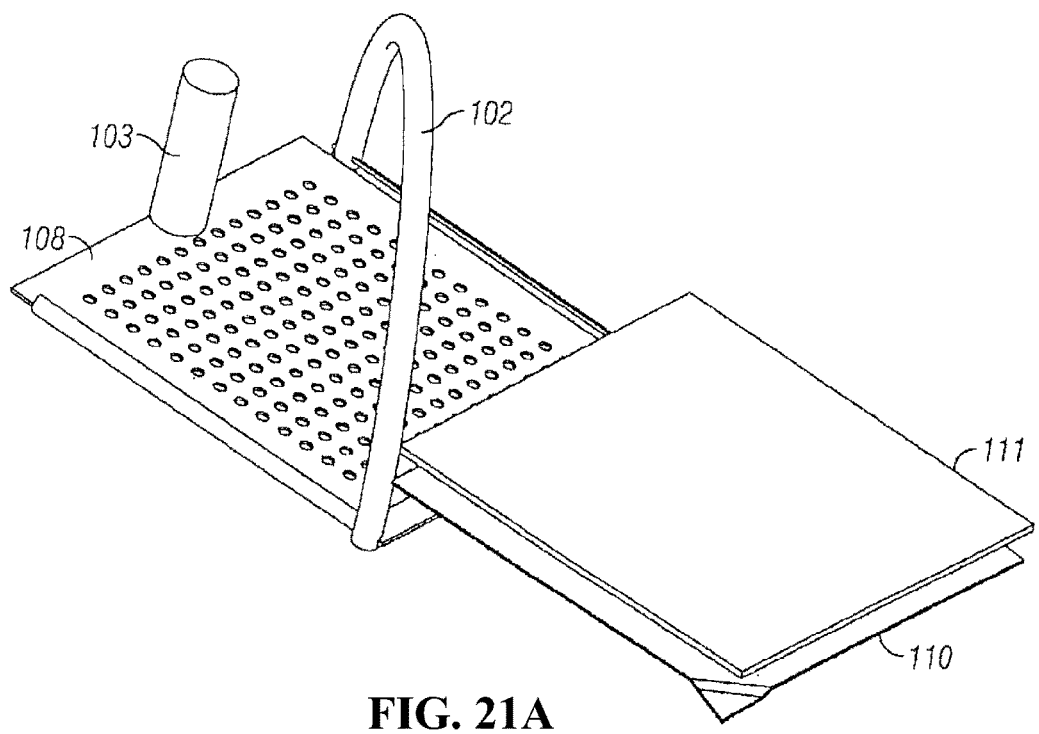
FIG. 21A shows a top view of an oscillating flat scalpet array and blade device, under an embodiment.
Figure 21B:
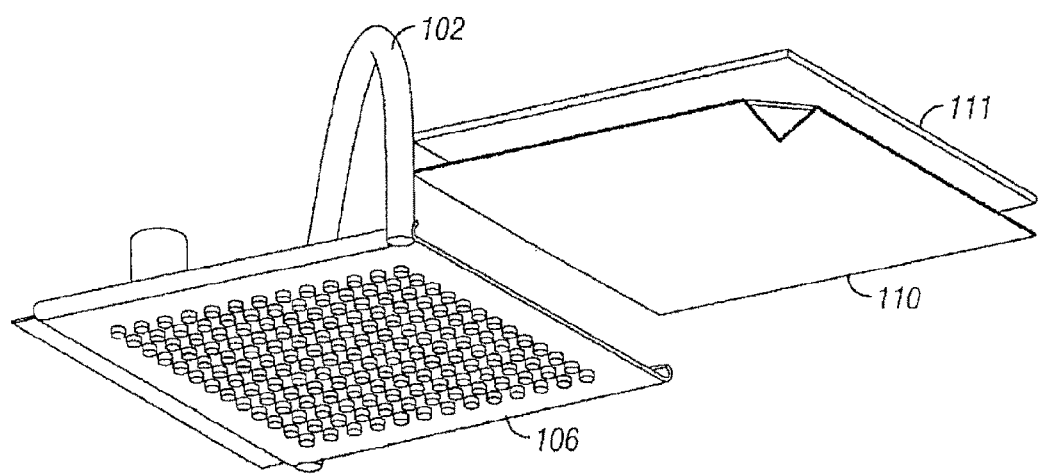
FIG. 21B shows a bottom view of an oscillating flat scalpet array and blade device, under an embodiment.
Figure 21C:
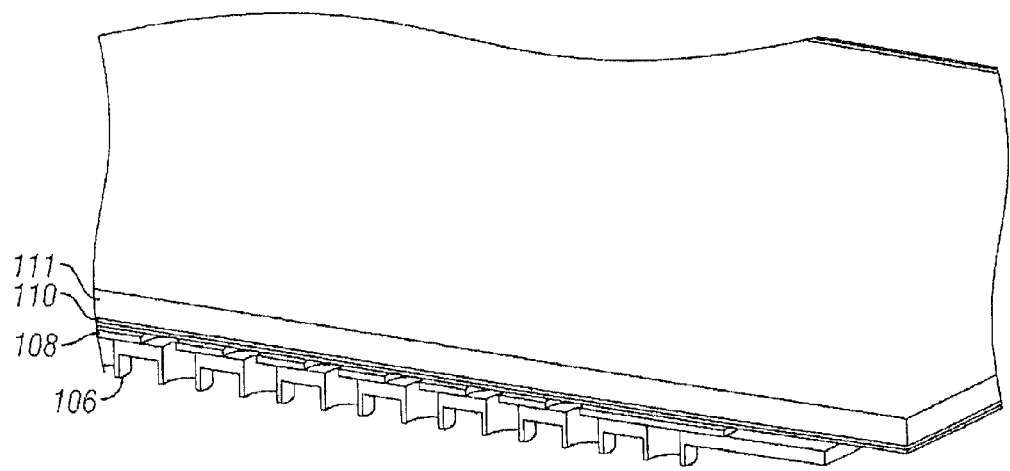
FIG. 21C is a close-up view of the flat array when the array of scalpets, blades, adherent membrane and the adhesive backer are assembled together, under an embodiment.
Figure 21D:
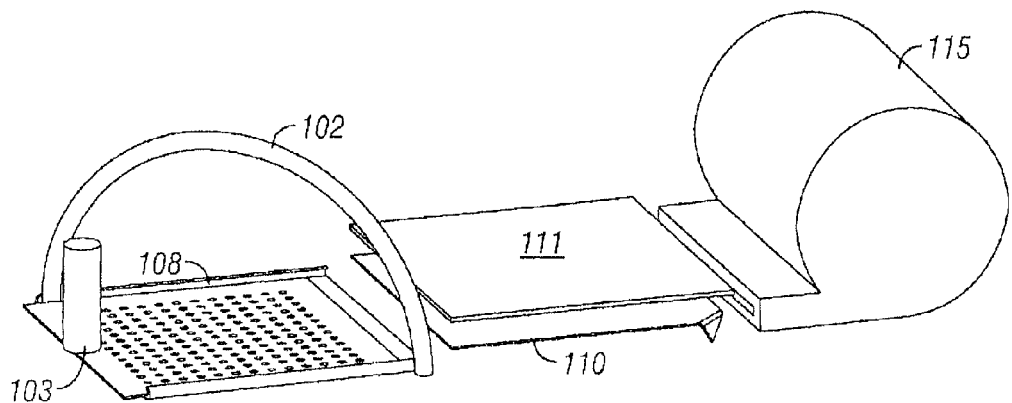
FIG. 21D is a close-up view of the flat array of scalpets with a feeder component, under an embodiment.

Another embodiment of pixel array medical devices described herein includes a device comprising an oscillating flat array of scalpets and blade either powered electrically or deployed manually (unpowered) and used for skin tightening as an alternative to the drum/cylinder described herein. FIG. 21A shows a top view of an oscillating flat scalpet array and blade device, under an embodiment. FIG. 21B shows a bottom view of an oscillating flat scalpet array and blade device, under an embodiment. Blade 108 can be a fenestrated layer of blade aligned to the scalpet array 106. The instrument handle 102 is separated from the blade handle 103 and the adherent membrane 110 can be peeled away from the adhesive backer 111. FIG. 21C is a close-up view of the flat array when the array of scalpets 106, blades 108, adherent membrane 110 and the adhesive backer 111 are assembled together, under an embodiment. As assembled, the flat array of scalpets can be metered to provide a uniform harvest or a uniform resection. In some embodiments, the flat array of scalpets may further include a feeder component 115 for the adherent harvesting membrane 110 and adhesive backer 111. FIG. 21D is a close-up view of the flat array of scalpets with a feeder component 115, under an embodiment.

Figure 22:
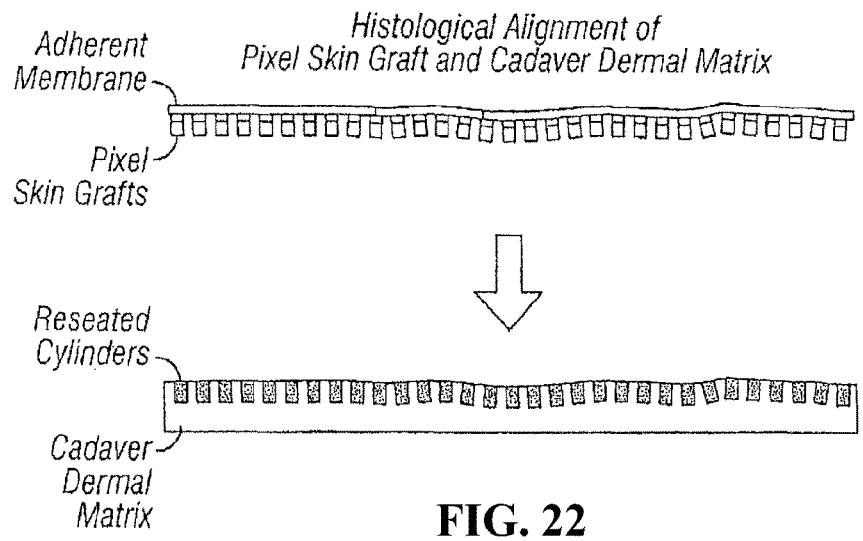
FIG. 22 shows a cadaver dermal matrix cylindrically transected similar in size to the harvested skin pixel grafts, under an embodiment.

In another skin grafting embodiment, the pixel graft is placed onto an irradiated cadaver dermal matrix (not shown). When cultured onto the dermal matrix, a graft of full thickness skin is created for the patient that is immunologically identical to the pixel donor. In embodiments, the cadaver dermal matrix can also be cylindrical transected similar in size to the harvested skin pixel grafts to provide histological alignment of the pixilated graft into the cadaver dermal framework. FIG. 22 shows a cadaver dermal matrix cylindrically transected similar in size to the harvested skin pixel grafts, under an embodiment. In some embodiments, the percentage of harvest of the donor site can be determined in part by the induction of a normal dermal histology at the skin defect site of the recipient, i.e., a normal (smoother) surface topology of the skin graft is facilitated. With either the adherent membrane or the dermal matrix embodiment, the pixel drum harvester includes the ability to harvest a large surface area for grafting with visible scarring of the patient's donor site significantly reduced or eliminated.

In addition to the pixel array medical devices described herein, embodiments include drug delivery devices. For the most part, the parenteral delivery of drugs is still accomplished from an injection with a syringe and needle. To circumvent the negative features of the needle and syringe system, the topical absorption of medication transcutaneously through an occlusive patch was developed. However, both of these drug delivery systems have significant drawbacks. The human aversion to a needle injection has not abated during the nearly two centuries of its use. The variable systemic absorption of either a subcutaneous or intramuscular drug injection reduces drug efficacy and may increase the incidence of adverse patient responses. Depending upon the lipid or aqueous carrier fluid of the drug, the topically applied occlusive patch is plagued with variable absorption across an epidermal barrier. For patients who require local anesthesia over a large surface area of skin, neither the syringe/needle injections nor topical anesthetics are ideal. The syringe/needle "field" injections are often painful and may instill excessive amounts of the local anesthetic that may cause systemic toxicity. Topical anesthetics rarely provide the level of anesthesia required for skin related procedures.

Figure 23:
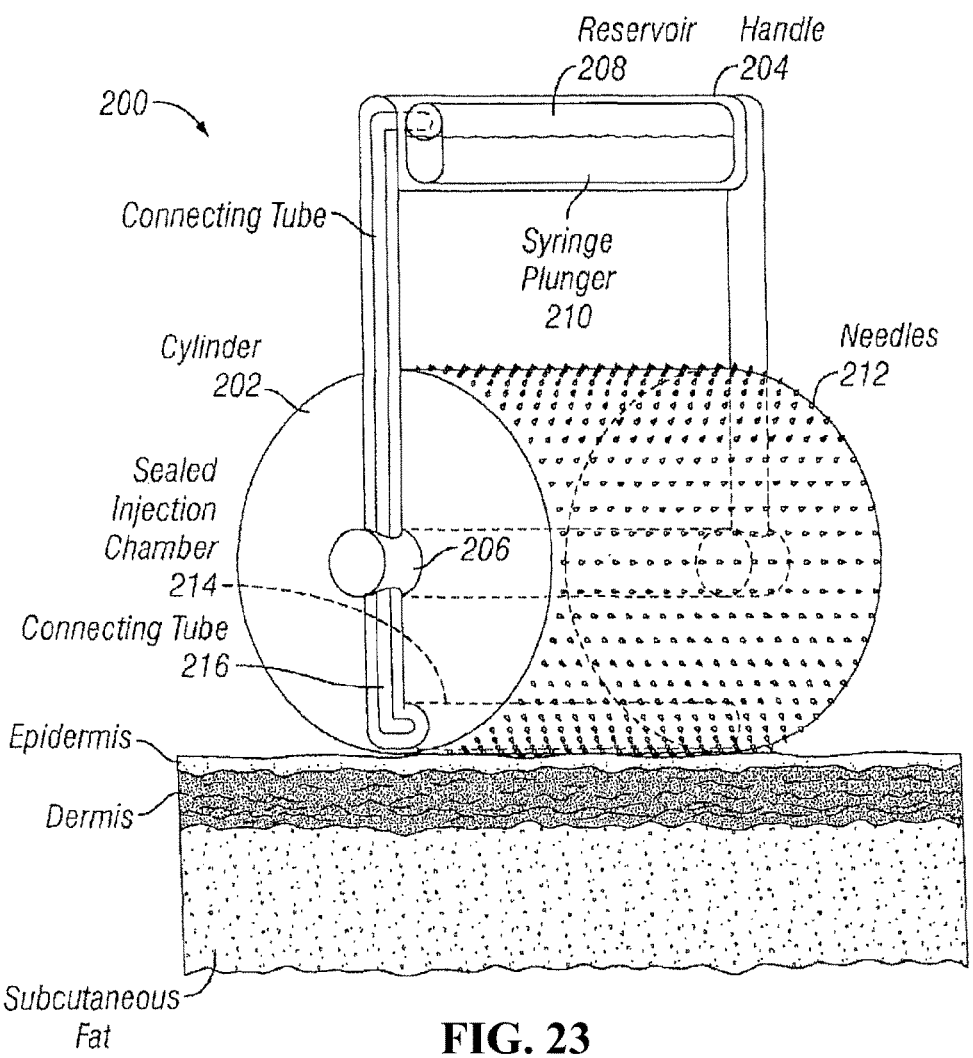
FIG. 23 is a drum array drug delivery device, under an embodiment.

FIG. 23 is a drum array drug delivery device 200, under an embodiment. The drug delivery device 200 successfully addresses the limitations and drawbacks of other drug delivery systems. The device comprises a drum/cylinder 202 supported by an axel/handle assembly 204 and rotated around a drum rotation component 206. The handle assembly 204 of an embodiment further includes a reservoir 208 of drugs to be delivered and a syringe plunger 210. The surface of the drum 202 is covered by an array of needles 212 of uniform length, which provide a uniform intradermal (or subdermal) injection depth with a more controlled volume of the drug injected into the skin of the patient. During operation, the syringe plunger 210 pushes the drug out of the reservoir 208 to be injected into a sealed injection chamber 214 inside the drum 202 via connecting tube 216. The drug is eventually delivered into the patient's skin at a uniform depth when the array of needles 212 is pushed into a patient's skin until the surface of the drum 202 hits the skin. Non-anesthetized skip area is avoided and a more uniform pattern of cutaneous anesthesia is created. The rolling drum application of the drug delivery device 200 also instills the local anesthetic faster with less discomfort to the patient.

Figure 24A:
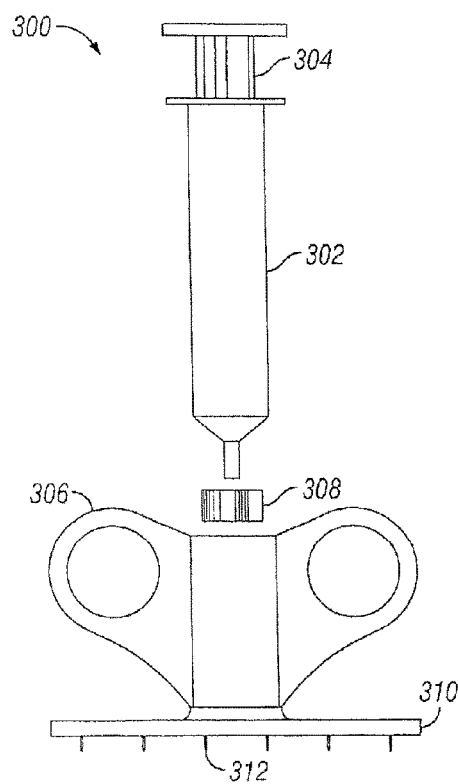
FIG. 24A is a side view of a needle array drug delivery device, under an embodiment.
Figure 24B:
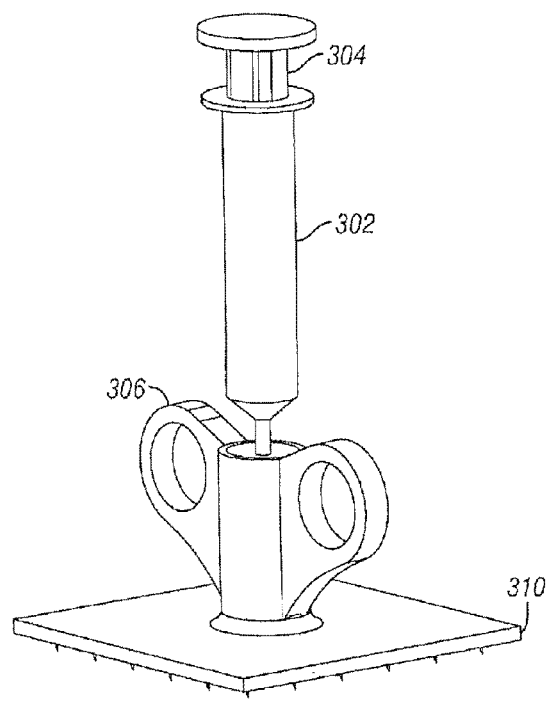
FIG. 24B is an upper isometric view of a needle array drug delivery device, under an embodiment.
Figure 24C:
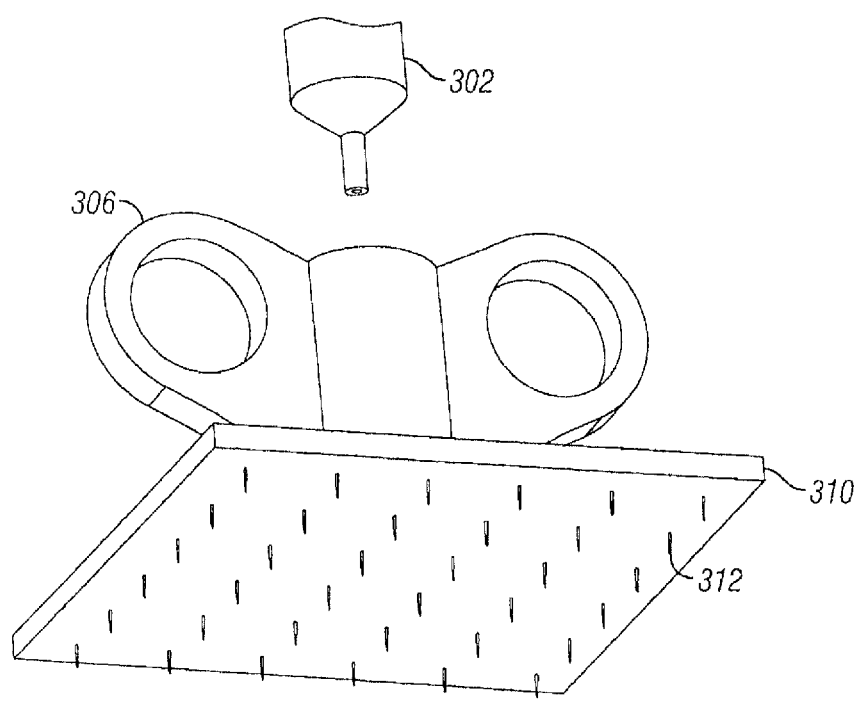
FIG. 24C is a lower isometric view of a needle array drug delivery device, under an embodiment.

FIG. 24A is a side view of a needle array drug delivery device 300, under an embodiment. FIG. 24B is an upper isometric view of a needle array drug delivery device 300, under an embodiment. FIG. 24C is a lower isometric view of a needle array drug delivery device 300, under an embodiment. The drug delivery device 300 comprises a flat array of fine needles 312 of uniform length positioned on manifold 310 can be utilized for drug delivery. In this example embodiment, syringe 302 in which drug for injection is contained can be plugged into a disposable adaptor 306 with handles, and a seal 308 can be utilized to ensure that the syringe 302 and the disposable adaptor 306 are securely coupled to each other. When the syringe plunger 304 is pushed, drug contained in syringe 302 is delivered from syringe 302 into the disposable adaptor 306. The drug is further delivered into the patient's skin through the flat array of fine needles 312 at a uniform depth when the array of needles 312 is pushed into a patient's skin until manifold 310 hits the skin.

The use of the drug delivery device 200 may have as many clinical applications as the number of pharmacological agents that require transcutaneous injection or absorption. For non-limiting examples, a few of the potential applications are the injection of local anesthetics, the injection of neuromodulators such as Botulinum toxin (Botox), the injection of insulin and the injection of replacement estrogens and corticosteroids.

In some embodiments, the syringe plunger 210 of the drug delivery device 200 can be powered by, for a non-limiting example, an electric motor. In some embodiments, a fluid pump (not shown) attached to an IV bag and tubing can be connected to the injection chamber 214 and/or the reservoir 208 for continuous injection. In some embodiments, the volume of the syringe plunger 210 in the drug delivery device 200 is calibrated and programmable.

Another application of pixel skin graft harvesting with the PAD (Pixel Array Dermatome) device as described in detail herein is Alopecia. Alopecia is a common aesthetic malady, and it occurs most frequently in the middle-aged male population, but is also observed in the aging baby boomer female population. The most common form of alopecia is Male Pattern Baldness (MPB) that occurs in the frontal-parietal region of the scalp. Male pattern baldness is a sex-linked trait that is transferred by the X chromosome from the mother to male offspring. For men, only one gene is needed to express this phenotype. As the gene is recessive, female pattern baldness requires the transfer of both X linked genes from both mother and father. Phenotypic penetrance can vary from patient to patient and is most frequently expressed in the age of onset and the amount of frontal/partial/occipital alopecia. The patient variability in the phenotypic expression of MPB is due to the variable genotypic translation of this sex-linked trait. Based upon the genotypic occurrence of MPB, the need for hair transplantation is vast. Other non-genetic related etiologies are seen in a more limited segment of the population. These non-genetic etiologies include trauma, fungal infections, lupus erythematosus, radiation and chemotherapy.

A large variety of treatment options have been proposed to the public. These include FDA approved topical medications such as Minoxidil and Finasteride which have had limited success as these agents require the conversion of dormant hair follicles into an anagen growth phase. Other remedies include hairpieces and hair weaving. The standard of practice remains surgical hair transplantation, which involves the transfer of hair plugs, strips and flaps from the hair-bearing scalp into the non hair-bearing scalp. For the most part, conventional hair transplantation involves the transfer of multiple single hair micrographs from the hair-bearing scalp to the non hair-bearing scalp of the same patient. Alternately, the donor plugs are initially harvested as hair strips and then secondarily sectioned into micrographs for transfer to the recipient scalp. Regardless, this multi-staged procedure is both tedious and expensive, involving several hours of surgery for the average patient.

The conventional hair transplantation market has been encumbered by lengthy hair grafting procedures that are performed in several stages. A typical hair grafting procedure involves the transfer of hair plugs from a donor site in the occipital scalp to a recipient site in the balding frontal-parietal scalp. For most procedures, each hair plug is transferred individually to the recipient scalp. Several hundred plugs may be transplanted during a procedure that may require several hours to perform. Post procedure "take" or viability of the transplanted hair plugs is variable due to factors that limit neovascularization at the recipient site. Bleeding and mechanical disruption due to motion are key factors that reduce neovascularization and "take" of hair grafts. Embodiments described herein include surgical instrumentation configured to transfer several hair grafts at once that are secured and aligned en masse at a recipient site on the scalp. The procedures described herein using the PAD of an embodiment reduce the tedium and time required with conventional instrumentation.

Figure 25:
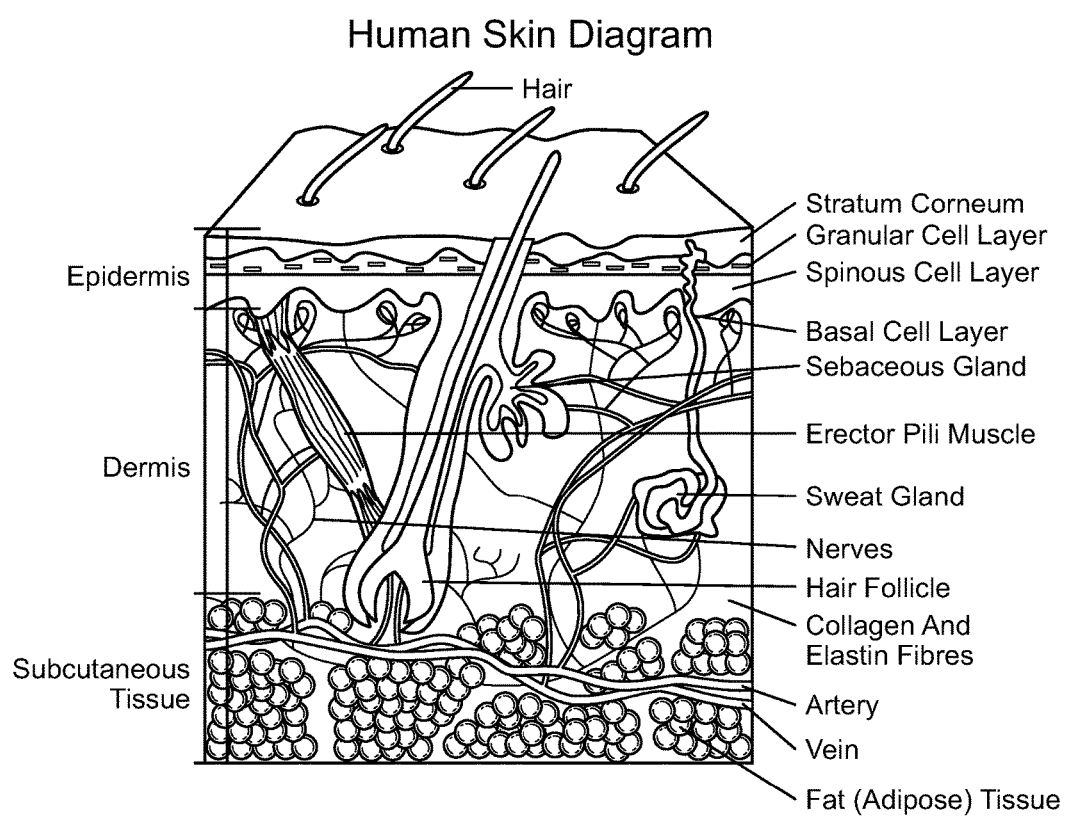
FIG. 25 shows the composition of human skin.

FIG. 25 shows the composition of human skin. Skin comprises two horizontally stratified layers, referred to as the epidermis and the dermis, acting as a biological barrier to the external environment. The epidermis is the enveloping layer and comprises a viable layer of epidermal cells that migrate upward and "mature" into a nonviable layer called the stratum corneum. The stratum corneum is a lipid-keratin composite that serves as a primary biological barrier, and this layer is continually shed and reconstituted in a process called desquamation. The dermis is the subjacent layer that is the main structural support of the skin, and is predominately extracellular and is comprised of collagen fibers.

In addition to the horizontally stratified epidermis and dermis, the skin includes vertically-aligned elements or cellular appendages including the pilosebaceous units, comprising the hair folical and sebacious gland. Pilosebaceous units each include a sebaceous oil gland and a hair follicle. The sebaceous gland is the most superficial and discharges sebum (oil) into the shaft of the hair follicle. The base of the hair follicle is called the bulb and the base of the bulb has a deep generative component called the dermal papilla. The hair follicles are typically aligned at an oblique angle to the skin surface. Hair follicles in a given region of the scalp are aligned parallel to each other. Although pilosebaceous units are common throughout the entire integument, the density and activity of these units within a region of the scalp is a key determinate as to the overall appearance of hair.

In additional to pilosebaceous units, sweat glands also course vertically through the skin. They provide a water-based transudate that assists in thermoregulation. Apocrine sweat glands in the axilla and groin express a more pungent sweat that is responsible for body odor. For the rest of the body, eccrine sweat glands excrete a less pungent sweat for thermoregulation.

Figure 26:
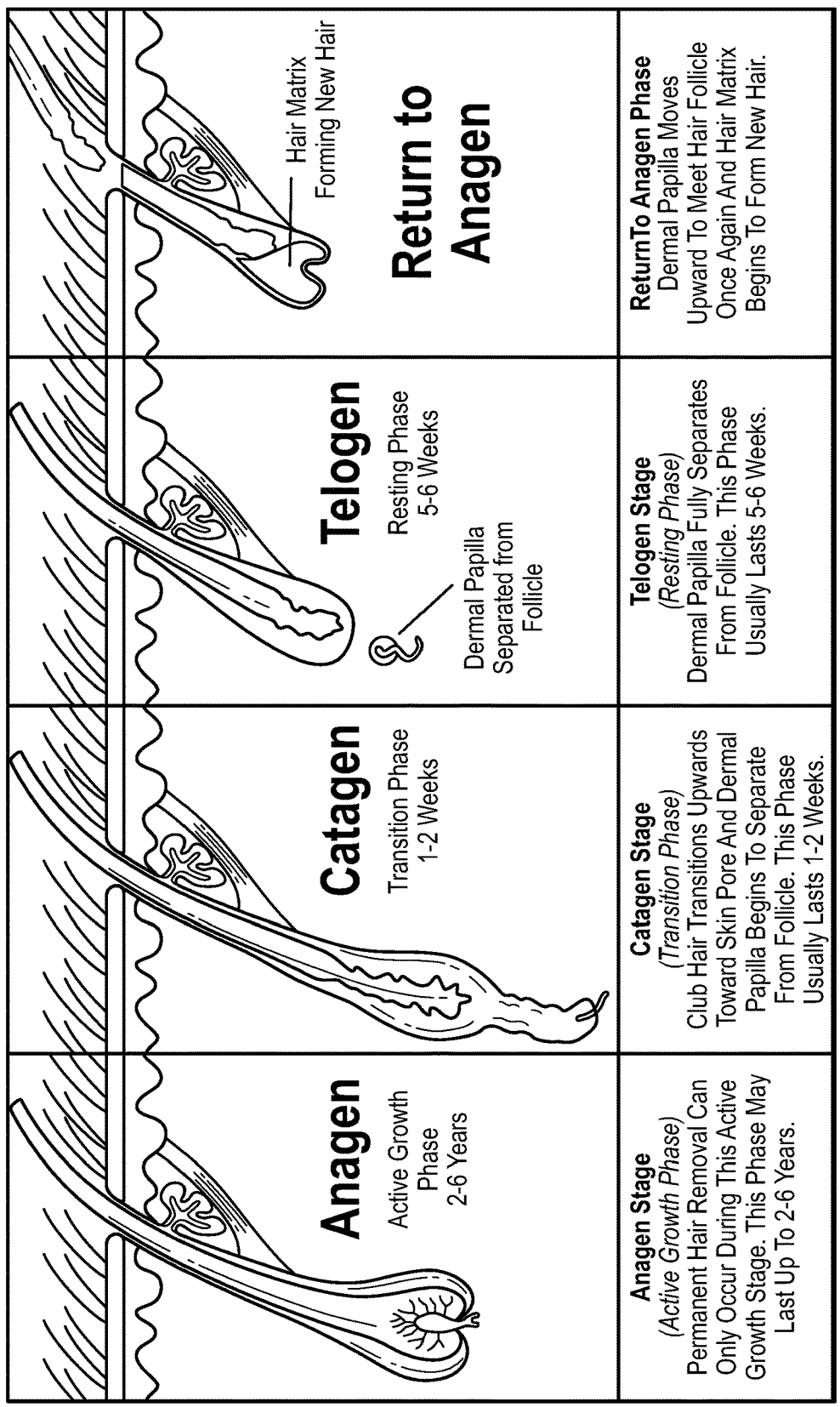
FIG. 26 shows the physiological cycles of hair growth.

Hair follicles proceed through different physiological cycles of hair growth. FIG. 26 shows the physiological cycles of hair growth. The presence of testosterone in a genetically-prone man will produce alopecia to a variable degree in the frontal-parietal scalp. Essentially, the follicle becomes dormant by entering the telogen phase without return to the anagen phase. Male Pattern Baldness occurs when the hair fails to return from the telogen phase to the anagen phase.

The PAD of an embodiment is configured for en-masse harvesting of hair-bearing plugs with en-masse transplantation of hair bearing plugs into non hair-bearing scalp, which truncates conventional surgical procedures of hair transplantation. Generally, the devices, systems and/or methods of an embodiment are used to harvest and align a large multiplicity of small hair bearing plugs in a single surgical step or process, and the same instrumentation is used to prepare the recipient site by performing a multiple pixelated resection of non hair-bearing scalp. The multiple hair-plug graft is transferred and transplanted en-masse to the prepared recipient site. Consequently, through use of an abbreviated procedure, hundreds of hair bearing plugs can be transferred from a donor site to a recipient site. Hair transplantation using the embodiments described herein therefore provides a solution that is a single surgical procedure having ease, simplicity and significant time reduction over the tedious and multiple staged conventional process.

Hair transplantation using the pixel dermatome of an embodiment facilitates improvements in the conventional standard follicular unit extraction (FUT) hair transplant approach. Generally, under the procedure of an embodiment hair follicles to be harvested are taken from the Occipital scalp of the donor. In so doing, the donor site hair is partially shaved, and the perforated plate of an embodiment is located on the scalp and oriented to provide a maximum harvest. FIG. 27 shows harvesting of donor follicles, under an embodiment. The scalpets in the scalpet array are configured to penetrate down to the subcutaneous fat later to capture the hair follicle. Once the hair plugs are incised, they are harvested onto an adhesive membrane by transecting the base of the hair plug with the transection blade, as described in detail herein. Original alignment of the hair plugs with respect to each other at the donor site is maintained by applying the adherent membrane before transecting the base. The aligned matrix of hair plugs on the adherent membrane will then be grafted en masse to a recipient site on the frontal-parietal scalp of the recipient.

FIG. 28 shows preparation of the recipient site, under an embodiment. The recipient site is prepared by resection of non-hair bearing skin plugs in a topographically identical pattern as the harvested occipital scalp donor site. The recipient site is prepared for the mass transplant of the hair plugs using the same instrumentation that was used at the donor site under an embodiment and, in so doing, scalp defects are created at the recipient site. The scalp defects created at the recipient site have the same geometry as the harvested plugs on the adherent membrane.

Figure 29:
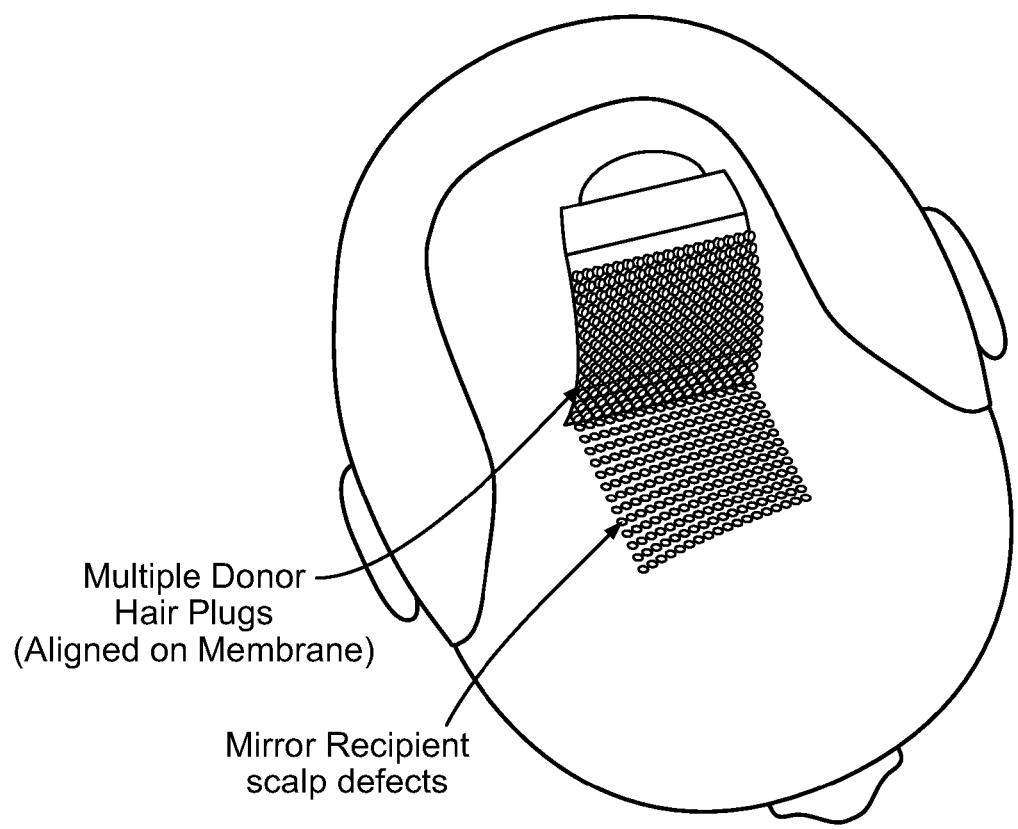
FIG. 29 shows placement of the harvested hair plugs at the recipient site, under an embodiment.

The adherent membrane laden with the harvested hair plugs is applied over the same pattern of scalp defects at the recipient site. Row-by-row, each hair-bearing plug is inserted into its mirror image recipient defect. FIG. 29 shows placement of the harvested hair plugs at the recipient site, under an embodiment. Plug-to-plug alignment is maintained, so the hair that grows from the transplanted hair plugs lays as naturally as it did at the donor site. More uniform alignment between the native scalp and the transplanted hair will also occur.

Figure 30:
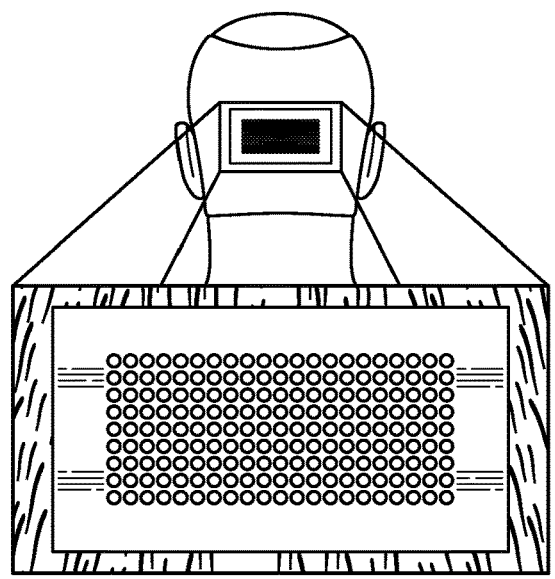
FIG. 30 shows placement of the perforated plate on the occipital scalp donor site, under an embodiment.

More particularly, the donor site hair is partially shaved to prepare for location or placement of the perforated plate on the scalp. The perforated plate is positioned on the occipital scalp donor site to provide a maximum harvest. FIG. 30 shows placement of the perforated plate on the occipital scalp donor site, under an embodiment. Mass harvesting of hair plugs is achieved using the spring-loaded pixilation device comprising the impact punch hand-piece with a scalpet disposable tip. An embodiment is configured for harvesting of individual hair plugs using off-the-shelf FUE extraction devices or biopsy punches; the holes in the perforated plates supplied are sized to accommodate off-the-shelf technology.

Figure 31:
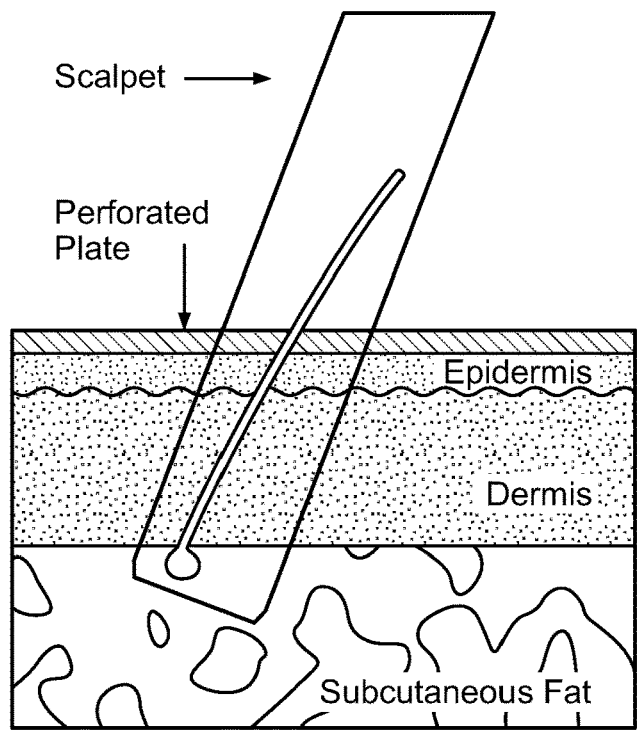
FIG. 31 shows scalpet penetration depth through skin when the scalpet is configured to penetrate to the subcutaneous fat layer to capture the hair follicle, under an embodiment.

The scalpets comprising the scalpet array disposable tip are configured to penetrate down to the subcutaneous fat later to capture the hair follicle. FIG. 31 shows scalpet penetration depth through skin when the scalpet is configured to penetrate to the subcutaneous fat layer to capture the hair follicle, under an embodiment. Once the hair plugs are incised, they are harvested onto an adhesive membrane by transecting the base of the hair plug with the transection blade, but are not so limited. FIG. 32 shows hair plug harvesting using the perforated plate at the occipital donor site, under an embodiment. The original alignment of the hair plugs with respect to each other is maintained by applying an adherent membrane of an embodiment. The adherent membrane is applied before transecting the base of the resected pixels, the embodiments are not so limited. The aligned matrix of hair plugs on the adherent membrane is subsequently grafted en masse to a recipient site on the frontal-parietal scalp.

Additional single hair plugs may be harvested through the perforated plate, to be used to create the visible hairline, for example. FIG. 33 shows creation of the visible hairline, under an embodiment. The visible hairline is determined and developed with a manual FUT technique. The visible hairline and the mass transplant of the vertex may be performed concurrently or as separate stages. If the visible hairline and mass transplant are performed concurrently, the recipient site is developed starting with the visible hairline.

Transplantation of harvested hair plugs comprises preparing the recipient site is prepared by resecting non-hair bearing skin plugs in a topographically identical pattern as the pattern of the harvested occipital scalp donor site. FIG. 34 shows preparation of the donor site using the patterned perforated plate and spring-loaded pixilation device to create identical skin defects at the recipient site, under an embodiment. The recipient site of an embodiment is prepared for the mass transplant of the hair plugs using the same perforated plate and spring-loaded pixilation device that was used at the donor site. Scalp defects are created at the recipient site. These scalp defects have the same geometry as the harvested plugs on the adherent membrane.

Figure 35:
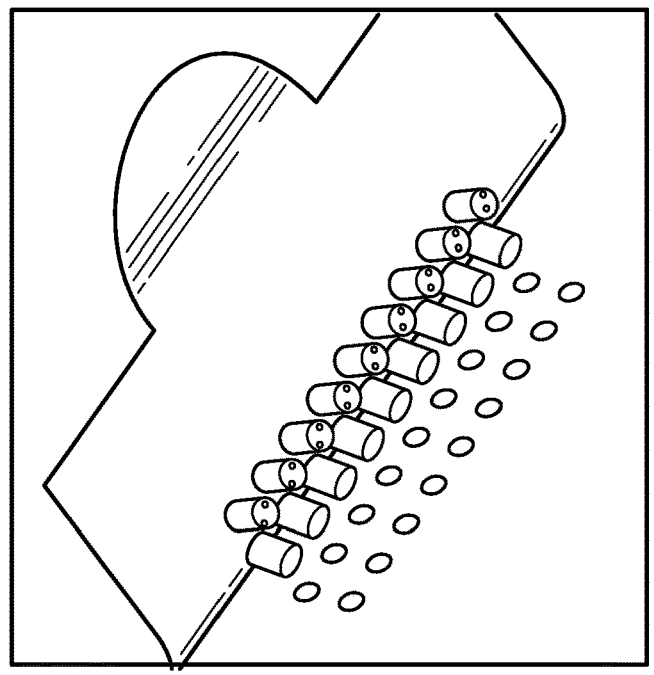
FIG. 35 shows transplantation of harvested plugs by inserting harvested plugs into a corresponding skin defect created at the recipient site, under an embodiment.

The adherent membrane carrying the harvested hair plugs is applied over the same pattern of scalp defects at recipient site. Row-by-row each follicle-bearing or hair-bearing skin plug is inserted into its mirror image recipient defect. FIG. 35 shows transplantation of harvested plugs by inserting harvested plugs into a corresponding skin defect created at the recipient site, under an embodiment. Plug-to-plug alignment is maintained, so the hair that grows from the transplanted hair plugs lays as naturally as it did at the donor site. More uniform alignment between the native scalp and the transplanted hair will also occur.

Figure 36:
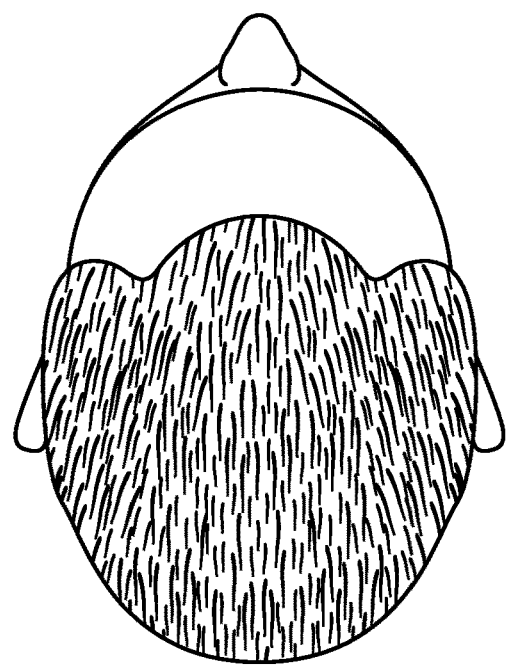
FIG. 36 shows a clinical end point using the pixel dermatome instrumentation and procedure, under an embodiment.

Clinical endpoints vary from patient to patient, but it is predicted that a higher percentage of hair plugs will "take" as a result of improved neovascularization. FIG. 36 shows a clinical end point using the pixel dermatome instrumentation and procedure, under an embodiment. The combination of better "takes", shorter procedure times, and a more natural-looking result, enable the pixel dermatome instrumentation and procedure of an embodiment to overcome the deficiencies in conventional hair transplant approaches.

Embodiments of pixelated skin grafting for skin defects and pixelated skin resection for skin laxity are described in detail herein. These embodiments remove a field of skin pixels in an area of lax skin where skin tightening is desired. The skin defects created by this procedure (e.g., in a range of approximately 1.5-3 mm-diameter) are small enough to heal per primam without visible scarring; the wound closure of the multiple skin defects is performed directionally to produce a desired contouring effect. Live animal testing of the pixel resection procedure has produced excellent results.

The pixel procedure of an embodiment is performed in an office setting under a local anesthetic but is not so limited. The surgeon uses the instrumentation of an embodiment to rapidly resect an array of skin pixels (e.g., circular, elliptical, square, etc.). Relatively little pain is associated with the procedure. The intradermal skin defects generated during the procedure are closed with the application of an adherent Flexan (3M) sheet, but embodiments are not so limited. Functioning as a large butterfly bandage, the Flexan sheet is pulled in a direction that maximizes the aesthetic contouring of the treatment area. A compressive elastic garment is then applied over the dressing to assist aesthetic contouring. During recovery, the patient wears a support garment over the treatment area for a period of time (e.g., 5 days, etc.). After initial healing, the multiplicity of small linear scars within the treatment area is not visibly apparent. Additional skin tightening will occur subsequently over several months from the delayed wound healing response. Consequently, the pixel procedure is a minimally invasive alternative for skin tightening in areas where the extensive scarring of traditional aesthetic plastic surgery is to be avoided.

The pixel procedure evokes cellular and extracellular responses that are obligatory to the clinical outcomes achieved. A physical reduction of the skin surface area occurs due to the fractional resection of skin, which physically removes a portion of skin directly in the area of laxity. In addition, a subsequent tightening of the skin is realized from the delayed wound healing response. Each pixilated resection initiates an obligate wound healing sequence. The healing response effected in an embodiment comprises three phases, as previously described in detail herein.

The first phase of this sequence is the inflammatory phase in which degranulation of mast cells releases histamine into the "wound". Histamine release evokes dilatation of the capillary bed and increases vessel permeability into the extracellular space. This initial wound healing response occurs within the first day and will be evident as erythema on the skin's surface.

Within days of "wounding", the second phase of healing, fibroplasia, commences. During fibroplasia, there is migration and mitotic multiplication of fibroblasts. Fibroplasia has two key features: the deposition of neocollagen and the myofibroblastic contraction of the wound. Histologically, the deposition of neocollagen is identified microscopically as compaction and thickening of the dermis. Although this is a static process, the tensile strength of the skin significantly increases. Myofibroblastic contraction is a dynamic physical process that results in two-dimensional tightening of the skin surface. This process is due to the active cellular contraction of myofibroblasts and the deposition of contractile proteins within the extracellular matrix. Overall, the effect of fibroplasia will be dermal contraction and the deposition of a static supporting scaffolding of neocollagen with a tightened framework. The clinical effect is realized as a delayed tightening of skin with smoothing of skin texture over some number of months. The clinical endpoint is a more youthful appearing skin envelope of the treatment area.

A third and final phase of the delayed wound healing response is maturation. During maturation, there is a strengthening and remodeling of the treatment area due to increased cross-linkage of the collagen fibril matrix (of the dermis). This final stage commences within 6 to 12 months after "wounding" and may extend for at least 1-2 years. Small pixilated resections of skin should preserve the normal dermal architecture during maturation, but without the creation of a visually evident scar that typically occurs with a larger surgical resection of skin. Lastly, there is a related stimulation and rejuvenation of the epidermis from the release of epidermal growth hormone.

Figure 37:
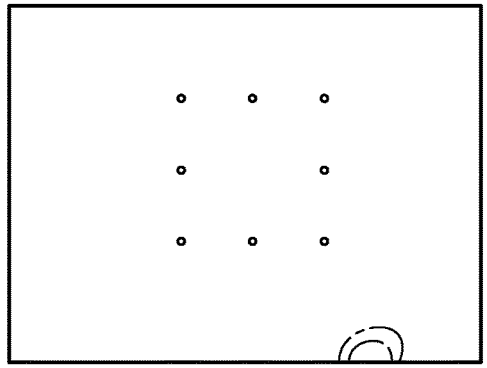
FIG. 37 is an image of the skin tattooed at the corners and midpoints of the area to be resected, under an embodiment.
Figure 38:
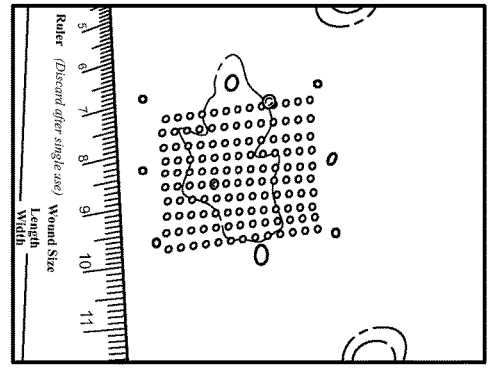
FIG. 38 is an image of the post-operative skin resection field, under an embodiment.

FIGS. 37-42 show images resulting from a pixel procedure conducted on a live animal, under an embodiment. Embodiments described herein were used in this proof-of-concept study in an animal model that verified the pixel procedure produces aesthetic skin tightening without visible scarring. The study used a live porcine model, anesthetized for the procedure. FIG. 37 is an image of the skin tattooed at the corners and midpoints of the area to be resected, under an embodiment. The field margins of resection were demarcated with a tattoo for post-operative assessment, but embodiments are not so limited. The procedure was performed using a perforated plate (e.g., 10×10 pixel array) to designate the area for fractional resection. The fractional resection was performed using biopsy punches (e.g., 1.5 mm diameter). FIG. 38 is an image of the post-operative skin resection field, under an embodiment. Following the pixel resection, the pixelated resection defects were closed (horizontally) with Flexan membrane.

Figure 39:
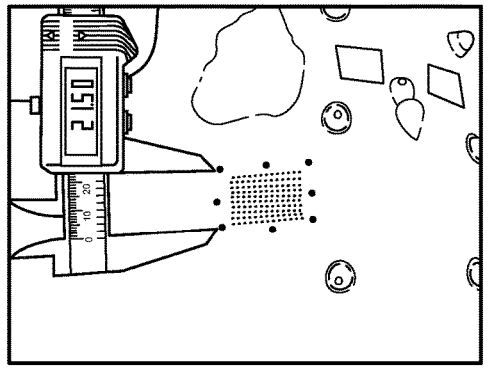
FIG. 39 is an image at 11 days following the procedure showing resections healed per primam, with measured margins, under an embodiment.
Figure 40:
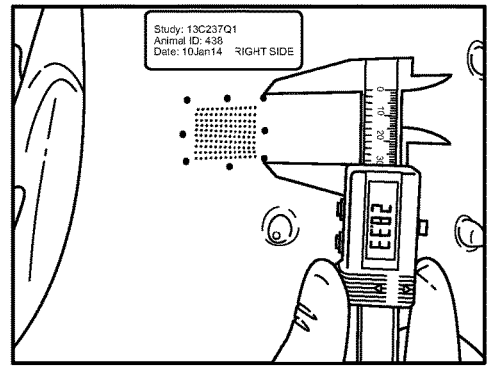
FIG. 40 is an image at 29 days following the procedure showing resections healed per primam and maturation of the resection field continuing per primam, with measured margins, under an embodiment.
Figure 41:
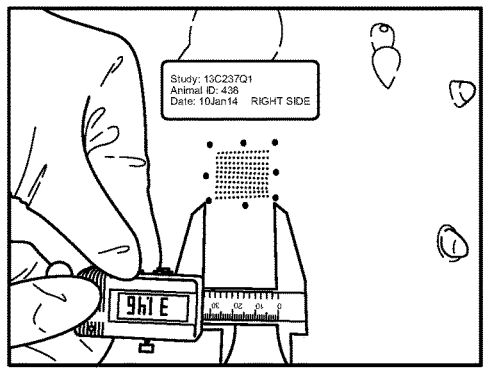
FIG. 41 is an image at 29 days following the procedure showing resections healed per primam and maturation of the resection field continuing per primam, with measured lateral dimensions, under an embodiment.
Figure 42:
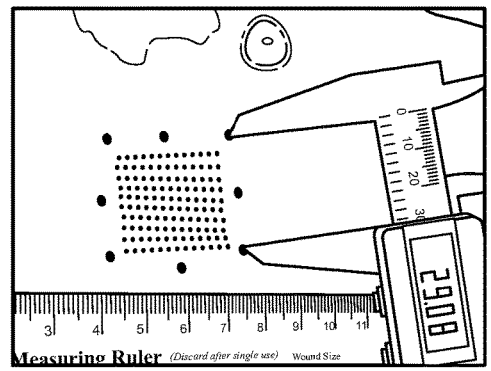
FIG. 42 is an image at 90 days post-operative showing resections healed per primam and maturation of the resection field continuing per primam, with measured lateral dimensions, under an embodiment.

Eleven days following the procedure, all resections had healed per primam in the area designated by the tattoo, and photographic and dimensional measurements were made. FIG. 39 is an image at 11 days following the procedure showing resections healed per primam, with measured margins, under an embodiment. Photographic and dimensional measurements were subsequently made 29 days following the procedure. FIG. 40 is an image at 29 days following the procedure showing resections healed per primam and maturation of the resection field continuing per primam, with measured margins, under an embodiment. FIG. 41 is an image at 29 days following the procedure showing resections healed per primam and maturation of the resection field continuing per primam, with measured lateral dimensions, under an embodiment. Photographic and dimensional measurements were repeated 90 days post-operative, and the test area skin was completely smooth to touch. FIG. 42 is an image at 90 days post-operative showing resections healed per primam and maturation of the resection field continuing per primam, with measured lateral dimensions, under an embodiment.

Embodiments include an apparatus comprising a housing configured to include a scalpet device. The scalpet device comprises a substrate and a scalpet array. The scalpet array includes a plurality of scalpets arranged in a configuration on the substrate. The substrate and the plurality of scalpets is configured to be deployed from the housing and retracted into the housing. The plurality of scalpets is configured to generate a plurality of incised skin pixels at a target site when deployed.

Embodiments include an apparatus, comprising: a housing configured to include a scalpet device; and the scalpet device comprising a substrate and a scalpet array, wherein the scalpet array includes a plurality of scalpets arranged in a configuration on the substrate, wherein the substrate and the plurality of scalpets is configured to be deployed from the housing and retracted into the housing, wherein the plurality of scalpets is configured to generate a plurality of incised skin pixels at a target site when deployed.

The housing is configured to be removeably coupled to a receiver.

The receiver is a component of a control device.

The control device comprises a proximal end and a distal end, wherein the proximal end includes an actuator mechanism and the distal end includes the receiver.

The scalpet array is configured to be deployed in response to activation of the actuator mechanism.

The proximal end of the control device is configured to be hand-held.

The scalpet device is configured so the scalpet array is deployed from the scalpet device and retracted back into the scalpet device in response to activation of the actuator mechanism.

The scalpet device is configured so the scalpet array is deployed from the scalpet device in response to activation of the actuator mechanism.

The scalpet device is configured so the scalpet array is retracted back into the scalpet device in response to release of the actuator mechanism.

The control device is configured to be disposable.

The control device is configured to be at least one of cleaned, disinfected, and sterilized.

The apparatus comprises an adherent substrate configured to capture the plurality of incised skin pixels.

The scalpet device is configured to include the adherent substrate.

The housing is configured to include the adherent substrate.

The adherent substrate comprises a flexible substrate.

The adherent substrate comprises a semi-porous membrane.

The apparatus comprises a vacuum component.

The vacuum component is coupled to the housing.

The vacuum component is coupled to the scalpet device.

The vacuum component is coupled to the scalpet device via the housing.

The vacuum component is configured to generate a low-pressure zone within at least one of the scalpet device and the control device.

The low-pressure zone is configured to evacuate the plurality of incised skin pixels.

The housing is configured to be removeably coupled to a control device, wherein the vacuum component is coupled to the control device.

The apparatus comprises a radio frequency (RF) component.

The RF component is configured to provide thermal energy to at least one of the scalpet device and the scalpet array.

The RF component is configured to provide vibrational energy to at least one of the scalpet device and the scalpet array.

The RF component is configured to provide rotational energy to at least one of the scalpet device and the scalpet array.

The RF component is configured to provide acoustic energy to at least one of the scalpet device and the scalpet array.

The RF component is coupled to the housing.

The RF component is coupled to the scalpet device.

The RF component is coupled to the scalpet device via the housing.

The RF component is coupled to the scalpet array.

The RF component is coupled to the scalpet array via the housing.

The RF component is coupled to at least one scalpet of the scalpet array.

The RF component is coupled to the at least one scalpet of the scalpet array via the housing.

The housing is configured to be removably coupled to a control device, wherein the RF component is coupled to the control device.

The apparatus comprises a vacuum component coupled to at least one of the scalpet device and the housing, and a radio frequency (RF) component coupled to at least one of the scalpet device, the scalpet array, and the housing.

The vacuum component is configured to generate a low-pressure zone within at least one of the scalpet device and the housing The RF component is configured to provide energy to at least one of the scalpet device, the scalpet array, and the housing.

The energy comprises at least one of thermal energy, vibrational energy, rotational energy, and acoustic energy.

The target site includes a recipient site, wherein the incised skin pixels generate skin defects at the recipient site.

The target site includes a donor site, wherein the plurality of incised skin pixels is harvested at the donor site.

The target site includes a recipient site, wherein the incised skin pixels generate skin defects at the recipient site.

The apparatus comprises an adherent substrate configured to capture the plurality of incised skin pixels at the donor site and transfer the plurality of incised skin pixels to the recipient site.

The adherent substrate is configured to maintain relative positioning of the plurality of incised skin pixels during transfer to and application at the recipient site.

The adherent substrate is configured to apply the incised skin pixels to the skin defects at the recipient site.

The adherent substrate is configured to align the incised skin pixels with the skin defects at the recipient site.

The adherent substrate is configured to insert each incised skin pixel into a corresponding skin defect at the recipient site.

The apparatus comprises at least one bandage configured for application at the target site.

The at least one bandage is configured to apply force to close the target site. The at least one bandage is configured to apply directional force to control a direction of the closure at the target site.

The at least one bandage includes a first bandage configured for application at the donor site.

The at least one bandage includes a second bandage configured for application at the recipient site.

The scalpet device is configured to transfer a load to subjacent skin surface that includes the target site, wherein the skin pixels are incised by application of the load.

The scalpet array is configured to transfer a load to subjacent skin surface that includes the target site, wherein the skin pixels are incised by application of the load.

The scalpet device is configured to be disposable.

The scalpet device is configured to be at least one of cleaned, disinfected, and sterilized.

The apparatus comprises a template configured for positioning at the target site. The scalpet device is configured to align with the template.

The scalpet array is configured to align with the template.

The template is on a skin surface at the target site.

The template comprises an indicator on the skin surface at the target site.

The template includes a guide plate configured for positioning at the target site and comprising perforations arranged in a pattern.

The scalpet array is removeably coupled to the scalpet device.

The scalpet array is disposable.

A shape of each scalpet of the scalpet array is elliptical.

A shape of each scalpet of the scalpet array is circular.

A shape of each scalpet of the scalpet array is semicircular.

A shape of each scalpet of the scalpet array is one of square, rectangular, and flat.

Each scalpet of the at least one scalpet includes a beveled surface.

Each scalpet of the plurality of scalpets includes at least one pointed surface.

Each scalpet of the plurality of scalpets includes at least one needle.

The at least one needle comprises at least one needle including multiple points.

The scalpet array generates the incised skin pixels using at least one of piercing force, impact force, and rotational force.

The scalpet array generates the incised skin pixels using radio frequency (RF) energy.

The scalpet array generates the incised skin pixels using vibrational energy.

At least one scalpet of the scalpet array comprises a through orifice.

At least one diametric dimension of each scalpet of the scalpet array is approximately in a range 0.5 millimeters to 4.0 millimeters.

The apparatus comprises a guide plate configured for positioning as a template at the target site, wherein the guide plate includes perforations arranged in a pattern.

The scalpet array is configured to align with the perforations in the guide plate.

The scalpet array is applied to a donor site via the perforations in the guide plate, wherein the plurality of skin pixels are incised.

The scalpet array is applied to a recipient site via the perforations in the guide plate, wherein a plurality of skin defects are generated.

The target site includes the donor site and the recipient site.

The plurality of incised skin pixels and the plurality of skin defects are generated according to the pattern.

The apparatus comprises an adherent substrate configured to capture the plurality of incised skin pixels at the donor site and transfer the plurality of incised skin pixels to the recipient site.

The adherent substrate is configured to maintain relative positioning of the plurality of incised skin pixels during transfer to and application at the recipient site.

The scalpet array is applied to the donor site directly through the perforations and the skin pixels are incised.

The scalpet array is applied to the recipient site directly through the perforations and the skin defects are generated.

The guide plate is at least one of adherent, rigid, semi-rigid, conformable, non-conformable, and non-deformable.

The guide plate includes at least one of metal, plastic, polymer, and membranous material.

The guide plate is configured to transmit a load to a skin surface of at least one of the donor site and the recipient site.

The guide plate is positioned directly on a skin surface at the target site.

The guide plate is configured to extrude the plurality of incised skin pixels.

The plurality of skin pixels is extruded through the perforations in response to an applied load.

The plurality of skin pixels is extruded through the incised skin surface in response to an applied load.

The apparatus comprises a cutting member.

The incised skin pixels are transected by the cutting member.

The apparatus comprises an adherent substrate configured to capture the incised skin pixels.

The cutting member is coupled to a frame.

The frame is coupled to a guide plate, wherein the guide plate is configured as a guide for the scalpet device.

The adherent substrate is coupled to at least one of the frame and the guide plate.

The incised skin pixels include hair follicles.

The skin defects are configured to evoke neovascularization in the incised skin pixels inserted at the recipient site.

The skin defects are configured to evoke a wound healing response in the incised skin pixels inserted at the recipient site.

Embodiments include an apparatus, comprising: a housing including a scalpet device; and the scalpet device comprising a scalpet array that includes a plurality of scalpets arranged in a pattern, wherein the plurality of scalpets is deployable from the housing to generate a plurality of incised skin pixels at a target site.

Embodiments include an apparatus comprising a housing including a scalpet device. The scalpet device comprises a scalpet array that includes a plurality of scalpets arranged in a pattern. The plurality of scalpets is deployable from the housing to generate a plurality of incised skin pixels at a target site.

Embodiments include a system comprising a control device comprising a proximal end and a distal end. The proximal end includes an actuator mechanism and the distal end includes a receiver. The system includes a scalpet device configured to be removeably coupled to the receiver of the control device. The scalpet device includes a substrate and a scalpet array comprising a plurality of scalpets arranged in a configuration on the substrate. The substrate and the plurality of scalpets are configured to be deployed in response to activation of the actuator mechanism. The plurality of scalpets is configured to generate a plurality of incised skin pixels at a target site when deployed.

Embodiments include a system comprising: a control device comprising a proximal end and a distal end, wherein the proximal end includes an actuator mechanism and the distal end includes a receiver; and a scalpet device configured to be removeably coupled to the receiver of the control device, wherein the scalpet device includes a substrate and a scalpet array comprising a plurality of scalpets arranged in a configuration on the substrate, wherein the substrate and the plurality of scalpets are configured to be deployed in response to activation of the actuator mechanism, wherein the plurality of scalpets is configured to generate a plurality of incised skin pixels at a target site when deployed.

The proximal end of the control device is configured to be hand-held.

The target site includes a recipient site, wherein the incised skin pixels generate skin defects at the recipient site.

The target site includes a donor site, wherein the plurality of incised skin pixels is harvested at the donor site.

The target site includes a recipient site, wherein the incised skin pixels generate skin defects at the recipient site.

The system comprises an adherent substrate configured to capture the plurality of incised skin pixels at the donor site and transfer the plurality of incised skin pixels to the recipient site.

The adherent substrate is configured to maintain relative positioning of the plurality of incised skin pixels during transfer to and application at the recipient site.

The adherent substrate is configured to apply the incised skin pixels to the skin defects at the recipient site.

The adherent substrate is configured to align the incised skin pixels with the skin defects at the recipient site.

The adherent substrate is configured to insert each incised skin pixel into a corresponding skin defect at the recipient site.

The system comprises at least one bandage configured for application at the target site.

The at least one bandage is configured to apply force to close the target site. The at least one bandage is configured to apply directional force to control a direction of the closure at the target site.

The at least one bandage includes a first bandage configured for application at the donor site.

The at least one bandage includes a second bandage configured for application at the recipient site.

The system comprises an adherent substrate configured to capture the plurality of incised skin pixels.

The scalpet device is configured to include the adherent substrate.

The adherent substrate comprises a flexible substrate.

The adherent substrate comprises a semi-porous membrane.

The scalpet device is configured so the scalpet array is deployed from the scalpet device and retracted back into the scalpet device in response to activation of the actuator mechanism.

The scalpet device is configured so the scalpet array is deployed from the scalpet device in response to activation of the actuator mechanism.

The scalpet device is configured so the scalpet array is retracted back into the scalpet device in response to release of the actuator mechanism.

The scalpet device is configured to transfer a load to subjacent skin surface that includes the target site, wherein the skin pixels are incised by application of the load.

The scalpet array is configured to transfer a load to subjacent skin surface that includes the target site, wherein the skin pixels are incised by application of the load.

The scalpet device is configured to be disposable.

The scalpet device is configured to be at least one of cleaned, disinfected, and sterilized.

The control device is configured to be disposable.

The control device is configured to be at least one of cleaned, disinfected, and sterilized.

The system comprises a template configured for positioning at the target site.

The scalpet device is configured to align with the template.

The scalpet array is configured to align with the template.

The template is on a skin surface at the target site.

The template comprises an indicator on the skin surface at the target site.

The template includes a guide plate configured for positioning at the target site and comprising perforations arranged in a pattern.

The scalpet array is removeably coupled to the scalpet device.

The scalpet array is disposable.

A shape of each scalpet of the scalpet array is elliptical.

A shape of each scalpet of the scalpet array is circular.

A shape of each scalpet of the scalpet array is semicircular.

A shape of each scalpet of the scalpet array is one of square, rectangular, and flat.

Each scalpet of the at least one scalpet includes a beveled surface.

Each scalpet of the plurality of scalpets includes at least one pointed surface.

Each scalpet of the plurality of scalpets includes at least one needle.

The at least one needle comprises at least one needle including multiple points.

The scalpet array generates the incised skin pixels using at least one of piercing force, impact force, and rotational force.

The scalpet array generates the incised skin pixels using radio frequency (RF) energy.

The scalpet array generates the incised skin pixels using vibrational energy.

At least one scalpet of the scalpet array comprises a through orifice.

At least one diametric dimension of each scalpet of the scalpet array is approximately in a range 0.5 millimeters to 4.0 millimeters.

The system comprises a vacuum component.

The vacuum component is coupled to the control device.

The vacuum component is coupled to the scalpet device.

The vacuum component is coupled to the scalpet device via the control device.

The vacuum component is configured to generate a low-pressure zone within at least one of the scalpet device and the control device.

The low-pressure zone is configured to evacuate the plurality of incised skin pixels.

The system comprises a radio frequency (RF) component.

The RF component is configured to provide thermal energy to at least one of the scalpet device, the scalpet array, and the control device.

The RF component is configured to provide vibrational energy to at least one of the scalpet device, the scalpet array, and the control device.

The RF component is configured to provide rotational energy to at least one of the scalpet device, the scalpet array, and the control device.

The RF component is configured to provide acoustic energy to at least one of the scalpet device, the scalpet array, and the control device.

The RF component is coupled to the control device.

The RF component is coupled to the scalpet device.

The RF component is coupled to the scalpet device via the control device.

The RF component is coupled to the scalpet array.

The RF component is coupled to the scalpet array via the control device.

The RF component is coupled to at least one scalpet of the scalpet array.

The RF component is coupled to the at least one scalpet of the scalpet array via the control device.

The system comprises a vacuum component coupled to at least one of the scalpet device and the control device, and a radio frequency (RF) component coupled to at least one of the scalpet device, the scalpet array, and the control device.

The vacuum component is configured to generate a low-pressure zone within at least one of the scalpet device and the control device The RF component is configured to provide energy to at least one of the scalpet device, the scalpet array, and the control device.

The energy comprises at least one of thermal energy, vibrational energy, rotational energy, and acoustic energy.

The system comprises a guide plate configured for positioning as a template at the target site, wherein the guide plate includes perforations arranged in a pattern.

The scalpet array is configured to align with the perforations in the guide plate.

The scalpet array is applied to a donor site via the perforations in the guide plate, wherein the plurality of skin pixels are incised.

The scalpet array is applied to a recipient site via the perforations in the guide plate, wherein a plurality of skin defects are generated.

The target site includes the donor site and the recipient site.

The plurality of incised skin pixels and the plurality of skin defects are generated according to the pattern.

The system comprises an adherent substrate configured to capture the plurality of incised skin pixels at the donor site and transfer the plurality of incised skin pixels to the recipient site.

The adherent substrate is configured to maintain relative positioning of the plurality of incised skin pixels during transfer to and application at the recipient site.

The scalpet array is applied to the donor site directly through the perforations and the skin pixels are incised.

The scalpet array is applied to the recipient site directly through the perforations and the skin defects are generated.

The guide plate is at least one of adherent, rigid, semi-rigid, conformable, non-conformable, and non-deformable.

The guide plate includes at least one of metal, plastic, polymer, and membranous material.

The guide plate is configured to transmit a load to a skin surface of at least one of the donor site and the recipient site.

The guide plate is positioned directly on a skin surface at the target site.

The guide plate is configured to extrude the plurality of incised skin pixels.

The plurality of skin pixels is extruded through the perforations in response to an applied load.

The plurality of skin pixels is extruded through the incised skin surface in response to an applied load.

The system comprises a cutting member.

The incised skin pixels are transected by the cutting member.

An adherent substrate configured to capture the incised skin pixels.

The cutting member is coupled to a frame.

The frame is coupled to a guide plate, wherein the guide plate is configured as a guide for the scalpet device.

The adherent substrate is coupled to at least one of the frame and the guide plate.

The incised skin pixels include hair follicles.

The skin defects are configured to evoke neovascularization in the incised skin pixels inserted at the recipient site.

The skin defects are configured to evoke a wound healing response in the incised skin pixels inserted at the recipient site.

Embodiments include a system comprising a control device. The system includes a scalpet device removeably coupled to the control device. The scalpet device includes a scalpet array comprising a plurality of scalpets arranged in a pattern. The plurality of scalpets is configured to deploy and retract in response to activation by the control device and generate a plurality of incised skin pixels at a target site.

Embodiments include a system comprising: a control device; and a scalpet device removeably coupled to the control device, wherein the scalpet device includes a scalpet array comprising a plurality of scalpets arranged in a pattern, wherein the plurality of scalpets are configured to deploy and retract in response to activation by the control device and generate a plurality of incised skin pixels at a target site.

Embodiments include a system comprising a control device comprising an actuator mechanism. The system includes a scalpet device configured to be removeably coupled to the control device. The scalpet device includes a substrate and a scalpet array comprising a plurality of scalpets arranged in a pattern on the substrate. The substrate and the plurality of scalpets are configured to at least one of deploy and retract in response to activation of the actuator mechanism. The plurality of scalpets is configured to generate a plurality of incised skin pixels at a target site when deployed.

Embodiments include a system comprising: a control device comprising an actuator mechanism; and a scalpet device configured to be removeably coupled to the control device, wherein the scalpet device includes a substrate and a scalpet array comprising a plurality of scalpets arranged in a pattern on the substrate, wherein the substrate and the plurality of scalpets are configured to at least one of deploy and retract in response to activation of the actuator mechanism, wherein the plurality of scalpets is configured to generate a plurality of incised skin pixels at a target site when deployed.

Embodiments include a system comprising a housing configured to include a scalpet device. The scalpet device comprises a substrate and a scalpet array. The scalpet array includes a plurality of scalpets arranged in a configuration on the substrate. The substrate and the plurality of scalpets is configured to be deployed from the housing and retracted into the housing. The plurality of scalpets is configured to generate a plurality of incised skin pixels at a target site when deployed. The system includes a vacuum component configured to generate a low-pressure zone adjacent the scalpet device.

Embodiments include a system, comprising: a housing configured to include a scalpet device; the scalpet device comprising a substrate and a scalpet array, wherein the scalpet array includes a plurality of scalpets arranged in a configuration on the substrate, wherein the substrate and the plurality of scalpets is configured to be deployed from the housing and retracted into the housing, wherein the plurality of scalpets is configured to generate a plurality of incised skin pixels at a target site when deployed; and a vacuum component configured to generate a low pressure zone adjacent the scalpet device.

The vacuum component is coupled to the housing.

The vacuum component is coupled to the scalpet device.

The vacuum component is coupled to the scalpet device via the housing.

The vacuum component is configured to generate the low-pressure zone within the housing.

The low pressure zone is configured to evacuate the plurality of incised skin pixels.

The housing is configured to be removeably coupled to a receiver.

The receiver is a component of a control device.

The control device comprises a proximal end and a distal end, wherein the proximal end includes an actuator mechanism and the distal end includes the receiver.

The scalpet array is configured to be deployed in response to activation of the actuator mechanism.

The proximal end of the control device is configured to be hand-held.

The scalpet device is configured so the scalpet array is deployed from the scalpet device and retracted back into the scalpet device in response to activation of the actuator mechanism.

The scalpet device is configured so the scalpet array is deployed from the scalpet device in response to activation of the actuator mechanism.

The scalpet device is configured so the scalpet array is retracted back into the scalpet device in response to release of the actuator mechanism.

The control device is configured to be disposable.

The control device is configured to be at least one of cleaned, disinfected, and sterilized.

The system comprises an adherent substrate configured to capture the plurality of incised skin pixels.

The scalpet device is configured to include the adherent substrate.

The housing is configured to include the adherent substrate.

The adherent substrate comprises a flexible substrate.

The adherent substrate comprises a semi-porous membrane.

The system comprises a radio frequency (RF) component.

The RF component is configured to provide thermal energy to at least one of the scalpet device and the scalpet array.

The RF component is configured to provide vibrational energy to at least one of the scalpet device and the scalpet array.

The RF component is configured to provide rotational energy to at least one of the scalpet device and the scalpet array.

The RF component is configured to provide acoustic energy to at least one of the scalpet device and the scalpet array.

The RF component is coupled to the housing.

The RF component is coupled to the scalpet device.

The RF component is coupled to the scalpet device via the housing.

The RF component is coupled to the scalpet array.

The RF component is coupled to the scalpet array via the housing.

The RF component is coupled to at least one scalpet of the scalpet array.

The RF component is coupled to the at least one scalpet of the scalpet array via the housing.

The housing is configured to be removeably coupled to a control device, wherein the RF component is coupled to the control device.

The target site includes a recipient site, wherein the incised skin pixels generate skin defects at the recipient site.

The target site includes a donor site, wherein the plurality of incised skin pixels IS harvested at the donor site.

The target site includes a recipient site, wherein the incised skin pixels generate skin defects at the recipient site.

The system comprises an adherent substrate configured to capture the plurality of incised skin pixels at the donor site and transfer the plurality of incised skin pixels to the recipient site.

The adherent substrate is configured to maintain relative positioning of the plurality of incised skin pixels during transfer to and application at the recipient site.

The adherent substrate is configured to apply the incised skin pixels to the skin defects at the recipient site.

The adherent substrate is configured to align the incised skin pixels with the skin defects at the recipient site.

The adherent substrate is configured to insert each incised skin pixel into a corresponding skin defect at the recipient site.

The system comprises at least one bandage configured for application at the target site.

The at least one bandage is configured to apply force to close the target site.

The at least one bandage is configured to apply directional force to control a direction of the closure at the target site.

The at least one bandage includes a first bandage configured for application at the donor site.

The at least one bandage includes a second bandage configured for application at the recipient site.

The scalpet device is configured to transfer a load to subjacent skin surface that includes the target site, wherein the skin pixels are incised by application of the load.

The scalpet array is configured to transfer a load to subjacent skin surface that includes the target site, wherein the skin pixels are incised by application of the load.

The scalpet device is configured to be disposable.

The scalpet device is configured to be at least one of cleaned, disinfected, and sterilized.

The system comprises a template configured for positioning at the target site.

The scalpet device is configured to align with the template.

The scalpet array is configured to align with the template.

The template is on a skin surface at the target site.

The template comprises an indicator on the skin surface at the target site.

The template includes a guide plate configured for positioning at the target site and comprising perforations arranged in a pattern.

The scalpet array is removeably coupled to the scalpet device.

The scalpet array is disposable.

A shape of each scalpet of the scalpet array is elliptical.

A shape of each scalpet of the scalpet array is circular.

A shape of each scalpet of the scalpet array is semicircular.

A shape of each scalpet of the scalpet array is one of square, rectangular, and flat.

Each scalpet of the at least one scalpet includes a beveled surface.

Each scalpet of the plurality of scalpets includes at least one pointed surface.

Each scalpet of the plurality of scalpets includes at least one needle.

The at least one needle comprises at least one needle including multiple points.

The scalpet array generates the incised skin pixels using at least one of piercing force, impact force, and rotational force.

The scalpet array generates the incised skin pixels using radio frequency (RF) energy.

The scalpet array generates the incised skin pixels using vibrational energy.

At least one scalpet of the scalpet array comprises a through orifice.

At least one diametric dimension of each scalpet of the scalpet array is approximately in a range 0.5 millimeters to 4.0 millimeters.

The system comprises a guide plate configured for positioning as a template at the target site, wherein the guide plate includes perforations arranged in a pattern.

The scalpet array is configured to align with the perforations in the guide plate.

The scalpet array is applied to a donor site via the perforations in the guide plate, wherein the plurality of skin pixels are incised.

The scalpet array is applied to a recipient site via the perforations in the guide plate, wherein a plurality of skin defects are generated.

The target site includes the donor site and the recipient site.

The plurality of incised skin pixels and the plurality of skin defects are generated according to the pattern.

The system comprises an adherent substrate configured to capture the plurality of incised skin pixels at the donor site and transfer the plurality of incised skin pixels to the recipient site.

The adherent substrate is configured to maintain relative positioning of the plurality of incised skin pixels during transfer to and application at the recipient site.

The scalpet array is applied to the donor site directly through the perforations and the skin pixels are incised.

The scalpet array is applied to the recipient site directly through the perforations and the skin defects are generated.

The guide plate is at least one of adherent, rigid, semi-rigid, conformable, non-conformable, and non-deformable.

The guide plate includes at least one of metal, plastic, polymer, and membranous material.

The guide plate is configured to transmit a load to a skin surface of at least one of the donor site and the recipient site.

The guide plate is positioned directly on a skin surface at the target site.

The guide plate is configured to extrude the plurality of incised skin pixels.

The plurality of skin pixels is extruded through the perforations in response to an applied load.

The plurality of skin pixels is extruded through the incised skin surface in response to an applied load.

The system comprises a cutting member.

The incised skin pixels are transected by the cutting member.

The system comprises an adherent substrate configured to capture the incised skin pixels.

The cutting member is coupled to a frame.

The frame is coupled to a guide plate, wherein the guide plate is configured as a guide for the scalpet device.

The adherent substrate is coupled to at least one of the frame and the guide plate.

The incised skin pixels include hair follicles.

The skin defects are configured to evoke neovascularization in the incised skin pixels inserted at the recipient site.

The skin defects are configured to evoke a wound healing response in the incised skin pixels inserted at the recipient site.

Embodiments include a system comprising a housing including a scalpet device. The scalpet device comprises a scalpet array that includes a plurality of scalpets arranged in a pattern. The plurality of scalpets is deployable from the housing to generate a plurality of incised skin pixels at a target site. The system includes a vacuum component configured to generate a low-pressure zone adjacent the scalpet device.

Embodiments include a system, comprising: a housing including a scalpet device; and the scalpet device comprising a scalpet array that includes a plurality of scalpets arranged in a pattern, wherein the plurality of scalpets is deployable from the housing to generate a plurality of incised skin pixels at a target site; and a vacuum component configured to generate a low pressure zone adjacent the scalpet device.

Embodiments include a method comprising positioning at a target site a housing comprising a scalpet device. The scalpet device includes a substrate and a scalpet array. The scalpet array includes a plurality of scalpets arranged in a configuration on the substrate. The method includes deploying the scalpet array from the housing into tissue at the target site and generating a plurality of incised skin pixels at the target site. The method includes retracting the scalpet array into the housing from the target site.

Embodiments include a method comprising: positioning at a target site a housing comprising a scalpet device, wherein the scalpet device includes a substrate and a scalpet array, wherein the scalpet array includes a plurality of scalpets arranged in a configuration on the substrate; deploying the scalpet array from the housing into tissue at the target site and generating a plurality of incised skin pixels at the target site; and retracting the scalpet array into the housing from the target site.

The method comprises coupling the housing to a receiver that is a component of a control device.

The control device comprises a proximal end and a distal end, wherein the proximal end includes an actuator mechanism and the distal end includes the receiver.

The deploying comprising deploying the scalpet array in response to activation of the actuator mechanism.

The scalpet array in response to activation of the actuator mechanism.

The retracting comprises retracting the scalpet array in response to release of the actuator mechanism.

The proximal end of the control device is configured to be hand-held.

The method comprises decoupling the scalpet device from the receiver and disposing of the scalpet device.

The method comprises at least one of cleaning, disinfecting, and sterilizing the control device.

The method comprises capturing the plurality of incised skin pixels using an adherent substrate.

The scalpet device includes the adherent substrate.

The housing includes the adherent substrate.

The adherent substrate comprises a flexible substrate.

The adherent substrate comprises a semi-porous membrane.

The method comprises harvesting the plurality of incised skin pixels.

The harvesting comprises evacuating the plurality of incised skin pixels.

The harvesting comprises generating a low-pressure zone within at least one of the scalpet device and the housing.

The generating of the low-pressure zone comprises using a vacuum component.

The vacuum component is coupled to the housing.

The vacuum component is coupled to the scalpet device.

The vacuum component is coupled to the scalpet device via the housing.

The housing is configured to be removeably coupled to a control device, wherein the vacuum component is coupled to the control device.

The generating of the plurality of incised skin pixels comprises providing energy to at least one of the scalpet device, the scalpet array, and the housing.

The providing the energy comprises using a radio frequency (RF) component.

The energy comprises at least one of thermal energy, vibrational energy, rotational energy, and acoustic energy.

The providing the energy comprises providing thermal energy to at least one of the scalpet device and the scalpet array.

The providing the energy comprises providing vibrational energy to at least one of the scalpet device and the scalpet array.

The providing the energy comprises providing rotational energy to at least one of the scalpet device and the scalpet array.

The providing the energy comprises providing acoustic energy to at least one of the scalpet device and the scalpet array.

The RF component is coupled to the housing.

The RF component is coupled to the scalpet device.

The RF component is coupled to the scalpet device via the housing.

The RF component is coupled to the scalpet array.

The RF component is coupled to the scalpet array via the housing.

The RF component is coupled to at least one scalpet of the scalpet array.

The RF component is coupled to the at least one scalpet of the scalpet array via the housing.

The housing is configured to be removeably coupled to a control device, wherein the RF component is coupled to the control device.

The method comprises harvesting the plurality of incised skin pixels using a vacuum component, wherein the generating of the plurality of incised skin pixels comprises using radio frequency (RF) energy.

The vacuum component is configured to generate a low-pressure zone within at least one of the scalpet device and the housing.

The RF component is configured to provide energy to at least one of the scalpet device, the scalpet array, and the housing.

The energy comprises at least one of thermal energy, vibrational energy, rotational energy, and acoustic energy.

The target site includes a recipient site, wherein the incised skin pixels generate skin defects at the recipient site.

The target site includes a donor site, wherein the plurality of incised skin pixels is harvested at the donor site.

The target site includes a recipient site, wherein the incised skin pixels generate skin defects at the recipient site.

The method comprises capturing the plurality of incised skin pixels using an adherent substrate and transferring the plurality of incised skin pixels to the recipient site.

The method comprises the adherent substrate maintaining relative positioning of the plurality of incised skin pixels during the transferring to the recipient site.

The method comprises applying the plurality of incised skin pixels from the adherent substrate to the skin defects at the recipient site.

The method comprises aligning the plurality of incised skin pixels with the skin defects at the recipient site using the adherent substrate.

The method comprises inserting each incised skin pixel from the adherent substrate into a corresponding skin defect at the recipient site.

The method comprises applying at least one bandage at the target site.

The applying the at least one bandage comprises applying force to close the target site.

The applying the at least one bandage comprises applying directional force to control a direction of the closure at the target site.

The applying of the at least one bandage comprises applying a first bandage at the donor site.

The applying of the at least one bandage comprises applying a second bandage at the recipient site.

The generating the plurality of incised skin pixels comprises transferring a load via the scalpet device to subjacent skin surface that includes the target site, wherein the skin pixels are incised by application of the load.

The generating the plurality of incised skin pixels comprises transferring a load via the scalpet array to subjacent skin surface that includes the target site, wherein the skin pixels are incised by application of the load.

The scalpet device is configured to be disposable.

The scalpet device is configured to be at least one of cleaned, disinfected, and sterilized.

The method comprises positioning a template at the target site.

The method comprises aligning the scalpet device with the template.

The method comprises aligning the scalpet array with the template.

The positioning comprises positioning the template on a skin surface at the target site.

The template comprises an indicator on the skin surface at the target site.

The template includes a guide plate configured for positioning at the target site and comprising perforations arranged in a pattern.

The method comprises removeably coupling the scalpet array to the scalpet device.

The scalpet array is disposable.

A shape of each scalpet of the scalpet array is elliptical.

A shape of each scalpet of the scalpet array is circular.

A shape of each scalpet of the scalpet array is semicircular.

A shape of each scalpet of the scalpet array is one of square, rectangular, and flat.

Each scalpet of the plurality of scalpets includes a beveled surface.

Each scalpet of the plurality of scalpets includes at least one pointed surface.

Each scalpet of the plurality of scalpets includes at least one needle.

The at least one needle comprises at least one needle including multiple points. The generating of the plurality of incised pixels comprises generating using at least one of piercing force, impact force, and rotational force.

The generating of the plurality of incised pixels comprises generating using radio frequency (RF) energy.

The generating of the plurality of incised pixels comprises generating using vibrational energy.

At least one scalpet of the scalpet array comprises a through orifice.

At least one diametric dimension of each scalpet of the scalpet array is approximately in a range 0.5 millimeters to 4.0 millimeters.

The method comprises positioning a guide plate as a template at the target site, wherein the guide plate includes perforations arranged in a pattern.

The method comprises aligning the scalpet array with the perforations in the guide plate.

The method comprises applying the scalpet array to a donor site via the perforations in the guide plate, wherein the plurality of skin pixels are incised.

The method comprises applying the scalpet array to a recipient site via the perforations in the guide plate, wherein a plurality of skin defects are generated.

The target site includes the donor site and the recipient site.

The method comprises generating the plurality of incised skin pixels and the plurality of skin defects according to the pattern.

The method comprises capturing with an adherent substrate the plurality of incised skin pixels at the donor site and transferring the plurality of incised skin pixels to the recipient site.

The method comprises maintaining with the adherent substrate relative positioning of the plurality of incised skin pixels during transferring to and application at the recipient site.

The method comprises applying the scalpet array to the donor site directly through the perforations and the skin pixels are incised.

The method comprises applying the scalpet array to the recipient site directly through the perforations and the skin defects are generated.

The guide plate is at least one of adherent, rigid, semi-rigid, conformable, non-conformable, and non-deformable.

The guide plate includes at least one of metal, plastic, polymer, and membranous material.

The guide plate is configured to transmit a load to a skin surface of at least one of the donor site and the recipient site.

The method comprises positioning the guide plate directly on a skin surface at the target site.

The method comprises extruding the plurality of incised skin pixels using the guide plate.

The method comprises extruding the plurality of skin pixels through the perforations in response to an applied load.

The method comprises extruding the plurality of skin pixels through the incised skin surface in response to an applied load.

The generating of the plurality of incised skin pixels comprises incising with a cutting member.

The method comprises transceting the incised skin pixels with the cutting member.

The method comprises capturing the incised skin pixels with an adherent substrate.

The cutting member is coupled to a frame.

The frame is coupled to a guide plate, wherein the guide plate is configured as a guide for the scalpet device.

The adherent substrate is coupled to at least one of the frame and the guide plate.

The incised skin pixels include hair follicles.

The method comprises using the skin defects to evoke neovascularization in the incised skin pixels inserted at the recipient site The method comprises using the skin defects to evoke a wound healing response in the incised skin pixels inserted at the recipient site.

Embodiments include a method comprising: forming a coupling between a control device and a scalpet device, wherein the control device includes an actuator, wherein the scalpet device includes a scalpet array comprising a plurality of scalpets arranged in a pattern; aligning the scalpet device at a target site; and generating a plurality of incised skin pixels and a plurality of skin defects by deploying the scalpet array into tissue at the target site, wherein the scalpet array is deployed in response to activation of the actuator.

Embodiments include a method comprising: forming a coupling between a control device and a scalpet device, wherein the control device includes an actuator, wherein the scalpet device includes a scalpet array comprising a plurality of scalpets arranged in a pattern; aligning the scalpet device at a target site; and generating a plurality of incised skin pixels and a plurality of skin defects by deploying the scalpet array into tissue at the target site, wherein the scalpet array is deployed in response to activation of the actuator.

Embodiments include a method comprising: positioning a housing at a target site, wherein the housing includes a scalpet array comprising a plurality of scalpets arranged in a pattern; deploying the scalpet array into tissue at the target site; generating a plurality of incised skin pixels at the target site when the target site is a donor site; generating a plurality of skin defects at the target site when the target site is a recipient site; and harvesting the plurality of incised skin pixels.

Embodiments include a method comprising: positioning a housing at a target site, wherein the housing includes a scalpet array comprising a plurality of scalpets arranged in a pattern; deploying the scalpet array into tissue at the target site; generating a plurality of incised skin pixels at the target site when the target site is a donor site; generating a plurality of skin defects at the target site when the target site is a recipient site; and harvesting the plurality of incised skin pixels.

Embodiments include a method comprising: positioning a housing at a donor site, wherein the housing includes a scalpet array comprising a plurality of scalpets arranged in a pattern; deploying the scalpet array into tissue at the donor site and generating a plurality of incised skin pixels; capturing the plurality of incised skin pixels at the donor site and transferring the incised skin pixels to a recipient; positioning the housing at the recipient site, and deploying the scalpet array into tissue at the recipient site and generating a plurality of skin defects; and applying the plurality of incised skin pixels to the skin defects at the recipient site.

Embodiments include a method comprising: positioning a housing at a donor site, wherein the housing includes a scalpet array comprising a plurality of scalpets arranged in a pattern; deploying the scalpet array into tissue at the donor site and generating a plurality of incised skin pixels; capturing the plurality of incised skin pixels at the donor site and transferring the incised skin pixels to a recipient; positioning the housing at the recipient site, and deploying the scalpet array into tissue at the recipient site and generating a plurality of skin defects; and applying the plurality of incised skin pixels to the skin defects at the recipient site.

Embodiments include a method comprising: configuring a housing to include a scalpet device; and configuring the scalpet device to include a substrate and a scalpet array, wherein the scalpet array is configured to include a plurality of scalpets arranged in a configuration on the substrate, wherein the substrate and the plurality of scalpets is configured to be deployed from the housing and retracted into the housing, wherein the plurality of scalpets is configured to generate a plurality of incised skin pixels at a target site when deployed.

Embodiments include a method comprising: configuring a housing to include a scalpet device; and configuring the scalpet device to include a substrate and a scalpet array, wherein the scalpet array is configured to include a plurality of scalpets arranged in a configuration on the substrate, wherein the substrate and the plurality of scalpets is configured to be deployed from the housing and retracted into the housing, wherein the plurality of scalpets is configured to generate a plurality of incised skin pixels at a target site when deployed.

The method comprises configuring the housing to be removeably coupled to a receiver.

The receiver is a component of a control device.

The method comprises configuring the control device to include a proximal end and a distal end, wherein the proximal end includes an actuator mechanism and the distal end includes the receiver.

The method comprises configuring the scalpet array to be deployed in response to activation of the actuator mechanism.

The method comprises configuring the proximal end of the control device to be hand-held.

The method comprises configuring the scalpet device so the scalpet array is deployed from the scalpet device and retracted back into the scalpet device in response to activation of the actuator mechanism.

The method comprises configuring the scalpet device so the scalpet array is deployed from the scalpet device in response to activation of the actuator mechanism.

The method comprises configuring the scalpet device so the scalpet array is retracted back into the scalpet device in response to release of the actuator mechanism.

The method comprises configuring the control device to be disposable.

The method comprises configuring the control device to be at least one of cleaned, disinfected, and sterilized.

The method comprises configuring an adherent substrate to capture the plurality of incised skin pixels.

The method comprises configuring the scalpet device to include the adherent substrate.

The method comprises configuring the housing to include the adherent substrate.

The adherent substrate comprises a flexible substrate.

The adherent substrate comprises a semi-porous membrane.

The method comprises configuring at least one of the housing, the scalpet device, and the scalpet array for use with a vacuum component.

The method comprises configuring the housing for coupling to the vacuum component.

The method comprises configuring the scalpet device for coupling to the vacuum component for coupling to the scalpet device.

The method comprises configuring the scalpet device for coupling to the vacuum component via the housing.

The method comprises configuring at least one of the scalpet device and the control device to include a low-pressure zone.

The method comprises configuring the low-pressure zone to evacuate the plurality of incised skin pixels.

The method comprises configuring the housing to be removeably coupled to a control device, wherein the vacuum component is coupled to the control device. The method comprises configuring at least one of the housing, the scalpet device, and the scalpet array for use with a radio frequency (RF) component.

The method comprises configuring the RF component to provide thermal energy to at least one of the scalpet device and the scalpet array.

The method comprises configuring the RF component to provide vibrational energy to at least one of the scalpet device and the scalpet array.

The method comprises configuring the RF component to provide rotational energy to at least one of the scalpet device and the scalpet array.

The method comprises configuring the RF component to provide acoustic energy to at least one of the scalpet device and the scalpet array.

The method comprises coupling the RF component to the housing.

The method comprises coupling the RF component to the scalpet device.

The method comprises coupling the RF component to the scalpet device via the housing.

The method comprises coupling the RF component to the scalpet array.

The method comprises coupling the RF component to the scalpet array via the housing.

The method comprises coupling the RF component to at least one scalpet of the scalpet array.

The method comprises coupling the RF component to the at least one scalpet of the scalpet array via the housing.

The method comprises configuring the housing to be removeably coupled to a control device, wherein the RF component is coupled to the control device.

The method comprises coupling a vacuum component at least one of the scalpet device and the housing, and coupling a radio frequency (RF) component at least one of the scalpet device, the scalpet array, and the housing.

The method comprises configuring at least one of the scalpet device and the housing to include a low-pressure zone.

The method comprises configuring at least one of the scalpet device, the scalpet array, and the housing to receive energy from the RF component.

The energy comprises at least one of thermal energy, vibrational energy, rotational energy, and acoustic energy.

The target site includes a recipient site, wherein the incised skin pixels generate skin defects at the recipient site.

The target site includes a donor site, wherein the plurality of incised skin pixels is harvested at the donor site.

The target site includes a recipient site, wherein the incised skin pixels generate skin defects at the recipient site.

The method comprises configuring an adherent substrate to capture the plurality of incised skin pixels at the donor site and transfer the plurality of incised skin pixels to the recipient site.

The method comprises configuring the adherent substrate to maintain relative positioning of the plurality of incised skin pixels during transfer to and application at the recipient site.

The method comprises configuring the adherent substrate to apply the incised skin pixels to the skin defects at the recipient site.

The method comprises configuring the adherent substrate to align the incised skin pixels with the skin defects at the recipient site.

The method comprises configuring the adherent substrate to insert each incised skin pixel into a corresponding skin defect at the recipient site.

The method comprises configuring at least one bandage for application at the target site.

The method comprises configuring the at least one bandage to apply force to close the target site.

The method comprises configuring the at least one bandage to apply directional force to control a direction of the closure at the target site.

The at least one bandage includes a first bandage configured for application at the donor site.

The at least one bandage includes a second bandage configured for application at the recipient site.

The method comprises configuring the scalpet device to transfer a load to subjacent skin surface that includes the target site, wherein the skin pixels are incised by application of the load.

The method comprises configuring the scalpet array to transfer a load to subjacent skin surface that includes the target site, wherein the skin pixels are incised by application of the load.

The method comprises configuring the scalpet device to be disposable.

The method comprises configuring the scalpet device to be at least one of cleaned, disinfected, and sterilized.

The method comprises configuring a template for positioning at the target site.

The method comprises configuring the scalpet device to align with the template.

The method comprises configuring the scalpet array to align with the template.

The template is on a skin surface at the target site.

The template comprises an indicator on the skin surface at the target site.

The template includes a guide plate configured for positioning at the target site and comprising perforations arranged in a pattern.

The scalpet array is removeably coupled to the scalpet device.

The scalpet array is disposable.

A shape of each scalpet of the scalpet array is elliptical.

A shape of each scalpet of the scalpet array is circular.

A shape of each scalpet of the scalpet array is semicircular.

A shape of each scalpet of the scalpet array is one of square, rectangular, and flat.

Each scalpet of the at least one scalpet includes a beveled surface.

Each scalpet of the plurality of scalpets includes at least one pointed surface.

Each scalpet of the plurality of scalpets includes at least one needle.

The at least one needle comprises at least one needle including multiple points.

The method comprises configuring the scalpet array to generate the incised skin pixels using at least one of piercing force, impact force, and rotational force.

The method comprises configuring the scalpet array to generate the incised skin pixels using radio frequency (RF) energy.

The method comprises configuring the scalpet array to generate the incised skin pixels using vibrational energy.

At least one scalpet of the scalpet array comprises a through orifice.

At least one diametric dimension of each scalpet of the scalpet array is approximately in a range 0.5 millimeters to 4.0 millimeters.

The method comprises configuring a guide plate for positioning as a template at the target site, wherein the guide plate includes perforations arranged in a pattern.

The method comprises configuring the scalpet array to align with the perforations in the guide plate.

The method comprises configuring the scalpet array to be applied to a donor site via the perforations in the guide plate, wherein the plurality of skin pixels are incised.

The method comprises configuring the scalpet array to be applied to a recipient site via the perforations in the guide plate, wherein a plurality of skin defects are generated.

The target site includes the donor site and the recipient site.

The plurality of incised skin pixels and the plurality of skin defects are generated according to the pattern.

The method comprises configuring an adherent substrate to capture the plurality of incised skin pixels at the donor site and transfer the plurality of incised skin pixels to the recipient site.

The method comprises configuring the adherent substrate to maintain relative positioning of the plurality of incised skin pixels during transfer to and application at the recipient site.

The method comprises configuring the scalpet array to be applied to the donor site directly through the perforations to incise the skin pixels.

The method comprises configuring the scalpet array to be applied to the recipient site directly through the perforations to generate the skin defects.

The method comprises configuring the guide plate to be at least one of adherent, rigid, semi-rigid, conformable, non-conformable, and non-deformable.

The method comprises configuring the guide plate to include at least one of metal, plastic, polymer, and membranous material.

The method comprises configuring the guide plate to transmit a load to a skin surface of at least one of the donor site and the recipient site.

The method comprises configuring the guide plate to be positioned directly on a skin surface at the target site.

The method comprises configuring the guide plate to extrude the plurality of incised skin pixels.

The plurality of skin pixels is extruded through the perforations in response to an applied load.

The plurality of skin pixels is extruded through the incised skin surface in response to an applied load.

The method comprises configuring at least one of the housing, the scalpet device, and the scalpet array for use with a cutting member.

The incised skin pixels are transected by the cutting member.

The method comprises configuring an adherent substrate to capture the incised skin pixels.

The method comprises configuring the cutting member to be coupled to a frame. The frame is coupled to a guide plate, wherein the guide plate is configured as a guide for the scalpet device.

The method comprises configuring the adherent substrate to be coupled to at least one of the frame and the guide plate.

The incised skin pixels include hair follicles.

The method comprises configuring the skin defects to evoke neovascularization in the incised skin pixels inserted at the recipient site.

The method comprises configuring the skin defects to evoke a wound healing response in the incised skin pixels inserted at the recipient site.

Embodiments include a method comprising configuring a housing to include a scalpet device. The method includes configuring the scalpet device to include a scalpet array comprising a plurality of scalpets arranged in a pattern. The plurality of scalpets is configured to be deployed from the housing and generate a plurality of incised skin pixels at a target site.

Embodiments include a method comprising: configuring a housing to include a scalpet device; and configuring the scalpet device to include a scalpet array comprising a plurality of scalpets arranged in a pattern, wherein the plurality of scalpets is configured to be deployed from the housing and generate a plurality of incised skin pixels at a target site.

Embodiments include a method comprising configuring a control device to include a proximal end and a distal end. The proximal end includes an actuator. The method includes configuring a housing to include a scalpet device and for removeable coupling to the distal end of the control device. The method includes configuring the scalpet device to include a scalpet array comprising a plurality of scalpets arranged in a pattern. The plurality of scalpets is configured to be deployed from the housing to generate a plurality of incised skin pixels at a target site when deployed.

Embodiments include a method comprising: configuring a control device to include a proximal end and a distal end, wherein the proximal end includes an actuator; configuring a housing to include a scalpet device and for removeable coupling to the distal end of the control device; and configuring the scalpet device to include a scalpet array comprising a plurality of scalpets arranged in a pattern, wherein the plurality of scalpets is configured to be deployed from the housing to generate a plurality of incised skin pixels at a target site when deployed.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments is not intended to be exhaustive or to limit the systems and methods to the precise forms disclosed. While specific embodiments of, and examples for, the medical devices and methods are described herein for illustrative purposes, various equivalent modifications are possible within the scope of the systems and methods, as those skilled in the relevant art will recognize. The teachings of the medical devices and methods provided herein can be applied to other systems and methods, not only for the systems and methods described above.

The elements and acts of the various embodiments described above can be combined to provide further embodiments. These and other changes can be made to the medical devices and methods in light of the above detailed description.

In general, in the following claims, the terms used should not be construed to limit the medical devices and methods and corresponding systems and methods to the specific embodiments disclosed in the specification and the claims, but should be construed to include all systems that operate under the claims. Accordingly, the medical devices and methods and corresponding systems and methods are not limited by the disclosure, but instead the scope is to be determined entirely by the claims.

While certain aspects of the medical devices and methods and corresponding systems and methods are presented below in certain claim forms, the inventors contemplate the various aspects of the medical devices and methods and corresponding systems and methods in any number of claim forms. Accordingly, the inventors reserve the right to add additional claims after filing the application to pursue such additional claim forms for other aspects of the medical devices and methods and corresponding systems and methods.

What is claimed is:

1. A method comprising:
    positioning at a target site a housing comprising a scalpet device, where in the scalpet device includes a substrate and a scalpet array, wherein the scalpet array includes a plurality of scalpets arranged in a configuration on the substrate;
    deploying the scalpet array from the housing into tissue at the target site and generating a plurality of incised skin pixels at the target site, wherein the generating of the plurality of incised skin pixels comprises providing energy using a radio frequency (RF) component to provide rotational energy to at least one of the scalpet device and the scalpet array; and
    retracting the scalpet array into the housing from the target site.

2. The method of claim 1, comprising coupling the housing to a receiver that is a component of a control device.

3. The method of claim 2, wherein the control device comprises a proximal end and a distal end, wherein the proximal end includes an actuator mechanism and the distal end includes the receiver.

4. The method of claim 3, wherein the deploying comprising deploying the scalpet array in response to activation of the actuator mechanism.

5. The method of claim 3, wherein the retracting comprises retracting the scalpet array in response to activation of the actuator mechanism.

6. The method of claim 3, wherein the retracting comprises retracting the scalpet array in response to release of the actuator mechanism.

7. The method of claim 3, wherein the proximal end of the control device is configured to be hand-held.

8. The method of claim 3, comprising decoupling the scalpet device from the receiver and disposing of the scalpet device.

9. The method of claim 3, comprising at least one of cleaning, disinfecting, and sterilizing the control device.

10. The method of claim 1, comprising capturing the plurality of incised skin pixels using an adherent substrate.

11. The method of claim 10, wherein the adherent substrate comprises a flexible substrate.

12. The method of claim 10, wherein the adherent substrate comprises a semi-porous membrane.

13. The method of claim 1, comprising harvesting the plurality of incised skin pixels.

14. The method of claim 13, wherein the harvesting comprises evacuating the plurality of incised skin pixels.

15. The method of claim 13, wherein the harvesting comprises generating a low pressure zone within at least one of the scalpet device and the housing.

16. The method of claim 15, wherein the generating of the low pressure zone comprises using a vacuum component.

17. The method of claim 16, wherein the vacuum component is coupled to the housing.

18. The method of claim 16, wherein the vacuum component is coupled to the scalpet device.

19. The method of claim 16, wherein the vacuum component is coupled to the scalpet device via the housing.

20. The method of claim 16, wherein the housing is configured to be removeably coupled to a control device, wherein the vacuum component is coupled to the control device.

21. The method of claim 1, wherein the energy further comprises at least one of thermal energy, vibrational energy, and acoustic energy.

22. The method of claim 1, wherein the providing the energy further comprises providing thermal energy to at least one of the scalpet device and the scalpet array.

23. The method of claim 1, wherein the providing the energy further comprises providing vibrational energy to at least one of the scalpet device and the scalpet array.

24. The method of claim 1, wherein the providing the energy further comprises providing acoustic energy to at least one of the scalpet device and the scalpet array.

25. The method of claim 1, wherein the RF component is coupled to the housing.

26. The method of claim 1, wherein the RF component is coupled to the scalpet device.

27. The method of claim 1, wherein the RF component is coupled to the scalpet device via the housing.

28. The method of claim 1, wherein the RF component is coupled to the scalpet array.

29. The method of claim 1, wherein the RF component is coupled to the scalpet array via the housing.

30. The method of claim 1, wherein the RF component is coupled to at least one scalpet of the scalpet array.

31. The method of claim 1, wherein the RF component is coupled to the at least one scalpet of the scalpet array via the housing.

32. The method of claim 1, wherein the housing is configured to be removeably coupled to a control device, wherein the RF component is coupled to the control device.

33. The method of claim 1, comprising harvesting the plurality of incised skin pixels using a vacuum component.

34. The method of claim 33, wherein the vacuum component is configured to generate a low pressure zone within at least one of the scalpet device and the housing.

35. The method of claim 33, wherein the energy further comprises at least one of thermal energy, vibrational energy, and acoustic energy.

36. The method of claim 1, wherein the target site includes a donor site, wherein the plurality of incised skin pixels are harvested at the donor site.

37. The method of claim 36, further comprising a second target site comprising a second target site comprising a recipient site including skin defects.

38. The method of claim 37, comprising capturing the plurality of incised skin pixels at the donor site using an adherent substrate and transferring the plurality of incised skin pixels to the recipient site.

39. The method of claim 38, comprising the adherent substrate maintaining relative positioning of the plurality of incised skin pixels during the transferring from the donor site to the recipient site.

40. The method of claim 38, comprising applying the plurality of incised skin pixels of the donor site from the adherent substrate to the skin defects at the recipient site.

41. The method of claim 38, comprising aligning the plurality of incised skin pixels of the donor site with the skin defects at the recipient site using the adherent substrate.

42. The method of claim 41, comprising inserting each incised skin pixel from the adherent substrate into a corresponding skin defect at the recipient site.

43. The method of claim 37, comprising applying at least one bandage at the target site.

44. The method of claim 43, wherein the applying the at least one bandage comprises applying force to close the target site.

45. The method of claim 43, wherein the applying the at least one bandage comprises applying directional force to control a direction of the closure at the target site.

46. The method of claim 45, wherein the applying of the at least one bandage comprises applying a first bandage at the donor site.

47. The method of claim 45, wherein the applying of the at least one bandage comprises applying a second bandage at the recipient site.

48. The method of claim 1, wherein the generating the plurality of incised skin pixels comprises transferring a load via the scalpet device to subjacent skin surface that includes the target site, wherein the skin pixels are incised by application of the load.

49. The method of claim 1, wherein the generating the plurality of incised skin pixels comprises transferring a load via the scalpet array to subjacent skin surface that includes the target site, wherein the skin pixels are incised by application of the load.

50. The method of claim 1, wherein the scalpet device is configured to be disposable.

51. The method of claim 1, wherein the scalpet device is configured to be at least one of cleaned, disinfected, and sterilized.

52. The method of claim 1, comprising positioning a template at the target site.

53. The method of claim 52, comprising aligning the scalpet device with the template.

54. The method of claim 52, comprising aligning the scalpet array with the template.

55. The method of claim 52, wherein the positioning comprises positioning the template on a skin surface at the target site.

56. The method of claim 55, wherein the template comprises an indicator on the skin surface at the target site.

57. The method of claim 55, wherein the template includes a guide plate configured for positioning at the target site and comprising perforations arranged in a pattern.

58. The method of claim 1, comprising removeably coupling the scalpet array to the scalpet device.

59. The method of claim 1, wherein the scalpet array is disposable.

60. The method of claim 1, wherein a shape of each scalpet of the scalpet array is elliptical.

61. The method of claim 1, wherein a shape of each scalpet of the scalpet array is circular.

62. The method of claim 1, wherein each scalpet of the plurality of scalpets includes a beveled surface.

63. The method of claim 1, wherein each scalpet of the plurality of scalpets includes at least one pointed surface.

64. The method of claim 1, wherein each scalpet of the plurality of scalpets includes at least one needle.

65. The method of claim 64, wherein the at least one needle comprises at least one needle including multiple points.

66. The method of claim 1, wherein the generating of the plurality of incised pixels comprises generating using at least one of piercing force and impact force.

67. The method of claim 1, wherein the generating of the plurality of incised pixels comprises generating using vibrational energy.

68. The method of claim 1, wherein at least one scalpet of the scalpet array comprises a through orifice.

69. The method of claim 1, wherein at least one diametric dimension of each scalpet of the scalpet array is approximately in a range 0.5 millimeters to 4.0 millimeters.

70. The method of claim 1, comprising positioning a guide plate as a template at the target site, wherein the guide plate includes perforations arranged in a pattern.

71. The method of claim 70, comprising aligning the scalpet array with the perforations in the guide plate.

72. The method of claim 70, comprising applying the scalpet array to a donor site via the perforations in the guide plate, wherein the plurality of skin pixels are incised.

73. The method of claim 72, comprising applying the scalpet array to a recipient site via the perforations in the guide plate, wherein a second plurality of skin pixels are incised to generate a plurality of skin defects configured to receive the plurality of skin pixels.

74. The method of claim 73, comprising generating the plurality of incised skin pixels and the plurality of skin defects according to the pattern.

75. The method of claim 73, comprising capturing with an adherent substrate the plurality of incised skin pixels at the donor site and transferring the plurality of incised skin pixels to the plurality of skin defects at the recipient site.

76. The method of claim 75, comprising maintaining with the adherent substrate relative positioning of the plurality of incised skin pixels during transferring to and application at the recipient site.

77. The method of claim 73, comprising applying the scalpet array to the donor site directly through the perforations and the skin pixels are incised.

78. The method of claim 73, comprising applying the scalpet array to the recipient site directly through the perforations and the plurality of skin defects are generated.

79. The method of claim 70, wherein the guide plate is at least one of adherent, rigid, semi-rigid, conformable, non-conformable, and non-deformable.

80. The method of claim 70, wherein the guide plate includes at least one of metal, plastic, polymer, and membranous material.

81. The method of claim 70, wherein the guide plate is configured to transmit a load to a skin surface of the target site.

82. The method of claim 70, comprising positioning the guide plate directly on a skin surface at the target site.

83. The method of claim 82, comprising extruding the plurality of incised skin pixels using the guide plate.

84. The method of claim 83, comprising extruding the plurality of skin pixels through the perforations in response to an applied load.

85. The method of claim 83, comprising extruding the plurality of skin pixels through the incised skin surface in response to an applied load.

86. The method of claim 1, wherein the generating of the plurality of incised skin pixels comprises incising with a cutting member.

87. The method of claim 86, comprising transecting the incised skin pixels with the cutting member.

88. The method of claim 87, comprising capturing the incised skin pixels with an adherent substrate.

89. The method of claim 88, wherein the cutting member is coupled to a frame.

90. The method of claim 89, wherein the frame is coupled to a guide plate, wherein the guide plate is configured as a guide for the scalpet device.

91. The method of claim 89, wherein the adherent substrate is coupled to at least one of the frame and the guide plate.

92. The method of claim 1, wherein the incised skin pixels include hair follicles.

93. The method of claim 1, comprising transferring the plurality of incised skin pixels to a plurality of skin defects at a recipient site, wherein the skin defects are configured to evoke neovascularization in the incised skin pixels inserted at the recipient site.

94. The method of claim 1, comprising transferring the plurality of incised skin pixels to a plurality of skin defects at a recipient site, wherein the skin defects are configured to evoke a wound healing response in the incised skin pixels inserted at the recipient site.

* * * * *